US012723086B2

(12) United States Patent
Kang et al.

(10) Patent No.: US 12,723,086 B2
(45) **Date of Patent: *Sep. 1, 2026**

(54) ANTIBODIES BINDING 4-1BB AND USES THEREOF

(71) Applicant: Nanjing Leads Biolabs Co., Ltd., Nanjing (CN)

(72) Inventors: Xiaoqiang Kang, Plainsboro, NJ (US); Xiao Huang, Nanjing (CN); Jianming Sun, Nanjing (CN)

(73) Assignee: Nanjing Leads Biolabs Co., Ltd., Nanjing (CN)

( * ) Notice: Subject to any disclaimer, the term of this patent is extended or adjusted under 35 U.S.C. 154(b) by 911 days.

This patent is subject to a terminal disclaimer.

(21) Appl. No.: 18/045,133

(22) Filed: Oct. 7, 2022

(65) Prior Publication Data

US 2023/0192862 A1 Jun. 22, 2023

Related U.S. Application Data

(62) Division of application No. 17/038,669, filed on Sep. 30, 2020, now Pat. No. 11,466,086.

(60) Provisional application No. 62/913,744, filed on Oct. 11, 2019.

(51) Int. Cl.
*C07K 16/00* (2006.01)
*A61P 35/00* (2006.01)
*C07K 16/28* (2006.01)
*C07K 16/30* (2006.01)

(52) U.S. Cl.
CPC .......... *C07K 16/2827* (2013.01); *A61P 35/00* (2018.01); *C07K 16/30* (2013.01); *C07K 2317/24* (2013.01); *C07K 2317/31* (2013.01); *C07K 2317/51* (2013.01); *C07K 2317/54* (2013.01); *C07K 2317/565* (2013.01); *C07K 2317/622* (2013.01)

(58) Field of Classification Search
CPC ................ C07K 16/2827; C07K 16/30; C07K 2317/24; C07K 2317/31; C07K 2317/51; C07K 2317/54; C07K 2317/565
See application file for complete search history.

(56) References Cited

U.S. PATENT DOCUMENTS

| | | | |
|---|---|---|---|
| 11,466,086 | B2 | 10/2022 | Kang et al. |
| 2017/0198050 | A1 | 7/2017 | Eckelman et al. |
| 2018/0118841 | A1 | 5/2018 | Ellmark et al. |

FOREIGN PATENT DOCUMENTS

| | | | |
|---|---|---|---|
| CN | 109021107 | A | 12/2018 |
| CN | 109762066 | A | 5/2019 |
| EP | 3470426 | A1 | 4/2019 |
| JP | 2018-520650 | A1 | 11/2016 |
| JP | 2019-504831 | A | 2/2019 |
| WO | WO 2005/035584 | A1 | 4/2005 |
| WO | WO 2016/134358 | A1 | 8/2016 |
| WO | WO 2017/123650 | A2 | 7/2017 |
| WO | WO 2018/045110 | A1 | 3/2018 |
| WO | WO 2018/056821 | A1 | 3/2018 |
| WO | WO 2018/156740 | A1 | 8/2018 |
| WO | WO 2019/025545 | A1 | 2/2019 |
| WO | WO 2019/072868 | A1 | 4/2019 |
| WO | WO 2020/025659 | A1 | 2/2020 |
| WO | WO 2020/102233 | A1 | 5/2020 |
| WO | WO 2020/107715 | A1 | 6/2020 |

OTHER PUBLICATIONS

Chester et al., Immunotherapy targeting 4-1BB: mechanistic rationale, clinical results, and future strategies. Blood. 2018; 131(1):49-57.

Drenkard et al., CD137 is expressed on blood vessel walls at sites of inflammation and enhances monocyte migratory activity. FASEB J. 2007;21(2):456-463.

Lakins et al., FS222, a CD137/PD-L1 Tetravalent Bispecific Antibody, Exhibits Low Toxicity and Antitumor Activity in Colorectal Cancer Models. Clin Cancer Res. Apr. 28, 2020;26:4154-4167. DOI: 10.1158/1078-0432.CCR-19-2958.

Mcgrath et al., The role of coinhibitory signaling pathways in transplantation and tolerance. Front Immunol. Mar. 19, 2012;3:47. doi: 10.3389/fimmu.2012.00047. PMID: 22566929; PMCID: PMC3342378.

Middendorp et al., Mice deficient for CD137 ligand are predisposed to develop germinal center-derived B-cell lymphoma. Blood. 2009;114(11):2280-2289.

Palazon et al., Agonist Anti-CD137 mAb Act on Tumor Endothelial Cells to Enhance Recruitment of Activated T Lymphocytes. Cancer Res. 2011;71(3): 801-811.

Seo et al., 4-1BB-mediated immunotherapy of rheumatoid arthritis. Nature Med. 2004;10(10):1088-1094.

Sun et al., Administration of Agonistic Anti-4-1BB Monoclonal Antibody Leads to the Amelioration of Experimental Autoimmune Encephalomyelitis. J. Immunol. 2002;168(3):1457-1465.

Vinay et al., 4-1BB (CD137), an inducible costimulatory receptor, as a specific target for cancer therapy. BMB Rep. 2014;47(3): 122-129.

Vinay et al., CD137-Deficient Mice Have Reduced NK/NKT Cell Numners and Function, Are Resistant to Lipopolysaccharide-Induced Shock Syndromes, and Have Lower IL-4 Responses. J. Immunol. 2004; 173(6):4218-4229.

(Continued)

*Primary Examiner* — Lei Yao

(74) *Attorney, Agent, or Firm* — Wolf, Greenfield & Sacks, P.C.

(57) ABSTRACT

Disclosed is an isolated monoclonal antibody that specifically binds human 4-1BB, or the antigen-binding portion thereof. A nucleic acid molecule encoding the antibody, an expression vector, a host cell and a method for expressing the antibody are also provided. The present disclosure further provides a bispecific molecule, and a pharmaceutical composition comprising the antibody or the bispecific molecule, as well as a treatment method using an anti-4-1BB antibody of the disclosure.

19 Claims, 14 Drawing Sheets

Specification includes a Sequence Listing.

(56) References Cited

OTHER PUBLICATIONS

Zhang et al., Agonistic Anti-4-1BB Antibody Promotes the Expansion of Natural Regulatory T Cells While Maintaining Foxp3 Expression. Scand J Immunol. 2007;66(4): 435-440.

| | Urelumab | 41BB-2-IgG2 |
|---|---|---|
| EC50 | 3.668 | 0.6216 |

| | 41BB-9-IgG2 | Urelumab |
|---|---|---|
| EC50 | 0.1337 | 13.39 |

| | Urelumab | 41BB-13-IgG2 |
|---|---|---|
| EC50 | 11.12 | 1.273 |

| | Urelumab | 41BB-27-IgG2 |
|---|---|---|
| EC50 | 5.291 | 0.04997 |

| | 41BB-2-IgG2 | Urelumab |
|---|---|---|
| EC50 | 47.37 | 26.75 |

| | 41BB-2-IgG2 | 41BB-27-IgG2 |
|---|---|---|
| EC50 | 6.208 | ~ 45796314625 |

| | 41BB-2-IgG2 | 41BB-27-IgG2 |
|---|---|---|
| EC50 | 56.07 | 35.92 |

| | 41BB-9-IgG2 | Urelumab |
|---|---|---|
| EC50 | 16.56 | 34.04 |

| | 41BB-9-IgG2 |
|---|---|
| EC50 | 3.237 |

| | Urelumab | 41BB-13-IgG2 |
|---|---|---|
| EC50 | 32.34 | 105.9 |

| | 41BB-13-IgG2 |
|---|---|
| EC50 | 10.58 |

| | P4B-2 | P4B-3 |
|---|---|---|
| EC50 | 0.02395 | 0.02887 |

| | P4B-2 | P4B-3 |
|---|---|---|
| EC50 | 0.1126 | 0.07234 |

| | P4B-3 | NM21-PRO1186 |
|---|---|---|
| EC50 | 0.01324 | 0.03052 |

| | INBRX-105-1 | P4B-3 |
|---|---|---|
| EC50 | 0.01346 | 0.02264 |

SEQUENCE LISTING

```
Sequence total quantity: 85
SEQ ID NO: 1             moltype = AA  length = 5
FEATURE                  Location/Qualifiers
REGION                   1..5
                         note = construct
source                   1..5
                         mol_type = protein
                         organism = synthetic construct
SEQUENCE: 1
SYAMH                                                                    5

SEQ ID NO: 2             moltype = AA  length = 17
FEATURE                  Location/Qualifiers
REGION                   1..17
                         note = construct
```

-continued

```
source                  1..17
                        mol_type = protein
                        organism = synthetic construct
SEQUENCE: 2
VISYDGSKKW YADSVKG                                                    17

SEQ ID NO: 3            moltype = AA  length = 15
FEATURE                 Location/Qualifiers
REGION                  1..15
                        note = construct
source                  1..15
                        mol_type = protein
                        organism = synthetic construct
SEQUENCE: 3
NQGSGSYLYY YYMDV                                                      15

SEQ ID NO: 4            moltype = AA  length = 14
FEATURE                 Location/Qualifiers
REGION                  1..14
                        note = construct
source                  1..14
                        mol_type = protein
                        organism = synthetic construct
SEQUENCE: 4
TGTSSDVGGY NYVS                                                       14

SEQ ID NO: 5            moltype = AA  length = 7
FEATURE                 Location/Qualifiers
REGION                  1..7
                        note = construct
source                  1..7
                        mol_type = protein
                        organism = synthetic construct
SEQUENCE: 5
EVSNRPS                                                               7

SEQ ID NO: 6            moltype = AA  length = 11
FEATURE                 Location/Qualifiers
REGION                  1..11
                        note = construct
source                  1..11
                        mol_type = protein
                        organism = synthetic construct
SEQUENCE: 6
SSYTSSSTFY V                                                          11

SEQ ID NO: 7            moltype = AA  length = 5
FEATURE                 Location/Qualifiers
REGION                  1..5
                        note = construct
source                  1..5
                        mol_type = protein
                        organism = synthetic construct
SEQUENCE: 7
SYAIS                                                                 5

SEQ ID NO: 8            moltype = AA  length = 17
FEATURE                 Location/Qualifiers
REGION                  1..17
                        note = construct
source                  1..17
                        mol_type = protein
                        organism = synthetic construct
SEQUENCE: 8
GIIPISGAVN YAQKFQG                                                    17

SEQ ID NO: 9            moltype = AA  length = 20
FEATURE                 Location/Qualifiers
REGION                  1..20
                        note = construct
source                  1..20
                        mol_type = protein
                        organism = synthetic construct
SEQUENCE: 9
DQFIKYYDFS SGYFPNGFDI                                                 20

SEQ ID NO: 10           moltype = AA  length = 11
FEATURE                 Location/Qualifiers
REGION                  1..11
```

-continued

```
                        note = construct
source                  1..11
                        mol_type = protein
                        organism = synthetic construct
SEQUENCE: 10
SGDKLGDKYA A                                                        11

SEQ ID NO: 11           moltype = AA  length = 7
FEATURE                 Location/Qualifiers
REGION                  1..7
                        note = construct
source                  1..7
                        mol_type = protein
                        organism = synthetic construct
SEQUENCE: 11
QDTVRPS                                                             7

SEQ ID NO: 12           moltype = AA  length = 9
FEATURE                 Location/Qualifiers
REGION                  1..9
                        note = construct
source                  1..9
                        mol_type = protein
                        organism = synthetic construct
SEQUENCE: 12
QTWVSSTGV                                                           9

SEQ ID NO: 13           moltype = AA  length = 5
FEATURE                 Location/Qualifiers
REGION                  1..5
                        note = construct
source                  1..5
                        mol_type = protein
                        organism = synthetic construct
SEQUENCE: 13
SYYMH                                                               5

SEQ ID NO: 14           moltype = AA  length = 17
FEATURE                 Location/Qualifiers
REGION                  1..17
                        note = construct
source                  1..17
                        mol_type = protein
                        organism = synthetic construct
SEQUENCE: 14
IINPSGGSTS YAQKFQG                                                  17

SEQ ID NO: 15           moltype = AA  length = 21
FEATURE                 Location/Qualifiers
REGION                  1..21
                        note = construct
source                  1..21
                        mol_type = protein
                        organism = synthetic construct
SEQUENCE: 15
DLGEGYDFWS GYYTPSGAFD I                                             21

SEQ ID NO: 16           moltype = AA  length = 14
FEATURE                 Location/Qualifiers
REGION                  1..14
                        note = construct
source                  1..14
                        mol_type = protein
                        organism = synthetic construct
SEQUENCE: 16
TGTSSDVGGY NYVS                                                     14

SEQ ID NO: 17           moltype = AA  length = 7
FEATURE                 Location/Qualifiers
REGION                  1..7
                        note = construct
source                  1..7
                        mol_type = protein
                        organism = synthetic construct
SEQUENCE: 17
DVTTRPS                                                             7

SEQ ID NO: 18           moltype = AA  length = 10
FEATURE                 Location/Qualifiers
```

-continued

```
REGION                  1..10
                        note = construct
source                  1..10
                        mol_type = protein
                        organism = synthetic construct
SEQUENCE: 18
SSYTSYSTWV                                                  10

SEQ ID NO: 19           moltype = AA  length = 6
FEATURE                 Location/Qualifiers
REGION                  1..6
                        note = construct
source                  1..6
                        mol_type = protein
                        organism = synthetic construct
SEQUENCE: 19
SSHWWS                                                      6

SEQ ID NO: 20           moltype = AA  length = 16
FEATURE                 Location/Qualifiers
REGION                  1..16
                        note = construct
source                  1..16
                        mol_type = protein
                        organism = synthetic construct
SEQUENCE: 20
EIYHSGRTYY NPSLKS                                           16

SEQ ID NO: 21           moltype = AA  length = 8
FEATURE                 Location/Qualifiers
REGION                  1..8
                        note = construct
source                  1..8
                        mol_type = protein
                        organism = synthetic construct
SEQUENCE: 21
EDGGIMDV                                                    8

SEQ ID NO: 22           moltype = AA  length = 11
FEATURE                 Location/Qualifiers
REGION                  1..11
                        note = construct
source                  1..11
                        mol_type = protein
                        organism = synthetic construct
SEQUENCE: 22
QGDSLRRFYA S                                                11

SEQ ID NO: 23           moltype = AA  length = 7
FEATURE                 Location/Qualifiers
REGION                  1..7
                        note = construct
source                  1..7
                        mol_type = protein
                        organism = synthetic construct
SEQUENCE: 23
GKNNRPS                                                     7

SEQ ID NO: 24           moltype = AA  length = 11
FEATURE                 Location/Qualifiers
REGION                  1..11
                        note = construct
source                  1..11
                        mol_type = protein
                        organism = synthetic construct
SEQUENCE: 24
SSRDRSGYRW V                                                11

SEQ ID NO: 25           moltype = AA  length = 124
FEATURE                 Location/Qualifiers
REGION                  1..124
                        note = construct
source                  1..124
                        mol_type = protein
                        organism = synthetic construct
SEQUENCE: 25
QVQLQESGGG LVQPGGSLRL SCAVSGFTFS SYAMHWVRQA PGKGLEWVAV ISYDGSKKWY  60
ADSVKGRFTI SRDNSKNTLY LQMNSLRAED TAVYYCARNQ GSGSYLYYYY MDVWGKGTTV  120
TVSS                                                        124
```

```
SEQ ID NO: 26           moltype = AA  length = 112
FEATURE                 Location/Qualifiers
REGION                  1..112
                        note = construct
source                  1..112
                        mol_type = protein
                        organism = synthetic construct
SEQUENCE: 26
QSALTQPRSV SGSPGQSVTI SCTGTSSDVG GYNYVSWYQQ LPGKAPKVII YEVSNRPSGV  60
SNRFSGSKSG NTASLTISGV QSEDEADYYC SSYTSSSTFY VFGTGTQLTV LX          112

SEQ ID NO: 27           moltype = AA  length = 129
FEATURE                 Location/Qualifiers
REGION                  1..129
                        note = construct
source                  1..129
                        mol_type = protein
                        organism = synthetic construct
SEQUENCE: 27
QVQLVQSGAE VKKPGSSVKV SCKASGGTFS SYAISWVRQA PGQGLEWMGG IIPISGAVNY  60
AQKFQGRVTI TADESTSTAY MELSSLRSED TAVYYCARDQ FIKYYDFSSG YFPNGFDIWG  120
KGTLVTVSS                                                          129

SEQ ID NO: 28           moltype = AA  length = 107
FEATURE                 Location/Qualifiers
REGION                  1..107
                        note = construct
source                  1..107
                        mol_type = protein
                        organism = synthetic construct
SEQUENCE: 28
QTVVTQPPSV SVSPGQTASI TCSGDKLGDK YAAWYQQKPG QSPVLVIYQD TVRPSGIPER  60
FSGSNSGNTA TLTISGTQAM DEADYYCQTW VSSTGVFGTG TKVTVLG                107

SEQ ID NO: 29           moltype = AA  length = 130
FEATURE                 Location/Qualifiers
REGION                  1..130
                        note = construct
source                  1..130
                        mol_type = protein
                        organism = synthetic construct
SEQUENCE: 29
EVQLVETGVE VKKPGASVKV SCKASGYTFT SYYMHWVRQA PGQGLEWMGI INPSGGSTSY  60
AQKFQGRVTM TRDTSTSTAY MELSSLRSED TAVYYCARDL GEGYDFWSGY YTPSGAFDIW  120
GKGTMVTVSS                                                         130

SEQ ID NO: 30           moltype = AA  length = 111
FEATURE                 Location/Qualifiers
REGION                  1..111
                        note = construct
source                  1..111
                        mol_type = protein
                        organism = synthetic construct
SEQUENCE: 30
QSALTQPASV SGSPGQSITI SCTGTSSDVG GYNYVSWYQQ RPGKAPKLII YDVTTRPSGV  60
SNRFSGSKSG TTASLTISGL QAEDEADYYC SSYTSYSTWV FGGGTKLTVL G           111

SEQ ID NO: 31           moltype = AA  length = 117
FEATURE                 Location/Qualifiers
REGION                  1..117
                        note = construct
source                  1..117
                        mol_type = protein
                        organism = synthetic construct
SEQUENCE: 31
QVQLQESGPG PVKPSETLSL TCAVSGGSIS SSHWWSWVRQ PPGKGLEWIG EIYHSGRTYY  60
NPSLKSRVTI SVDTSRNQFS LKLSSVTAAD TAVYYCARED GGIMDVWGQG TLVTVSS     117

SEQ ID NO: 32           moltype = AA  length = 110
FEATURE                 Location/Qualifiers
REGION                  1..110
                        note = construct
source                  1..110
                        mol_type = protein
                        organism = synthetic construct
SEQUENCE: 32
LSSELTQDPA VSVALGQTVR ITCQGDSLRR FYASWYQQKP GQAPVLVIYG KNNRPSGIPD  60
RFSASDSGNT ASLTITGAQA EDEADYYCSS RDRSGYRWVF GGGTKVTVLG             110
```

-continued

```
SEQ ID NO: 33           moltype = AA  length = 326
FEATURE                 Location/Qualifiers
REGION                  1..326
                        note = construct
source                  1..326
                        mol_type = protein
                        organism = synthetic construct
SEQUENCE: 33
ASTKGPSVFP LAPCSRSTSE STAALGCLVK DYFPEPVTVS WNSGALTSGV HTFPAVLQSS  60
GLYSLSSVVT VPSSNFGTQT YTCNVDHKPS NTKVDKTVER KCCVECPPCP APPVAGPSVF  120
LFPPKPKDTL MISRTPEVTC VVVDVSHEDP EVQFNWYVDG VEVHNAKTKP REEQFNSTFR  180
VVSVLTVVHQ DWLNGKEYKC KVSNKGLPAP IEKTISKTKG QPREPQVYTL PPSREEMTKN  240
QVSLTCLVKG FYPSDIAVEW ESNGQPENNY KTTPPMLDSD GSFFLYSKLT VDKSRWQQGN  300
VFSCSVMHEA LHNHYTQKSL SLSPGK                                     326

SEQ ID NO: 34           moltype = AA  length = 330
FEATURE                 Location/Qualifiers
REGION                  1..330
                        note = construct
source                  1..330
                        mol_type = protein
                        organism = synthetic construct
SEQUENCE: 34
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPEAAGG  120
PSVFLFPPKP KDTLMISRTP EVTCVVVAVS HEDPEVKFNW YVDGVEVHNA KTKPREEQYN  180
STYRVVSVLT VLHQDWLNGK EYKCKVSNKA LAAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                 330

SEQ ID NO: 35           moltype = AA  length = 105
FEATURE                 Location/Qualifiers
REGION                  1..105
                        note = construct
source                  1..105
                        mol_type = protein
                        organism = synthetic construct
SEQUENCE: 35
QPKAAPSVTL FPPSSEELQA NKATLVCLIS DFYPGAVTVA WKADSSPVKA GVETTTPSKQ  60
SNNKYAASSY LSLTPEQWKS HRSYSCQVTH EGSTVEKTVA PTECS                105

SEQ ID NO: 36           moltype = AA  length = 15
FEATURE                 Location/Qualifiers
REGION                  1..15
                        note = construct
source                  1..15
                        mol_type = protein
                        organism = synthetic construct
SEQUENCE: 36
GGGGSGGGGS GGGGS                                                 15

SEQ ID NO: 37           moltype = AA  length = 448
FEATURE                 Location/Qualifiers
REGION                  1..448
                        note = construct
source                  1..448
                        mol_type = protein
                        organism = synthetic construct
SEQUENCE: 37
QVQLQQWGAG LLKPSETLSL TCAVYGGSFS GYYWSWIRQS PEKGLEWIGE INHGGYVTYN  60
PSLESRVTIS VDTSKNQFSL KLSSVTAADT AVYYCARDYG PGNYDWYFDL WGRGTLVTVS  120
SASTKGPSVF PLAPCSRSTS ESTAALGCLV KDYFPEPVTV SWNSGALTSG VHTFPAVLQS  180
SGLYSLSSVV TVPSSSLGTK TYTCNVDHKP SNTKVDKRVE SKYGPPCPPC PAPEFLGGPS  240
VFLFPPKPKD TLMISRTPEV TCVVVDVSQE DPEVQFNWYV DGVEVHNAKT KPREEQFNST  300
YRVVSVLTVL HQDWLNGKEY KCKVSNKGLP SSIEKTISKA KGQPREPQVY TLPPSQEEMT  360
KNQVSLTCLV KGFYPSDIAV EWESNGQPEN NYKTTPPVLD SDGSFFLYSR LTVDKSRWQE  420
GNVFSCSVMH EALHNHYTQK SLSLSLGK                                   448

SEQ ID NO: 38           moltype = AA  length = 216
FEATURE                 Location/Qualifiers
REGION                  1..216
                        note = construct
source                  1..216
                        mol_type = protein
                        organism = synthetic construct
SEQUENCE: 38
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPPALTF CGGTKVEIKR TVAAPSVFIF  120
```

-continued

```
PPSDEQLKSG TASVVCLLNN FYPREAKVQW KVDNALQSGN SQESVTEQDS KDSTYSLSST  180
LTLSKADYEK HKVYACEVTH QGLSSPVTKS FNRGEC                            216

SEQ ID NO: 39          moltype = AA  length = 255
FEATURE                Location/Qualifiers
REGION                 1..255
                       note = construct
source                 1..255
                       mol_type = protein
                       organism = synthetic construct
SEQUENCE: 39
MGNSCYNIVA TLLLVLNFER TRSLQDPCSN CPAGTFCDNN RNQICSPCPP NSFSSAGGQR  60
TCDICRQCKG VFRTRKECSS TSNAECDCTP GFHCLGAGCS MCEQDCKQGQ ELTKKGCKDC  120
CFGTFNDQKR GICRPWTNCS LDGKSVLVNG TKERDVVCGP SPADLSPGAS SVTPPAPARE  180
PGHSPQIISF FLALTSTALL FLLFFLTLRF SVVKRGRKKL LYIFKQPFMR PVQTTQEEDG  240
CSCRFPEEEE GGCEL                                                   255

SEQ ID NO: 40          moltype = AA  length = 5
FEATURE                Location/Qualifiers
REGION                 1..5
                       note = construct
source                 1..5
                       mol_type = protein
                       organism = synthetic construct
SEQUENCE: 40
SGYWN                                                              5

SEQ ID NO: 41          moltype = AA  length = 16
FEATURE                Location/Qualifiers
REGION                 1..16
                       note = construct
source                 1..16
                       mol_type = protein
                       organism = synthetic construct
SEQUENCE: 41
YVSYTGSTYY IPSLKS                                                  16

SEQ ID NO: 42          moltype = AA  length = 11
FEATURE                Location/Qualifiers
REGION                 1..11
                       note = construct
source                 1..11
                       mol_type = protein
                       organism = synthetic construct
SEQUENCE: 42
YRDWLHGYFD Y                                                       11

SEQ ID NO: 43          moltype = AA  length = 11
FEATURE                Location/Qualifiers
REGION                 1..11
                       note = construct
source                 1..11
                       mol_type = protein
                       organism = synthetic construct
SEQUENCE: 43
KASQNVMDNV A                                                       11

SEQ ID NO: 44          moltype = AA  length = 7
FEATURE                Location/Qualifiers
REGION                 1..7
                       note = construct
source                 1..7
                       mol_type = protein
                       organism = synthetic construct
SEQUENCE: 44
SASYRFS                                                            7

SEQ ID NO: 45          moltype = AA  length = 9
FEATURE                Location/Qualifiers
REGION                 1..9
                       note = construct
source                 1..9
                       mol_type = protein
                       organism = synthetic construct
SEQUENCE: 45
QQYNGYPLT                                                          9

SEQ ID NO: 46          moltype = AA  length = 119
FEATURE                Location/Qualifiers
```

-continued

```
REGION                  1..119
                        note = construct
source                  1..119
                        mol_type = protein
                        organism = synthetic construct
SEQUENCE: 46
EVQLQESGPG LVKPSQTLSL TCTVSGDSFS SGYWNWIRQH PGKGLEYIGY VSYTGSTYYI  60
PSLKSRVTIS RDTSKNQFSL KLSSVTAADT AVYYCAGYRD WLHGYFDYWG QGTTVTVSS   119

SEQ ID NO: 47           moltype = AA  length = 107
FEATURE                 Location/Qualifiers
REGION                  1..107
                        note = construct
source                  1..107
                        mol_type = protein
                        organism = synthetic construct
SEQUENCE: 47
DIQMTQSPSS LSASVGDRVT ITCKASQNVM DNVAWYQQKP GKAPKRLIYS ASYRFSGVPS  60
RFSGSGSGTE FTLTISSLQP EDFATYYCQQ YNGYPLTFGQ GTKLEIK              107

SEQ ID NO: 48           moltype = AA  length = 704
FEATURE                 Location/Qualifiers
REGION                  1..704
                        note = construct
source                  1..704
                        mol_type = protein
                        organism = synthetic construct
SEQUENCE: 48
QVQLQESGGG LVQPGGSLRL SCAVSGFTFS SYAMHWVRQA PGKCLEWVAV ISYDGSKKWY  60
ADSVKGRFTI SRDNSKNTLY LQMNSLRAED TAVYYCARNQ GSGSYLYYYY MDVWGKGTTV  120
TVSSGSSSSG SSSSGSSSSQ SALTQPRSVS GSPGQSVTIS CTGTSSDVGG YNYVSWYQQL  180
PGKAPKVIIY EVSNRPSGVS NRFSGSKSGN TASLTISGVQ SEDEADYYCS SYTSSSTFYV  240
FGCGTQLTVL GGGGSEVQLQ ESGPGLVKPS QTLSLTCTVS GDSFSSGYWN WIRQHPGKGL  300
EYIGYVSYTG STYYIPSLKS RVTISRDTSK NQFSLKLSSV TAADTAVYYC AGYRDWLHGY  360
FDYWGQGTTV TVSSASTKGP SVFPLAPSSK STSGGTAALG CLVKDYFPEP VTVSWNSGAL  420
TSGVHTFPAV LQSSGLYSLS SVVTVPSSSL GTQTYICNVN HKPSNTKVDK KVEPKSCDKT  480
HTCPPCPAPE AAGGPSVFLF PPKPKDTLMI SRTPEVTCVV VAVSHEDPEV KFNWYVDGVE  540
VHNAKTKPRE EQYNSTYRVV SVLTVLHQDW LNGKEYKCKV SNKALAAPIE KTISKAKGQP  600
REPQVYTLPP SRDELTKNQV SLTCLVKGFY PSDIAVEWES NGQPENNYKT TPPVLDSDGS  660
FFLYSKLTVD KSRWQQGNVF SCSVMHEALH NHYTQKSLSL SPGK                 704

SEQ ID NO: 49           moltype = AA  length = 214
FEATURE                 Location/Qualifiers
REGION                  1..214
                        note = construct
source                  1..214
                        mol_type = protein
                        organism = synthetic construct
SEQUENCE: 49
DIQMTQSPSS LSASVGDRVT ITCKASQNVM DNVAWYQQKP GKAPKRLIYS ASYRFSGVPS  60
RFSGSGSGTE FTLTISSLQP EDFATYYCQQ YNGYPLTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                           214

SEQ ID NO: 50           moltype = AA  length = 714
FEATURE                 Location/Qualifiers
REGION                  1..714
                        note = construct
source                  1..714
                        mol_type = protein
                        organism = synthetic construct
SEQUENCE: 50
EVQLQESGPG LVKPSQTLSL TCTVSGDSFS SGYWNWIRQH PGKGLEYIGY VSYTGSTYYI  60
PSLKSRVTIS RDTSKNQFSL KLSSVTAADT AVYYCAGYRD WLHGYFDYWG QGTTVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPEAAGGP  240
SVFLFPPKPK DTLMISRTPE VTCVVVAVSH EDPEVKFNWY VDGVEVHNAK TKPREEQYNS  300
TYRVVSVLTV LHQDWLNGKE YKCKVSNKAL AAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKG GGGSGGGGSG GGGSQVQLQE SGGGLVQPGG  480
SLRLSCAVSG FTFSSYAMHW VRQAPGKCLE WVAVISYDGS KKWYADSVKG RFTISRDNSK  540
NTLYLQMNSL RAEDTAVYYC ARNQGSGSYL YYYYMDVWGK GTTVTVSSGS SSSGSSSSGS  600
SSSQSALTQP RSVSGSPGQS VTISCTGTSS DVGGYNYVSW YQQLPGKAPK VIIYEVSNRP  660
SGVSNRFSGS KSGNTASLTI SGVQSEDEAD YYCSSYTSSS TFYVFGCGTQ LTVL       714

SEQ ID NO: 51           moltype = AA  length = 15
FEATURE                 Location/Qualifiers
REGION                  1..15
                        note = construct
```

```
source                 1..15
                       mol_type = protein
                       organism = synthetic construct
SEQUENCE: 51
GSSSSGSSSS GSSSS                                                    15

SEQ ID NO: 52          moltype = AA  length = 5
FEATURE                Location/Qualifiers
REPEAT                 1..5
                       note = construct
source                 1..5
                       mol_type = protein
                       organism = synthetic construct
SEQUENCE: 52
GGGGS                                                               5

SEQ ID NO: 53          moltype = DNA  length = 15
FEATURE                Location/Qualifiers
misc_feature           1..15
                       note = construct
source                 1..15
                       mol_type = other DNA
                       organism = synthetic construct
SEQUENCE: 53
tccggctact ggaac                                                    15

SEQ ID NO: 54          moltype = DNA  length = 48
FEATURE                Location/Qualifiers
misc_feature           1..48
                       note = construct
source                 1..48
                       mol_type = other DNA
                       organism = synthetic construct
SEQUENCE: 54
tacgtgtcct acaccggctc tacctactac atccccagcc tgaagtcc                48

SEQ ID NO: 55          moltype = DNA  length = 33
FEATURE                Location/Qualifiers
misc_feature           1..33
                       note = construct
source                 1..33
                       mol_type = other DNA
                       organism = synthetic construct
SEQUENCE: 55
tacagagatt ggctgcacgg ctacttcgac tac                                33

SEQ ID NO: 56          moltype = DNA  length = 33
FEATURE                Location/Qualifiers
misc_feature           1..33
                       note = construct
source                 1..33
                       mol_type = other DNA
                       organism = synthetic construct
SEQUENCE: 56
aaggccagcc agaacgtgat ggacaacgtg gcc                                33

SEQ ID NO: 57          moltype = DNA  length = 21
FEATURE                Location/Qualifiers
misc_feature           1..21
                       note = construct
source                 1..21
                       mol_type = other DNA
                       organism = synthetic construct
SEQUENCE: 57
tccgcctcct acagattctc t                                             21

SEQ ID NO: 58          moltype = DNA  length = 27
FEATURE                Location/Qualifiers
misc_feature           1..27
                       note = construct
source                 1..27
                       mol_type = other DNA
                       organism = synthetic construct
SEQUENCE: 58
cagcagtaca acggctaccc tctgacc                                       27

SEQ ID NO: 59          moltype = DNA  length = 357
FEATURE                Location/Qualifiers
misc_feature           1..357
```

```
                        note = construct
source                  1..357
                        mol_type = other DNA
                        organism = synthetic construct
SEQUENCE: 59
gaggtccagc tgcaagaatc tggccctgga ctggtcaagc cctctcagac cctgtctctg  60
acctgtaccg tgtccggcga ctccttctct tccggctact ggaactggat cagacagcac  120
cctggcaagg gcctcgagta catcggctac gtgtcctaca ccggctctac ctactacatc  180
cccagcctga agtccagagt gaccatctct cgggacacct ccaagaacca gttctccctg  240
aagctgtcct ccgtgaccgc tgctgatacc gccgtgtact actgtgccgg ctacagagat  300
tggctgcacg gctacttcga ctactggggc cagggcacaa cagtgaccgt ttcttct     357

SEQ ID NO: 60           moltype = DNA  length = 321
FEATURE                 Location/Qualifiers
misc_feature            1..321
                        note = construct
source                  1..321
                        mol_type = other DNA
                        organism = synthetic construct
SEQUENCE: 60
gacatccaga tgacccagtc tccatcctct ctgtccgcct ctgtgggcga cagagtgacc  60
atcacatgca aggccagcca gaacgtgatg gacaacgtgg cctggtatca gcagaagcct  120
ggcaaggccc ctaagcggct gatctactcc gcctcctaca gattctctgg cgtgccctct  180
agattctccg gctctggctc tggcaccgag tttaccctga caatctccag cctgcagcct  240
gaggacttcg ccacctacta ctgccagcag tacaacggct accctctgac ctttggccag  300
ggcaccaagc tggaaatcaa g                                            321

SEQ ID NO: 61           moltype = AA  length = 290
FEATURE                 Location/Qualifiers
REGION                  1..290
                        note = construct
source                  1..290
                        mol_type = protein
                        organism = synthetic construct
SEQUENCE: 61
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET             290

SEQ ID NO: 62           moltype = DNA  length = 870
FEATURE                 Location/Qualifiers
misc_feature            1..870
                        note = construct
source                  1..870
                        mol_type = other DNA
                        organism = synthetic construct
SEQUENCE: 62
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggactcac  720
ttggtaattc tgggagccat cttattatgc cttggtgtag cactgacatt catcttccgt  780
ttaagaaaag ggagaatgat ggatgtgaaa aaatgtggca tccaagatac aaactcaaag  840
aagcaaagtg atacacattt ggaggagacg                                   870

SEQ ID NO: 63           moltype = AA  length = 107
FEATURE                 Location/Qualifiers
REGION                  1..107
                        note = construct
source                  1..107
                        mol_type = protein
                        organism = synthetic construct
SEQUENCE: 63
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 64           moltype = DNA  length = 321
FEATURE                 Location/Qualifiers
misc_feature            1..321
```

-continued

```
                        note = construct
source                  1..321
                        mol_type = other DNA
                        organism = synthetic construct
SEQUENCE: 64
cggacggtgg ctgcaccatc tgtcttcatc ttcccgccat ctgatgagca gttgaaatct  60
ggaactgcct ctgttgtgtg cctgctgaat aacttctacc ccagagaagc caaagtgcag  120
tggaaggtgg acaacgccct gcagagcgga aacagccagg aaagcgtgac agagcaggat  180
tccaaggatt ccacatacag cctgagcagc acactgacac tgtccaaggc cgactacgag  240
aagcacaagg tgtacgcctg cgaagtgaca caccagggac tgtcctcccc tgtgacaaag  300
agcttcaaca gaggagaatg c                                            321

SEQ ID NO: 65           moltype = DNA  length = 2112
FEATURE                 Location/Qualifiers
misc_feature            1..2112
                        note = construct
source                  1..2112
                        mol_type = other DNA
                        organism = synthetic construct
SEQUENCE: 65
caggtgcagc tgcaggagtc cggaggagga ctggtgcagc caggaggctc cctgaggctg  60
agctgcgccg tgtctggctt caccttttcc agctacgcca tgcactgggt gagacaggct  120
cctggcaagt gcctggagtg ggtggccgtg atctcctacg acggcagcaa gaagtggtat  180
gctgatagcg tgaagggcag gttcaccatc tctcgggaca actccaagaa tacactgtac  240
ctgcagatga actctctgag agccgaggat accgccgtgt actattgtgc tcgcaatcag  300
ggcagcggct cttatctgta ctattactat atggacgtgt ggggcaaggg caccacagtg  360
acagtgtctt ccggctcctc cagctctggc agttctagct ctggctctag ctccagccag  420
tccgccctga cccagcctag gtccgtgtcc ggaagccctg gccagtccgt gaccatctcc  480
tgtacaggca cctcctccga cgtgggcggc tacaactacg tgagctggta ccagcagctg  540
cccggcaagg ctcccaaggt gatcatctac gaggtgtcca acaggccctc cggcgtgtcc  600
aataggttca gcggctccaa gtccggaaac accgcctccc tgaccatcag cggcgtgcag  660
tccgaggatg aggccgacta ctactgctcc tcctacacct ccagctccac cttctacgtg  720
ttcggctgcg gcacccagct gaccgtgctg ggtggcggag gatctgaggt ccagctgcaa  780
gaatctggcc ctggactggt caagccctct cagaccctgt ctctgacctg taccgtgtcc  840
ggcgactcct tctcttccgg ctactggaac tggatcagac agcaccctgg caagggcctc  900
gagtacatcg gctacgtgtc ctacaccggc tctacctact acatccccag cctgaagtcc  960
agagtgacca tctctcggga cacctccaag aaccagttct ccctgaagct gtcctccgtg  1020
accgctgctg ataccgccgt gtactactgt gccggctaca gagattggct gcacggctac  1080
ttcgactact ggggccaggg cacaacagtg accgtttctt ctgccagcac caagggacca  1140
tccgtgttcc cactggcccc ctccagcaag tccaccagcg gaggaacagc cgctctggga  1200
tgcctggtga aggactactt cccagagccc gtgacagtga gctggaactc tggcgccctg  1260
accagcggag tgcacacatt tcccgccgtg ctccagtctt ccggcctgta ctctctgagc  1320
tctgtggtga ccgtgccctc cagctctctg ggcacccaga catatatctg caacgtgaat  1380
cacaagccaa gcaatacaaa ggtggacaag aaggtggagc ccaagtcttg tgataagacc  1440
catacatgcc ccccttgtcc tgctccagag gctgctggag gaccaagcgt gttcctgttt  1500
ccacccaagc ctaaggacac cctgatgatc tccaggaccc ccgaggtgac atgcgtggtg  1560
gtggctgtga gccacgagga ccccgaggtg aagtttaact ggtacgtgga tggcgtggag  1620
gtgcataatg ctaagaccaa gcctagggag gagcagtaca actctaccta tcgggtggtg  1680
tccgtgctga cagtgctgca ccaggactgg ctgaacggca aggagtataa gtgcaaggtg  1740
tctaataagg ccctggctgc tcctatcgag aagaccatct ccaaggccaa gggccagcct  1800
agagagccac aggtgtacac actgcctcca tctcgcgacg agctgaccaa gaaccaggtg  1860
tccctgacat gtctggtgaa gggcttctat ccttccgaca tcgctgtgga gtgggagagc  1920
aacggccagc cagagaacaa ttacaagacc acaccccctg tgctggactc cgatggcagc  1980
ttctttctgt atagcaagct gaccgtggat aagtccaggt ggcagcaggg caacgtgttt  2040
tcttgctccg tgatgcatga ggctctgcac aatcattata cacagaagag cctgtctctg  2100
tcccctggca ag                                                      2112

SEQ ID NO: 66           moltype = DNA  length = 2142
FEATURE                 Location/Qualifiers
misc_feature            1..2142
                        note = construct
source                  1..2142
                        mol_type = other DNA
                        organism = synthetic construct
SEQUENCE: 66
gaggtccagc tgcaagaatc tggccctgga ctggtcaagc cctctcagac cctgtctctg  60
acctgtaccg tgtccggcga ctccttctct tccggctact ggaactggat cagacagcac  120
cctggcaagg gcctcgagta catcggctac gtgtcctaca ccggctctac ctactacatc  180
cccagcctga agtccagagt gaccatctct cgggacacct ccaagaacca gttctccctg  240
aagctgtcct ccgtgaccgc tgctgatacc gccgtgtact actgtgccgg ctacagagat  300
tggctgcacg gctacttcga ctactggggc cagggcacaa cagtgaccgt ttcttctgcc  360
agcaccaagg gaccatccgt gttcccactg gccccctcca gcaagtccac cagcggagga  420
acagccgctc tgggatgcct ggtgaaggac tacttcccag agcccgtgac agtgagctgg  480
aactctggcg ccctgaccag cggagtgcac acatttcccg ccgtgctcca gtcttccggc  540
ctgtactctc tgagctctgt ggtgaccgtg ccctccagct ctctgggcac ccagacatat  600
atctgcaacg tgaatcacaa gccaagcaat acaaaggtgg acaagaaggt ggagcccaag  660
tcttgtgata agacccatac atgcccccct tgtcctgctc cagaggctgc tggaggacca  720
agcgtgttcc tgtttccacc caagcctaag gacaccctga tgatctccag gacccccgag  780
gtgacatgcg tggtggtggc tgtgagccac gaggaccccg aggtgaagtt taactggtac  840
```

-continued

```
gtggatggcg tggaggtgca taatgctaag accaagccta gggaggagca gtacaactct  900
acctatcggg tggtgtccgt gctgacagtg ctgcaccagg actggctgaa cggcaaggag  960
tataagtgca aggtgtctaa taaggccctg gctgctccta tcgagaagac catctccaag  1020
gccaagggcc agcctagaga gccacaggtg tacacactgc ctccatctcg cgacgagctg  1080
accaagaacc aggtgtccct gacatgtctg gtgaagggct tctatccttc cgacatcgct  1140
gtggagtggg agagcaacgg ccagccagag aacaattaca agaccacacc ccctgtgctg  1200
gactccgatg gcagcttctt tctgtatagc aagctgaccg tggataagtc caggtggcag  1260
cagggcaacg tgttttcttg ctccgtgatg catgaggctc tgcacaatca ttatacacag  1320
aagagcctgt ctctgtcccc tggcaagggt ggcggaggat ctggcggagg cggaagtggc  1380
ggtggcggtt cacaggtgca gctgcaggag tccggaggag gactggtgca gccaggaggc  1440
tccctgaggc tgagctgcgc cgtgtctggc ttcacctttt ccagctacgc catgcactgg  1500
gtgagacagg ctcctggcaa gtgcctggag tgggtggccg tgatctccta cgacggcagc  1560
aagaagtggt atgctgatag cgtgaagggc aggttcacca tctctcggga caactccaag  1620
aatacactgt acctgcagat gaactctctg agagccgagg ataccgccgt gtactattgt  1680
gctcgcaatc agggcagcgg ctcttatctg tactattact atatggacgt gtggggcaag  1740
ggcaccacag tgacagtgtc ttccggctcc tccagctctg gcagttctag ctctggctct  1800
agctccagcc agtccgccct gacccagcct aggtccgtgt ccggaagccc tggccagtcc  1860
gtgaccatct cctgtacagg cacctcctcc gacgtgggcg gctacaacta cgtgagctgg  1920
taccagcagc tgcccggcaa ggctcccaag gtgatcatct acgaggtgtc caacaggccc  1980
tccggcgtgt ccaataggtt cagcggctcc aagtccggaa acaccgcctc cctgaccatc  2040
agcggcgtgc agtccgagga tgaggccgac tactactgct cctcctacac ctccagctcc  2100
accttctacg tgttcggctg cggcacccag ctgaccgtgc tg                    2142

SEQ ID NO: 67          moltype = DNA  length = 15
FEATURE                Location/Qualifiers
misc_feature           1..15
                       note = construct
source                 1..15
                       mol_type = other DNA
                       organism = synthetic construct
SEQUENCE: 67
agctacgcca tgcac                                                   15

SEQ ID NO: 68          moltype = DNA  length = 42
FEATURE                Location/Qualifiers
misc_feature           1..42
                       note = construct
source                 1..42
                       mol_type = other DNA
                       organism = synthetic construct
SEQUENCE: 68
tacgacggca gcaagaagtg gtatgctgat agcgtgaagg gc                     42

SEQ ID NO: 69          moltype = DNA  length = 45
FEATURE                Location/Qualifiers
misc_feature           1..45
                       note = construct
source                 1..45
                       mol_type = other DNA
                       organism = synthetic construct
SEQUENCE: 69
aatcagggca gcggctctta tctgtactat tactatatgg acgtg                  45

SEQ ID NO: 70          moltype = DNA  length = 42
FEATURE                Location/Qualifiers
misc_feature           1..42
                       note = construct
source                 1..42
                       mol_type = other DNA
                       organism = synthetic construct
SEQUENCE: 70
acaggcacct cctccgacgt gggcggctac aactacgtga gc                     42

SEQ ID NO: 71          moltype = DNA  length = 21
FEATURE                Location/Qualifiers
misc_feature           1..21
                       note = construct
source                 1..21
                       mol_type = other DNA
                       organism = synthetic construct
SEQUENCE: 71
gaggtgtcca acaggccctc c                                            21

SEQ ID NO: 72          moltype = DNA  length = 33
FEATURE                Location/Qualifiers
misc_feature           1..33
                       note = construct
source                 1..33
                       mol_type = other DNA
```

-continued

```
                         organism = synthetic construct
SEQUENCE: 72
tcctcctaca cctccagctc caccttctac gtg                              33

SEQ ID NO: 73            moltype = DNA  length = 372
FEATURE                  Location/Qualifiers
misc_feature             1..372
                         note = construct
source                   1..372
                         mol_type = other DNA
                         organism = synthetic construct
SEQUENCE: 73
caggtgcagc tgcaggagtc cggaggagga ctggtgcagc caggaggctc cctgaggctg  60
agctgcgccg tgtctggctt caccttttcc agctacgcca tgcactgggt gagacaggct  120
cctggcaagg gactggagtg ggtggccgtg atctcctacg acggcagcaa gaagtggtat  180
gctgatagcg tgaagggcag gttcaccatc tctcgggaca actccaagaa tacactgtac  240
ctgcagatga actctctgag agccgaggat accgccgtgt actattgtgc tcgcaatcag  300
ggcagcggct cttatctgta ctattactat atggacgtgt ggggcaaggg caccacagtg  360
acagtgtctt cc                                                      372

SEQ ID NO: 74            moltype = DNA  length = 333
FEATURE                  Location/Qualifiers
misc_feature             1..333
                         note = construct
source                   1..333
                         mol_type = other DNA
                         organism = synthetic construct
SEQUENCE: 74
caaagcgccc tgacccagcc taggtccgtg tccggaagcc ctggccagtc cgtgaccatc  60
tcctgtacag gcacctcctc cgacgtgggc ggctacaact acgtgagctg gtaccagcag  120
ctgcccggca aggctcccaa ggtgatcatc tacgaggtgt ccaacaggcc ctccggcgtg  180
tccaataggt tcagcggctc caagtccgga aacaccgcct ccctgaccat cagcggcgtg  240
cagtccgagg atgaggccga ctactactgc tcctcctaca cctccagctc caccttctac  300
gtgttcggca ccggcaccca gctgaccgtg ctg                               333

SEQ ID NO: 75            moltype = AA  length = 327
FEATURE                  Location/Qualifiers
REGION                   1..327
                         note = construct
source                   1..327
                         mol_type = protein
                         organism = synthetic construct
SEQUENCE: 75
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                      327

SEQ ID NO: 76            moltype = DNA  length = 642
FEATURE                  Location/Qualifiers
misc_feature             1..642
                         note = construct
source                   1..642
                         mol_type = other DNA
                         organism = synthetic construct
SEQUENCE: 76
gacatccaga tgacccagtc tccatcctct ctgtccgcct ctgtgggcga cagagtgacc  60
atcacatgca aggccagcca gaacgtgatg gacaacgtgg cctggtatca gcagaagcct  120
ggcaaggccc ctaagcggct gatctactcc gcctcctaca gattctctgg cgtgccctct  180
agattctccg gctctggctc tggcaccgag tttaccctga caatctccag cctgcagcct  240
gaggacttcg ccacctacta ctgccagcag tacaacggct accctctgac ctttggccag  300
ggcaccaagc tggaaatcaa gcggacggtg gctgcaccat ctgtcttcat cttcccgcca  360
tctgatgagc agttgaaatc tggaactgcc tctgttgtgt gcctgctgaa taacttctac  420
cccagagaag ccaaagtgca gtggaaggtg gacaacgccc tgcagagcgg aaacagccag  480
gaaagcgtga cagagcagga ttccaaggat tccacataca gcctgagcag cacactgaca  540
ctgtccaagg ccgactacga gaagcacaag gtgtacgcct gcgaagtgac acaccaggga  600
ctgtcctccc ctgtgacaaa gagcttcaac agaggagaat gc                      642

SEQ ID NO: 77            moltype = AA  length = 124
FEATURE                  Location/Qualifiers
REGION                   1..124
                         note = construct
source                   1..124
                         mol_type = protein
                         organism = synthetic construct
SEQUENCE: 77
QVQLQESGGG LVQPGGSLRL SCAVSGFTFS SYAMHWVRQA PGKCLEWVAV ISYDGSKKWY  60
```

-continued

```
ADSVKGRFTI SRDNSKNTLY LQMNSLRAED TAVYYCARNQ GSGSYLYYYY MDVWGKGTTV  120
TVSS                                                               124

SEQ ID NO: 78          moltype = AA  length = 111
FEATURE                Location/Qualifiers
REGION                 1..111
                       note = construct
source                 1..111
                       mol_type = protein
                       organism = synthetic construct
SEQUENCE: 78
QSALTQPRSV SGSPGQSVTI SCTGTSSDVG GYNYVSWYQQ LPGKAPKVII YEVSNRPSGV  60
SNRFSGSKSG NTASLTISGV QSEDEADYYC SSYTSSSTFY VFGCGTQLTV L           111

SEQ ID NO: 79          moltype = DNA  length = 372
FEATURE                Location/Qualifiers
misc_feature           1..372
                       note = construct
source                 1..372
                       mol_type = other DNA
                       organism = synthetic construct
SEQUENCE: 79
caggtgcagc tgcaggagtc cggaggagga ctggtgcagc caggaggctc cctgaggctg  60
agctgcgccg tgtctggctt caccttttcc agctacgcca tgcactgggt gagacaggct  120
cctggcaagt gcctggagtg ggtggccgtg atctcctacg acggcagcaa gaagtggtat  180
gctgatagcg tgaagggcag gttcaccatc tctcgggaca actccaagaa tacactgtac  240
ctgcagatga actctctgag agccgaggat accgccgtgt actattgtgc tcgcaatcag  300
ggcagcggct cttatctgta ctattactat atggacgtgt ggggcaaggg caccacagtg  360
acagtgtctt cc                                                      372

SEQ ID NO: 80          moltype = DNA  length = 333
FEATURE                Location/Qualifiers
misc_feature           1..333
                       note = construct
source                 1..333
                       mol_type = other DNA
                       organism = synthetic construct
SEQUENCE: 80
cagtccgccc tgacccagcc taggtccgtg tccggaagcc ctggccagtc cgtgaccatc  60
tcctgtacag gcacctcctc cgacgtgggc ggctacaact acgtgagctg gtaccagcag  120
ctgcccggca aggctcccaa ggtgatcatc tacgaggtgt ccaacaggcc ctccggcgtg  180
tccaataggt tcagcggctc caagtccgga aacaccgcct ccctgaccat cagcggcgtg  240
cagtccgagg atgaggccga ctactactgc tcctcctaca cctccagctc caccttctac  300
gtgttcggct gcggcaccca gctgaccgtg ctg                               333

SEQ ID NO: 81          moltype = AA  length = 395
FEATURE                Location/Qualifiers
REGION                 1..395
                       note = construct
source                 1..395
                       mol_type = protein
                       organism = synthetic construct
SEQUENCE: 81
LQDPCSNCPA GTFCDNNRNQ ICSPCPPNSF SSAGGQRTCD ICRQCKGVFR TRKECSSTSN  60
AECDCTPGFH CLGAGCSMCE QDCKQGQELT KKGCKDCCFG TFNDQKRGIC RPWTNCSLDG  120
KSVLVNGTKE RDVVCGPSPA DLSPGASSVT PPAPAREPGH SPQEPKSCDK THTCPPCPAP  180
ELLGGPSVFL FPPKPKDTLM ISRTPEVTCV VVDVSHEDPE VKFNWYVDGV EVHNAKTKPR  240
EEQYNSTYRV VSVLTVLHQD WLNGKEYKCK VSNKALPAPI EKTISKAKGQ PREPQVYTLP  300
PSREEMTKNQ VSLTCLVKGF YPSDIAVEWE SNGQPENNYK TTPPVLDSDG SFFLYSKLTV  360
DKSRWQQGNV FSCSVMHEAL HNHYTQKSLS LSPGK                             395

SEQ ID NO: 82          moltype = AA  length = 446
FEATURE                Location/Qualifiers
REGION                 1..446
                       note = construct
source                 1..446
                       mol_type = protein
                       organism = synthetic construct
SEQUENCE: 82
QVQLVESGGG AVQPGRSLRL SCAASGFTFS SYGMHWVRQA PGKGLEWVAV ILYDGSDKFY  60
ADSVKGRFTI SRDNSKNTLY LQMNSLRAED TAVYYCAKVA VAGTHFDYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLGK                                       446

SEQ ID NO: 83          moltype = AA  length = 214
```

-continued

```
FEATURE                 Location/Qualifiers
REGION                  1..214
                        note = construct
source                  1..214
                        mol_type = protein
                        organism = synthetic construct
SEQUENCE: 83
DIQMTQSPSS LSASVGDRVT ITCRASQGIR NDLGWYQQKP GKAPKLLIYA ASSLQSGVPS  60
RFSGSGSGTD FTLTISSLQP EDFATYYCQQ LNSYPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 84           moltype = AA  length = 466
FEATURE                 Location/Qualifiers
REGION                  1..466
                        note = construct
source                  1..466
                        mol_type = protein
                        organism = synthetic construct
SEQUENCE: 84
EVQLLESGGG EVQPGGSLRL SCAASGGIFA IKPISWYRQA PGKQREWVST TTSSGATNYA  60
ESVKGRFTIS RDNAKNTLYL QMSSLRAEDT AVYYCNVFEY WGQGTLVTVK PGGSGGSEVQ  120
LLESGGGEVQ PGGSLRLSCA ASGFSFSINA MGWYRQAPGK RREFVAAIES GRNTVYAESV  180
KGRFTISRDN AKNTVYLQMS SLRAEDTAVY YCGLLKGNRV VSPSVAYWGQ GTLVTVKPGG  240
GGDKTHTCPP CPAPGGPSVF LFPPKPKDTL MISRTPEVTC VVVDVSHEDP EVKFNWYVDG  300
VEVHNAKTKP REEQYNSTYR VVSVLTVLHQ DWLNGKEYKC KVSNKALPAP IEKTISKAKG  360
QPREPQVYTL PPSRDELTKN QVSLTCLVKG FYPSDIAVEW ESNGQPENNY KTTPPVLDSD  420
GSFFLYSKLT VDKSRWQQGN VFSCSVMHEA LHNHYTQKSL SLSPGK                 466

SEQ ID NO: 85           moltype = DNA  length = 990
FEATURE                 Location/Qualifiers
misc_feature            1..990
                        note = construct
source                  1..990
                        mol_type = other DNA
                        organism = synthetic construct
SEQUENCE: 85
gccagcacca agggaccatc cgtgttccca ctggccccct ccagcaagtc caccagcgga  60
ggaacagccg ctctgggatg cctggtgaag gactacttcc cagagcccgt gacagtgagc  120
tggaactctg gcgccctgac cagcggagtg cacacatttc ccgccgtgct ccagtcttcc  180
ggcctgtact ctctgagctc tgtggtgacc gtgccctcca gctctctggg cacccagaca  240
tatatctgca acgtgaatca caagccaagc aatacaaagg tggacaagaa ggtggagccc  300
aagtcttgtg ataagaccca tacatgcccc ccttgtcctg ctccagaggc tgctggagga  360
ccaagcgtgt tcctgtttcc acccaagcct aaggacaccc tgatgatctc caggaccccc  420
gaggtgacat gcgtggtggt ggctgtgagc cacgaggacc ccgaggtgaa gtttaactgg  480
tacgtggatg gcgtggaggt gcataatgct aagaccaagc ctagggagga gcagtacaac  540
tctacctatc gggtggtgtc cgtgctgaca gtgctgcacc aggactggct gaacggcaag  600
gagtataagt gcaaggtgtc taataaggcc ctggctgctc ctatcgagaa gaccatctcc  660
aaggccaagg gccagcctag agagccacag gtgtacacac tgcctccatc tcgcgacgag  720
ctgaccaaga accaggtgtc cctgacatgt ctggtgaagg gcttctatcc ttccgacatc  780
gctgtggagt gggagagcaa cggccagcca gagaacaatt acaagaccac acccccctgtg  840
ctggactccg atggcagctt ctttctgtat agcaagctga ccgtggataa gtccaggtgg  900
cagcagggca acgtgttttc ttgctccgtg atgcatgagg ctctgcacaa tcattataca  960
cagaagagcc tgtctctgtc ccctggcaag                                   990
```

ANTIBODIES BINDING 4-1BB AND USES THEREOF

CROSS-REFERENCE TO RELATED APPLICATIONS

This application is a Divisional Application of application Ser. No. 17/038,669, filed Sep. 30, 2020, which claims priority to U.S. Provisional Application No. 62/913,744, filed Oct. 11, 2019, which applications are fully incorporated herein by reference in their entirety.

REFERENCE TO AN ELECTRONIC SEQUENCE LISTING

The contents of the electronic sequence listing (N064070000US01-SEQ-JDH.xml; Size: 122,314 bytes; and Date of Creation: Feb. 24, 2023 is herein incorporated by reference in its entirety.

FIELD OF THE INVENTION

The present disclosure relates generally to an isolated monoclonal antibody, particularly a human monoclonal antibody, or the antigen-binding portion thereof, that specifically binds to human 4-1BB with functionality. A nucleic acid molecule encoding the antibody or the antigen-binding portion thereof, an expression vector, a host cell and a method for expressing the antibody or the antigen-binding portion thereof are also provided. The present disclosure further provides a bispecific molecule. Moreover, the present disclosure further provides a pharmaceutical composition comprising the antibody or the antigen-binding portion thereof, as well as a treatment method using the antibody or the antigen-binding portion thereof of the disclosure.

BACKGROUND OF THE INVENTION 4-1BB, also referred to as CD137 or TNFRSF9, is a member of the tumor necrosis factor receptor family. It is best characterized as a co-stimulatory molecule on T cell surface that modulates TCR-induced T cell activation. Upon engaged by 4-1BBL, its major natural ligand expressed on activated antigen presenting cells, 4-1BB upregulates antiapoptotic molecules, and promotes cytokine production and effector function. 4-1BB is also found on dendritic cells, activated monocytes, NK cells, neutrophils, eosinophils, and mast cells, and 4-1BB signaling is reported to stimulate IFN-γ secretion and promote NK cell proliferation and DC activation (Cariad Chester et al., (2018) *Blood* 131(1): 49-57).

On the other hand, 4-1BB expression is observed on tumor cells and in the sera of cancer patients. 4-1BB expression along blood vessel walls at the inflammation sites, mainly within tumor microvasculature and atherosclerotic areas, suggests it may mediate leukocyte migration (Drenkard D et al., (2007) *FASEB J.* 21(2): 456-463). Further, ligating 4-1BB on T regulatory cells (Treg) may induce Treg proliferation (Zhang P et al., (2007) *Scand J Immunol.* 66(4): 435-440).

To look into 4-1BB's complicated functions, Melero et al., tested in 1997 the effect of an agonistic anti-4-1BB antibody on poorly immunogenic Ag104A sarcoma and highly immunogenic P815 mastocytoma, and unvealed 4-1BB agonist's anti-tumor activity (Melero I et al., (1997) *Nature Med.* 3(6): 682-685). Later on it was reported that about 60% of 12-month old 4-1BBL$^{-/-}$ mice developed B cell lymphomas, and 4-1BBL$^{-/-}$ mice had reduced NK cell numbers and activity (Middendorp S et al., (2009) *Blood* 114(1): 2280-2289; Vinay D. S. et al., (2004) *J. Immunol.* 173(6): 4218.4229). Injection of B16.F10 melanoma cells caused more death in 4-1BB$^{-/-}$ mice but not in 4-1BB$^{+/+}$ mice (Ju S. A et al., (2005) *Immunol. Cell Biol.* 83(4): 344-351). With these discoveries, 4-1BB has emerged as a strong immune system activator and a candidate immunotherapeutic target. Studies have shown that a 4-1BB agonist may be used to treat tumors, viral infections and autoimmune diseases, and to increase graft survival (Seo S. K et al., (2004) *Nature Med.* 10(10):1088-1094; Sun Y et al., (2002) *J. Immunol.* 168(3):1457-1465; Agarwal A et al., (2008) *Curr. Opin. Organ. Transplant* 13(4):366-372).

Particularly, the effect of 4-1BB is far more investigated in cancer than in other pathological conditions. 4-1BB signaling is found to break and reverse established anergy in cytotoxic T lymphocytes. For example, in the B16.SIY melanoma model, administration of anti-4-1BB mAbs restored the function of CD8+ TILs that had lost the IL-2 secretion capacities (Cariad Chester et al., (2018) supra). Although most of the anti-tumor effects of the anti-4-1BB mAbs are indicated by CD8+ T cells. NK, NKT cells, dendritical cells and CD4+ T cells have been proved to be critical and necessary too for tumor treatment (Dass S. V et al., (2014) *BMB Rep.* 47(3): 122-129). Further, upregulation of some adhesion molecules such as ICAM-1 and CXAM-1, following anti-4-1BB administration, is found to increase T cell migration into tumor site (Palazon A et al., (2011) *Cancer Res.* 71(3): 801-811). More importantly, the efficacy of the anti-4-1BB therapy has also been demonstrated in other solid tumor and lymphoma prelimical models, such as follicular lymphoma, diffuse large B-cell lymphoma, melanoma, ovarian cancer, and squamous lung cancer (Cariad Chester et al., (2018) supra).

Urelumab, a fully human IgG4 monoclonal antibody developed by BMS, was the first anti-4-1BB therapeutic to enter clinical trials. It specifically binds to and activates 4-1B8-expressing immune cells and has shown encouraging efficacy in phase 1 and 2 monotherapy trials, but with liver toxicity in a dose dependent manner. The monotherapy of and the combination therapy with Urelumab at a tolerated dose resulted in limited anti-tumor effect although demonstrated a promising immune-stimulatory pharmacodynamics effect. Utomilumab, a humanized IgG2 monoclonal antibody of Pfizer, has showed a superior safety profile, but is a weaker 4-188 agonist as compared to Urelumab. It is now being studied in clinical trials in combination with Rituximab, Pembrolizumab. Keytruda, Avelumab and some other anti-tumor antibodies for treating various cancers (Cariad Chester et al., (2018) supra).

Moreover, combination therapy of anti-4-1BB and other antibodies (such as anti-PD-1 antibodies) are also under clinical trials. For example, there is a need for bispecific antibodies that can simultaneously target both PD-L1 and 4-1BB which would block the PD-1/PD-L1 pathway and provide co-stimulation signal through 4-1BB upon PD-L1 crosslinking by PD-L1 expressed tumor cells. However, bispecific antibody described in patent US_2017_0198050_A1 activates or induces 4-1BB signaling without crosslink to the target cells, raised the concern of potential toxicity included by 4-1BB at high concentration.

Therefore, there is still insistent need in the art to develop new anti-4-1BB antibodies that has an optimal balance between the safety profile and the agonism. Moreover, such anti-4-1BB antibodies will also be helpful to construct new bispecific antibodies, including bispecific antibodies that can bind to 4-1BB and other antigens, e.g, PD-L1. Such bispecific antibodies that can specifically bind to 4-1BB, while bind to other antigen, such as PD-L1 with higher affinity, are also the purpose of the development in the area of 4-1BB antibody.

SUMMARY OF THE INVENTION

The present disclosure provides an isolated monoclonal agonistic antibody, for example, a human, mouse, chimeric or humanized monoclonal antibody, or the antigen-binding portion thereof, that specifically binds to 4-1BB (e.g., the human 4-1BB). In one embodiment, the antibody of the present invention provides an optimal balance between the safety profile and the agonism.

The antibody or the antigen-binding portion thereof of the disclosure can be used for a variety of applications, including detection of the 4-1BB protein, and treatment of 4-1BB associated diseases, such as tumors, infections, and autoimmune diseases.

Accordingly, in one aspect, the disclosure pertains to an isolated monoclonal antibody (e.g., a human antibody), or an antigen-binding portion thereof, that binds 4-1BB, having a heavy chain variable region that comprises a CDR1 region, a CDR2 region and a CDR3 region, wherein the CDR1 region, the CDR2 region and the CDR3 region comprise amino acid sequences having at least 80%, 81%, 82%, 83%, 84%, 85%, 86%, 87%, 88%, 89%, 90%, 91%. 92%, 93%, 94% 95%, 96%. 97%, 98%, 99% or 100% identity to (1) SEQ ID NOs: 1, 2 and 3, respectively; (2) SEQ ID NOs: 7, 8 and 9, respectively; (3) SEQ ID NOs: 13, 14 and 15, respectively; or (4) SEQ ID NOs: 19, 20 and 21, respectively.

In one aspect, an isolated monoclonal antibody, or an antigen-binding portion thereof, of the present disclosure comprises a heavy chain variable region comprising an amino acid sequence having at least 80%, 81%, 82%, 83%, 84%, 85%, 86%, 87% h, 88%, 89%, 90%, 91%, 92%. 93%. 94% 95%, 96%, 97%. 98%. 99% or 100% identity to SEQ ID NOs: 25, 27, 29, 31, or 77, wherein the antibody or antigen-binding fragment thereof binds to 4-1BB.

In one aspect, an isolated monoclonal antibody, or an antigen-binding portion thereof, of the present disclosure, that binds 4-1BB, comprises a light chain variable region that comprises a CDR1 region, a CDR2 region and a CDR3 region, wherein the CDR1 region, the CDR2 region, and the CDR3 region comprise amino acid sequences having at least 80%. 81%, 82%, 83%, 84%, 85%. 86%. 87%. 88%. 89%. 90%. 91%. 92%. 93%. 94% 95%, 96%, 97%, 98%, 99% or 100% identity to (1) SEQ ID NOs: 4, 5 and 6, respectively; (2) SEQ ID NOs: 10, 11 and 12, respectively; (3) SEQ ID NOs: 16, 17 and 18, respectively; or (4) SEQ ID NOs: 22, 23 and 24, respectively.

In one aspect, an isolated monoclonal antibody, or an antigen-binding portion thereof, of the present disclosure comprises a light chain variable region comprising an amino acid sequence having at least 80%, 81%, 82%, 83%, 84%, 85%, 86%, 87%, 88%, 89%, 90%, 91%, 92%, 93%, 94% 95%, 96%, 97%, 98%, 99% or 100% identity to SEQ ID NOs: 26 (X1=S or G), 28, 30, 32 or 78, wherein the antibody or antigen-binding fragment thereof binds to 4-1BB.

In one aspect, an isolated monoclonal antibody, or an antigen-binding portion thereof, of the present disclosure comprises a heavy chain variable region and a light chain variable region each comprising a CDR1 region, a CDR2 region and a CDR3 region, wherein the heavy chain variable region CDR1, CDR2 and CDR3, and the light chain variable region CDR1, CDR2 and CDR3 comprise amino acid sequences having at least 80%, 81%, 82%, 83%, 84%, 85%, 86%, 87%, 88%, 89%, 90%, 91%, 92%, 93%, 94% 95%, 96%, 97%, 98%, 99% or 100% identity to (1) SEQ ID NOs: 1, 2, 3, 4, 5 and 6, respectively; (2) SEQ ID NOs: 7, 8, 9, 10, I1 and 12, respectively; (3) SEQ ID NOs: 13, 14, 15, 16, 17 and 18, respectively; or (4) SEQ ID NOs: 19, 20, 21, 22, 23 and 24, respectively, wherein the antibody or antigen-binding fragment thereof binds to 4-1BB.

In one embodiment, an isolated monoclonal antibody, or the antigen-binding portion thereof, of the present disclosure comprises a heavy chain variable region and a light chain variable region, the heavy chain variable region and the light chain variable region comprising amino acid sequences having at least 80%, 81%. 82%, 83%, 84%, 85%. 86%, 87%, 88%, 89% i, 90%, 91%. 92%, 93%, 94% 95%, 96%, 97%, 98%, 99% or 100% identity to (1) SEQ ID NOs: 25 and 26 (X1=S), respectively; (2) SEQ ID NOs: 25 and 26 (X1=G), respectively; (3) SEQ ID NOs: 27 and 28, respectively; (4) SEQ ID NOs: 29 and 30, respectively; (5) SEQ ID NOs: 31 and 32, respectively. (6) SEQ ID Nos: 77 and 78, respectively, wherein the antibody or antigen-binding fragment thereof binds to 4-1BB.

In one embodiment, an isolated monoclonal antibody, or the antigen-binding portion thereof, of the present disclosure comprises a heavy chain and a light chain, the heavy chain comprising a heavy chain variable region and a heavy chain constant region, the light chain comprising a light chain variable region and a light chain constant region, wherein the heavy chain constant region may be human IgG1, IgG2, IgG3 or IgG4 constant region, and the light chain constant region may be human lambda or kappa constant region, and the heavy chain variable region and the light chain variable region comprise amino acid sequences described above, wherein the antibody or antigen-binding fragment thereof binds to 4-1BB. In a further embodiment, the heavy chain constant region comprises amino acid sequences set forth in SEQ ID Nos: 33. In a further embodiment, the light chain constant region comprises an amino acid sequence set forth in SEQ ID No: 35 or 63, The heavy chain constant region may be other appropriate constant regions, such as constant regions derived from human IgG constant region, e.g., IgG4 constant region with mutation S228P having amino acid sequences set forth in SEQ ID NO:75, or IgG1 constant region with mutation L234A, L235A, D265A, P329A (Eu numbering) having amino acid sequences set forth in SEQ ID NO:34. The light chain constant region may be other appropriate constant regions derived from human kappa or lambda constant region.

The antibody of the present disclosure in some embodiments comprises or consists of two heavy chains and two light chains connected by disulfide bonds, wherein each heavy chain comprises the heavy chain constant region, heavy chain variable region or CDR sequences mentioned above, and each light chain comprises the light chain constant region, light chain variable region or CDR sequences mentioned above, wherein the C-terminus of the heavy chain variable region is linked to the N-terminus of the heavy chain constant region, and the C-terminus of the light chain variable region is linked to the N-terminus of the light chain constant region. The antibody of the disclosure can be a full-length antibody, for example, of an IgG1, IgG2 or IgG4 isotype. The antibody of the disclosure may contain a kappa or lambda constant region. The antibody or the antigen-binding portion thereof of the present disclosure in other embodiments may be a single chain variable fragment. (scFv) antibody, or antibody fragments, such as Fab or Fab'2 fragments.

The exemplary antibodies, or antigen-binding portions thereof, of the present disclosure are agonistic anti-4-1BB antibodies that specifically bind to 4-188, especially human 4-1BB, and activate the 4-1BB signaling.

The disclosure also provides a bispecific molecule comprising an antibody, or antigen-binding portion thereof, of the disclosure, linked to a second functional moiety (e.g., a second antibody) having a different binding specificity than said antibody, or antigen-binding portion thereof. The bispecific molecule may bind to 4-1BB and another molecule such as PD-1, PD-L1 or CTLA-4, preferably, the molecule is PD-L1.

In one aspect, the antibodies in the present disclosure refers to bispecific antibodies. Therefore, the disclosure also provides a bispecific antibody comprising the first binding region which specifically binds to 4-1BB (e.g., human 4-1BB), and a second binding region which specifically binds to the second antigen related to cancer, infection or autoimmune disease. In one embodiment, the second antigen is selected from (human) PD-1. PD-L1 or CTLA-4. More preferably, the second antigen is (human) PD-L1. In one embodiment, the first binding region which specifically binds to 4-1BB comprises a heavy chain variable region as described above, and/or a light chain variable region as described above. In one embodiment, the first binding region comprises a CDR1 region, a CDR2 region and a CDR3 region of heavy chain variable region as described above, and/or a CDR1 region, a CDR2 region and a CDR3 region of light chain variable region as described above. In one embodiment, the first binding region specifically binds to (human) 4-1BB and specifically binds to a second antigen with high affinity.

In one embodiment, the bispecific antibody described above comprises the first binding region which specifically binds to human 4-1BB, and a second binding region which specifically hinds to human PD-L1 with high affinity, so as to only has activity at tumor microenvironment with PD-L1 expression while avoids stimulating T cells systemically.

Compositions comprising an antibody, or antigen-binding portion thereof, or the bispecific molecule, of the disclosure, and a pharmaceutically acceptable carrier, are also provided. In one embodiment, the composition is pharmaceutical composition.

Nucleic acid molecules encoding the antibodies, or antigen-binding portions thereof, or chain(s) of the antibodies of the disclosure are also encompassed by the disclosure, as well as expression vectors comprising such nucleic acids and host cells comprising such expression vectors or having its genome integrated with the polynucleotide encoding the antibody or the antigen-binding portion thereof. A method for preparing an anti-4-1BB antibody using the host cell comprising the expression vector is also provided, comprising steps of (i) expressing the antibody in the host cell and (ii) isolating the antibody from the host cell or its cell culture.

In yet another aspect, the disclosure provides a method of treating a cancer disease in a subject, comprising administering to the subject in need thereof the antibody, or antigen-binding portion thereof, of the disclosure. In some embodiments, the method comprises administering a composition, or a bispecific molecule of the disclosure, or alternatively a nucleic acid molecule capable of expressing the same in the subject. The bispecific molecule may bind to 4-1BB and another protein, such as PD-1, PD-L1 or CTLA-4, preferably PD-LL.

In some embodiments, at least one additional antibody can be administered with the antibody, or an antigen-binding portion thereof, of the disclosure, such as an anti-PD-1 antibody, an anti-PD-L1 antibody, and/or an anti-CTLA-4 antibody. In some embodiments, at least one additional anti-cancer drug can be administered with the antibody, or an antigen-binding portion thereof, of the disclosure. The cancer may be a solid or non-solid cancer, e.g., cancer in gastrointestinal tract, such as colon cancer, colorectal cancer or rectal cancer.

In another aspect, the disclosure discloses a method for treating an infection in a subject, comprising administering to the subject in need thereof the antibody, the antigen-binding portion thereof, the specific molecule or the pharmaceutical composition of the disclosure, optionally with an additional anti-viral agent, anti-bacterial agent or anti-fungal agent.

In another aspect, the disclosure discloses a method for treating an autoimmune disease comprising administering to the subject in need thereof the antibody, the antigen-binding portion thereof, the specific molecule or the pharmaceutical composition of the disclosure. The autoimmune disease may be asthma or rheumatoid arthritis. Optionally, an additional anti-asthma agent, or anti-rheumatoid arthritis agent may be administered.

Other features and advantages of the instant disclosure will be apparent from the following detailed description and examples, which should not be construed as limiting. The contents of all references, Genbank entries, patents and published patent applications cited throughout this application are expressly incorporated herein by reference.

DETAILED DESCRIPTION OF THE INVENTION

Figure 1A:
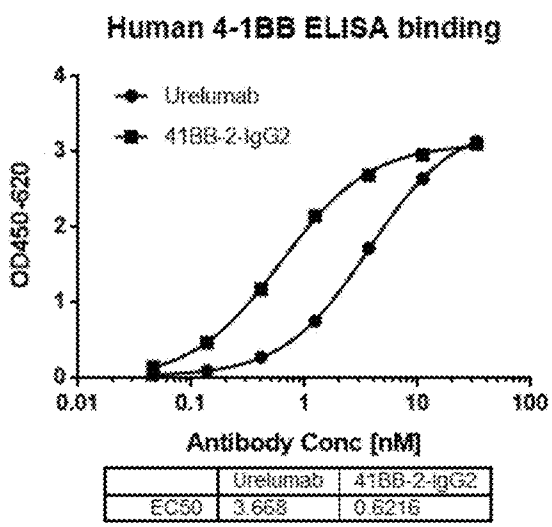
FIG. 1A-1D show the binding capacities of anti-4-1BB antibodies 41 BB-2-IgG2 (A), 41BB-9-IgG2 (B), 41BB-13-IgG2 (C) and 41BB-27-IgG2 (D) to human 4-1BB in ELISA assay.
Figure 1B:
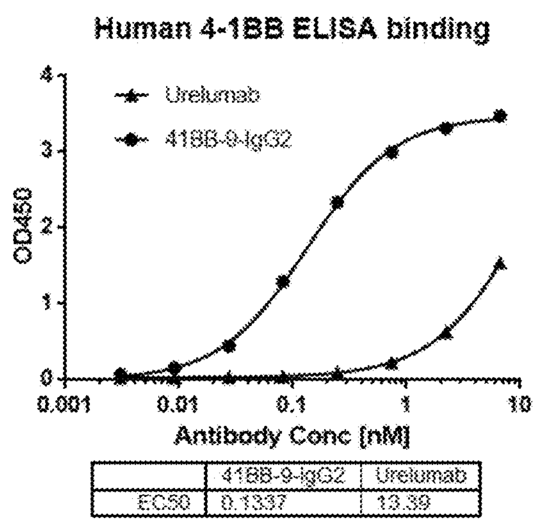
Figure 1C:
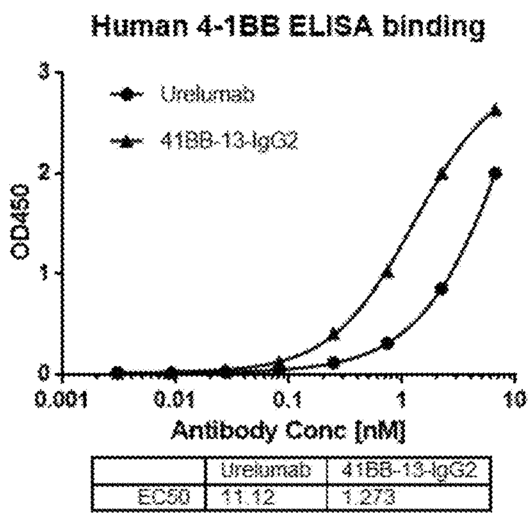
Figure 1D:
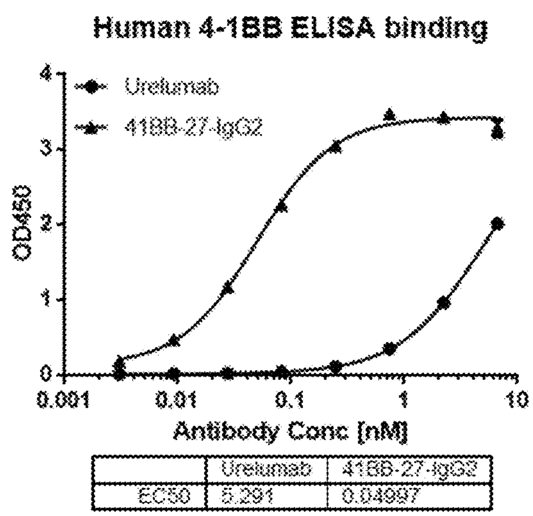

To ensure that the present disclosure may be more readily understood, certain terms are first defined. Additional definitions are set forth throughout the detailed description.

The term "4-1BB" refers to tumor necrosis factor receptor superfamily member 9.

The term "4-1BB" comprises variants, isoforms, homologs, orthologs and paralogs. For example, an antibody specific for a human 4-1BB protein may, in certain cases, cross-react with a 4-1BB protein from a species other than human, such as monkey. In other embodiments, an antibody specific for a human 4-11313 protein may be completely specific for the human 4-11313 protein and exhibit no cross-reactivity to other species or of other types, or may cross-react with 4-1BB from certain other species but not all other species.

The term "human 4-1BB" refers to a 4-11BB protein having an amino acid sequence from a human, such as the amino acid sequence of human 4-1BB having a Genbank accession number of NP_001552.2. In one embodiment, the human 4-1BB comprises amino acid sequences as set forth in SEQ ID NO:39. The terms "monkey or Rhesus 4-1BB" and "mouse 4-1BB" refer to monkey and mouse 4-1BB sequences, respectively, e.g. those with the amino acid sequences having Genbank Accession Nos. NP_001253057.1 and NP_033430.1, respectively.

The term "antibody" as referred to herein includes whole antibodies and any antigen binding fragment (i.e., "antigen-binding portion") or single chains thereof. In addition, the term "antibody" as referred to herein also encompasses multiple specific antibodies, such as bispecific antibodies or trispecific antibodies. Whole antibodies are glycoproteins comprising two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3. CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a 4-1BB protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) *Science* 242:423-426; and Huston et al., (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

The term "bispecific" means that the antibody is able to specifically bind to at least two distinct antigenic determinants. Typically, a bispecific antibody comprises two antigen binding regions, each of which is specific for a different antigenic determinant. In certain embodiments the bispecific antibody is capable of simultaneously binding two antigenic determinants, particularly two antigenic determinants expressed on two distinct cells. As used herein, the term "antigenic determinant" is synonymous with "antigen" and "epitope", and refers to a site (e.g. a contiguous stretch of amino acids or a conformational configuration made up of different regions of non-contiguous amino acids) on a polypeptide macromolecule to which an antigen binding moiety binds, forming an antigen binding region-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM).

As used herein, the term "antigen binding region" refers to a polypeptide molecule that specifically binds to an antigenic determinant. In one embodiment, an antigen binding region is able to direct the entity to which it is attached (e.g. a second antigen binding region) to a target site, for example to a specific type of tumor cell bearing the antigenic determinant. In another embodiment an antigen binding region (e.g., a first antigen binding region) is able to activate signaling through its target antigen, for example a T cell receptor antigen. Antigen binding regions include antibodies or antigen-binding fragments thereof as defined herein. Particular antigen binding regions include an antigen binding fragments of an antibody, comprising an antibody heavy chain variable region and an antibody light chain variable region. In certain embodiments, the antigen binding regions may comprise antibody constant regions as defined herein and known in the art.

By "specific binding" is meant that the binding is selective for the antigen and can be discriminated from unwanted or non-specific interaction. The ability of an antigen binding region to bind to a specific antigenic determinant can be measured either through an enzyme-linked immunosorbent assay (ELISA) or other techniques familiar to one of skill in the art, e.g. surface plasmon resonance (SPR) technique (analyzed e.g. on a BIAcore instrument).

Unless indicated otherwise, as used herein, "binding affinity" refers to intrinsic binding affinity which reflects a 1:1 interaction between members of a binding pair (e.g., a monoclonal antibody and an antigen, an antigen binding region and an antigen, or a receptor and its ligand). Affinity can be measured by well established methods known in the art, including those described herein.

An "isolated antibody", as used herein, is intended to refer to an antibody that is substantially free of other antibodies having different antigenic specificities (e.g., an isolated antibody that specifically binds a 4-1BB protein is substantially free of antibodies that specifically bind antigens other than 4-1BB proteins). An isolated antibody that specifically binds a human 4-1BB protein may, however, have cross-reactivity to other antigens, such as 4-1BB proteins from other species. Moreover, an isolated antibody can be substantially free of other cellular material and/or chemicals. The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the disclosure can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species have been grafted onto human framework sequences.

The term "agonistic 4-1BB antibody" or "agonistic anti-4-1BB antibody" refers to an anti-4-1BB antibody that binds to 4-1BB and activates or induces 4-4BB signaling to promote activation and/or proliferation of immune cells such as T cells.

The term "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to human 4-1BB" is intended to refer to an antibody that binds to human 4-1BB protein (and possibly a 4-1BB protein from one or more non-human species) but does not substantially bind to non-4-1BB proteins. Preferably, the antibody binds to human 4-1BB protein with a $K_D$ of $1.0\times10^{-6}$ M or less, preferably $5.0\times10^{-7}$ M or less, and more preferably $1.0\times10^{-7}$ M or less.

The term "does not substantially bind" to a protein or cells, as used herein, means does not specifically bind or does not bind with a high affinity to the protein or cells, i.e. binds to the protein or cells with a $K_D$ of $1.0\times10^{-6}$ M or more, more preferably $1.0\times10^{5}$ M or more, preferably $1.0\times10^{-4}$ M or more, more preferably $1.0\times10^{-3}$ M or more, even more preferably $1.0\times10^{-2}$ M or more.

The term "specifically binds to a second antigen (PD-L1) with high affinity" for an IgG antibody or antigen binding region thereof refers to an antibody or antigen binding region having a $K_D$ of $1.0\times10^{-8}$ M or less, more preferably $5.0\times10^{-9}$ M or less, even more preferably $1.0\times10^{-9}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "$IC_{50}$", also known as half maximal inhibitory concentration, refers to the concentration of an antibody which inhibits a specific biological or biochemical function by 50% relative to the absence of the antibody.

The term "subject" includes any human or nonhuman animal. The term "nonhuman animal" includes all vertebrates. e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "therapeutically effective amount" means an amount of the antibody of the present disclosure sufficient to prevent or ameliorate the symptoms associated with a disease or condition (such as a cancer) and/or lessen the severity of the disease or condition. A therapeutically effective amount is understood to be in context to the condition being treated, where the actual effective amount is readily discerned by those of skill in the art.

The term "therapeutic agent" as described herein encompasses any substance effective in preventing or treating tumors (such as cancer) or infections or autoimmune diseases, including chemotherapeutic agents, cytotoxic agents, vaccines, other antibodies (e.g., antibodies against to the immune checkpoint molecule), anti-infection agents, immunomodulators, small molecule drugs.

The term "chemotherapeutic agents" include chemical compounds useful in treatment of cancer.

The term "anti-infective agent" includes any molecule that specifically inhibits or eliminates the growth of microorganisms such as viruses, bacteria, fungi, or protozoa, e.g., parasites, and is not lethal to the host, at the administration concentration and interval of administration.

As used herein, the term anti-infective agent includes antibiotics, antibacterials, antivirals, antifungals, and anti-protozoals. In one specific aspect, the anti-infective agent is non-toxic to the host at the administration concentration and interval of administration.

Immunomodulators include immune checkpoint molecule inhibitors and co-stimulatory molecule activators.

The term "small molecule drugs" refers to low molecular weight organic compounds capable of regulating biological processes. "Small molecules" are defined as molecules with a molecular weight of usually less than 2 kD and preferably less than 1 kD, and more preferably about 500 daltons or less. Small molecules include, but are not limited to, inorganic molecules, organic molecules, organic molecules containing inorganic components, molecules containing radioactive atoms, synthetic molecules, peptide mimetics, and antibody mimetics.

The terms "cancer" and "cancerous" refer to or describe a physiological disease in mammals that is typically characterized by unregulated cell growth.

The term "tumor" refers to all neoplastic cell growth and proliferation regardless of whether malignant or benign, and all pre-cancerous and cancerous cells and tissues. The terms "cancer", "cancerous", "cell proliferative disorder". "proliferative disorder", and "tumor" are not mutually exclusive when referred to herein.

The term "infection" refers to a disease caused by a pathogen, including, for example, viral infection, bacterial infection, fungal infection, or protozoan such as parasitic infection.

The term "tumor immune escape" refers to tumors evading immune recognition and clearance. Therefore, as a concept of treatment, tumor immunity is "treated" and the tumor is recognized and attacked by the immune system when the escape is weakened. Examples of tumor recognition include tumor binding, tumor shrinkage, and tumor clearance.

Various aspects of the disclosure are described in further detail in the following subsections.

Anti-4-1BB Antibodies Having Binding Affinity to Human 4-1BB

The exemplary antibody, or the antigen-binding portion thereof, of the disclosure specifically binds to human 4-1BB. The exemplary antibody, or the antigen-binding portion thereof, of the disclosure is an agonistic antibody that activates or induces 4-1BB signaling to promote activation and/or proliferation of immune cells such as T cells.

In one aspect, the present invention relates to an anti-4-1BB antibody or the antigen-binding fragment thereof, which comprises three heavy chain variable region CDRs CDR1, CDR2 and CDR3.

In another aspect, the present invention relates to an anti-4-1BB antibody or the antigen-binding fragment thereof, which comprises three light chain variable region CDRs CDR1, CDR2 and CDR3.

In a further aspect, the present invention relates to an anti-4-1BB antibody or the antigen-binding fragment thereof, which comprises three heavy chain variable region CDRs CDR1, CDR2 and CDR3; and three light chain variable region CDRs CDR1, CDR2 and CDR3.

In another aspect, the present invention relates to an anti-4-1BB antibody or the antigen-binding fragment thereof, which comprises a heavy chain variable region.

In another aspect, the present invention relates to an anti-4-1BB antibody or the antigen-binding fragment thereof, which comprises a light chain variable region.

In a further aspect, the present invention relates to an anti-4-1BB antibody or the antigen-binding fragment thereof, which comprises a heavy chain variable region and a light chain variable region.

In one embodiment, the heavy chain variable region comprises three heavy chain variable region CDRs CDR1, CDR2 and CDR3.

In another embodiment, the light chain variable region comprises three light chain variable region CDRs CDR1, CDR2 and CDR3.

In one embodiment, the three heavy chain variable region CDR1, CDR2 and CDR3 are (i) the CDR1, CDR2 and CDR3 derived from a heavy chain variable region $V_H$, wherein the $V_H$ comprises or consists of the sequence represented by SEQ ID NO: 25, 27, 29, 31 or 77, or (ii) the CDR1. CDR2 and CDR3 of (i), further comprising at least one and no more than 5 amino acid modifications (preferably amino acid substitutions, preferably conservative substitutions) in total compared to the three CDRs of (i).

In one embodiment, the three light chain variable region CDRs CDR1, CDR2 and CDR3 are (i) the CDR1, CDR2 and CDR3 derived from the light chain variable region $V_L$, wherein the $V_L$ comprises or consists of the sequence represented by SEQ ID NO:26, 28, 30, 32 or 78, or (ii) CDR1, CDR2 and CDR3 of (i), which further comprise at least one and no more than 5 amino acid modifications (preferably amino acid substitutions, preferably conservative substitutions) in total compared to the three CDRs of (i).

In one embodiment, the present invention relates to an anti-4-1BB antibody or the antigen-binding fragment thereof, which comprises three heavy chain variable region CDRs CDR1, CDR2 and CDR3 derived from the heavy chain variable region $V_H$, wherein the $V_H$ consists of the sequence represented by SEQ ID NO: 25, 27, 29, 31 or 77; and three light chain variable region CDRs CDR1, CDR2 and CDR3 derived from the light chain variable region $V_L$, wherein the $V_L$ consists of the sequence represented by SEQ ID NO: 26, 28, 30, 32 or 78.

In another embodiment, the present invention relates to an anti-4-1BB antibody or the antigen-binding fragment thereof, which comprises (1) three CDRs CDR1, CDR2 and CDR3 derived from the heavy chain variable region consisting of the sequence represented by SEQ ID NO: 25 or 77; and three CDRs CDR1, CDR2 and CDR3 derived from the light chain variable region consisting of the sequence represented by SEQ ID NO:26 or 78;

(2) three CDRs CDR1, CDR2 and CDR3 derived from the heavy chain variable region consisting of the sequence represented by SEQ ID NO:27; and three CDRs CDR1, CDR2 and CDR3 derived from the light chain variable region consisting of the sequence represented by SEQ ID NO:28;

(3) three CDRs CDR1, CDR2 and CDR3 derived from the heavy chain variable region consisting of the sequence represented by SEQ ID NO:29; and three CDRs CDR1, CDR2 and CDR3 derived from the light chain variable region consisting of the sequence represented by SEQ ID NO:30;

(4) three CDRs CDR1, CDR2 and CDR3 derived from the heavy chain variable region consisting of the sequence represented by SEQ ID NO:31; and three CDRs CDR1, CDR2 and CDR3 derived from the light chain variable region consisting of the sequence represented by SEQ ID NO:32.

In one embodiment, $V_H$ CDR1 comprises or consists of an amino acid sequence selected from the group consisting of SEQ ID NO: 1, 7, 13 or 19, or $V_H$ CDR1 comprises or consists of an amino acid sequence having one, two or three modifications (preferably amino acid substitutions, preferably conservative substitutions) compared to the amino acid sequence selected from the group consisting of SEQ ID NO: 1, 7, 13 or 19.

In one embodiment, $V_H$ CDR2 comprises or consists of an amino acid sequence selected from the group consisting of SEQ ID NO: 2, 8, 14 or 20, or $V_H$ CDR2 comprises or consists of an amino acid sequence having one, two or three modifications (preferably amino acid substitutions, preferably conservative substitutions) compared to the amino acid sequence selected from the group consisting of SEQ ID NO: 2, 8, 14 or 20.

In one embodiment, $V_H$ CDR3 comprises or consists of an amino acid sequence selected from the group consisting of SEQ ID NO: 3, 9, 15, or 21, or $V_H$ CDR3 comprises or consists of an amino acid sequence having one, two or three modifications (preferably amino acid substitutions, preferably conservative substitutions) compared to the amino acid sequence selected from the group consisting of SEQ ID NO: 3, 9, 15, or 21.

In one embodiment, $V_L$ CDR1 comprises or consists of an amino acid sequence selected from the group consisting of SEQ ID NO: 4, 10, 16 or 22, or $V_L$ CDR1 comprises or consists of an amino acid sequence having one, two or three modifications (preferably amino acid substitutions, preferably conservative substitutions) compared to the amino acid sequence selected from the group consisting of SEQ ID NO: 4, 10, 16 or 22.

In one embodiment, $V_L$ CDR2 comprises or consists of an amino acid sequence selected from the group consisting of SEQ ID NO: 5, 11, 17 or 23, or $V_L$ CDR2 comprises or consists of an amino acid sequence having one, two or three modifications (preferably amino acid substitutions, preferably conservative substitutions) compared to the amino acid sequence selected from the group consisting of SEQ ID NO: 5, 11, 17 or 23.

In one embodiment, $V_L$ CDR3 comprises or consists of an amino acid sequence selected from the group consisting of SEQ ID NO: 6, 12, 18 or 24, or $V_L$ CDR3 comprises or consists of an amino acid sequence having one, two or three modifications (preferably amino acid substitutions, preferably conservative substitutions) compared to the amino acid sequence selected from the group consisting of SEQ ID NO: 6, 12, 18 or 24.

In one embodiment, the three heavy chain variable region $V_H$ CDR1, CDR2 and CDR3 are (i) the CDR1, CDR2 and CDR3 consisting of the sequence represented by SEQ ID NO: 1, 2 and 3 respectively, or (ii) the CDR1, CDR2 and CDR3 consisting of the sequence represented by SEQ ID NO: 7, 8 and 9 respectively, or (iii) the CDR1, CDR2 and CDR3 consisting of the sequence represented by SEQ ID NO: 13, 14 and 15 respectively, or (iv) the CDR1, CDR2 and CDR3 consisting of the sequence represented by SEQ ID NO: 19, 20 and 21 respectively, or (v) the CDR1, CDR2 and CDR3 of anyone of (i) to (iv), further comprising at least one and no more than 5 amino acid modifications (preferably amino acid substitutions, preferably conservative substitutions) in total compared to the three CDRs of anyone of (i) to (iv).

In one embodiment, the three light chain variable region $V_L$ CDRs CDR1, CDR2 and CDR3 are (i) the CDR1, CDR2 and CDR3 consisting of the sequence represented by SEQ ID NO: 4, 5 and 6 respectively, or (ii) the CDR1, CDR2 and CDR3 consisting of the sequence represented by SEQ ID NO: 10, 11 and 12 respectively, or (iii) the CDR1, CDR2 and CDR3 consisting of the sequence represented by SEQ ID NO: 16, 17 and 18 respectively, or (iv) the CDR1, CDR2 and CDR3 consisting of the sequence represented by SEQ ID NO: 22, 23 and 24 respectively, or (v) CDR1, CDR2 and CDR3 of anyone of (i) to (iv), which further comprise at least one and no more than 5 amino acid modifications (preferably amino acid substitutions, preferably conservative substitutions) in total compared to the three CDRs of anyone of (i) to (iv).

In another embodiment, the present invention relates to an anti-4-1BB antibody or the antigen-binding fragment thereof, which comprises (i) the $V_H$ CDR1, CDR2 and CDR3 consisting of the sequence represented by SEQ ID NO: 1, 2 and 3 respectively, and the $V_L$ CDR1, CDR2 and CDR3 consisting of the sequence represented by SEQ ID NO: 4, 5 and 6 respectively;

(ii) the $V_H$ CDR1, CDR2 and CDR3 consisting of the sequence represented by SEQ ID NO: 7, 8 and 9 respectively, and the $V_L$ CDR1, CDR2 and CDR3 consisting of the sequence represented by SEQ ID NO: 10, 11 and 12 respectively;

(iii) the $V_H$ CDR1, CDR2 and CDR3 consisting of the sequence represented by SEQ ID NO: 13, 14 and 15 respectively, and the $V_L$ CDR1, CDR2 and CDR3 consisting of the sequence represented by SEQ ID NO: 16, 17 and 18 respectively; or (iv) the $V_H$ CDR1, CDR2 and CDR3 consisting of the sequence represented by SEQ ID NO: 19, 20 and 21 respectively, and the $V_L$ CDR1, CDR2 and CDR3 consisting of the sequence represented by SEQ ID NO: 22, 23 and 24 respectively.

In one embodiment, the heavy chain variable region (i) comprises or consists of an amino acid sequence having at least 80%, 81%, 82%, 83%, 84%, 85%, 86%, 87%. 88%, 89%, 90%. 91%, 92%, 93%, 94% 95%, 96%. 97%, 98%, or 99% identity with the amino acid sequence selected from the group consisting of SEQ ID NO: 25, 27, 29, 31 or 77; or (ii) comprises or consists of an amino acid sequence selected from the group consisting of SEQ ID NO: 25, 27, 29, 31 or 77; or (iii) comprises or consists of an amino acid sequence having one or more (preferably no more than 10, more preferably no more than 5) amino acid modifications (preferably amino acid substitutions, more preferably conservative substitutions) compared to an amino acid sequence selected from the group consisting of SEQ ID NOs: 25, 27, 29, 31 or 77, preferably, said amino acid modifications do not occur in the CDR regions, more preferably, said amino acid modifications occur in FR regions, e.g., FR1, FR2, FR3 or FR4 regions.

In another embodiment, the light chain variable region (i) comprises or consists of an amino acid sequence having at least 80%, 81% 1, 82%, 83%. 84%, 85%, 86%. 87%, 88%, 89%, 90%, 91%, 92%, 93%. 94% 95%. 96%, 97%, 98%, or 99% identity with the amino acid sequence selected from the group consisting of SEQ ID NOs: 26, 28, 30, 32 or 78; or (ii) comprises or consists of an amino acid sequence selected from the group consisting of SEQ ID NOs: 26, 28, 30, 32 or 78; or (iii) comprises or consists of an amino acid sequence having one or more (preferably no more than 10, more preferably no more than 5) amino acid modifications (preferably amino acid substitutions, more preferably conservative substitutions) compared to an amino acid sequence selected from the group consisting of SEQ ID NOs: 26, 28, 30, 32 or 78, preferably, said amino acid modifications do not occur in the CDR regions, more preferably, said amino acid modifications occur in FR regions, e.g., FR1, FR2, FR3 or FR4 regions.

In one embodiment, the variable regions can be modified to improve the purification of the antibody. For example, at the end of the heavy chain variable region, the amino acid can be mutated from S to G to obtain the antibody which can be prepared in high purity.

In another embodiment, the variable regions can be modified to improve the stability of the antibody or the antigen binding portion (e.g., scFv). For example, the mutation can be made to form the disulfide bond between the heavy chain variable region and the light chain variable region. For example, the mutation in the heavy chain variable region is G44C (Eu numbering) and/or the mutation in the light chain variable region is T104C (Eu numbering).

In another embodiment, the present invention relates to an anti-4-1BB antibody or the antigen-binding fragment thereof, which comprises:

a heavy chain variable region comprising or consisting of an amino acid sequence represented by SEQ ID NOs: 25, 27, 29, 31 or 77, and/or a light chain variable region comprising or consisting of an amino acid sequence represented by SEQ ID NOs: 26, 28, 30, 32, or 78.

In another embodiment, the present invention relates to an anti-4-1BB antibody or the antigen-binding fragment thereof, which comprises:

(1) a heavy chain variable region comprising or consisting of an amino acid sequence represented by SEQ ID NO: 25, and a light chain variable region consisting of an amino acid sequence represented by SEQ ID No: 26;

(2) a heavy chain variable region comprising or consisting of an amino acid sequence represented by SEQ ID NO: 27, and a light chain variable region consisting of an amino acid sequence represented by SEQ ID No: 28;

(3) a heavy chain variable region comprising or consisting of an amino acid sequence represented by SEQ ID NO: 29, and a light chain variable region consisting of an amino acid sequence represented by SEQ ID No: 30;

(4) a heavy chain variable region comprising or consisting of an amino acid sequence represented by SEQ ID NO: 31, and a light chain variable region consisting of an amino acid sequence represented by SEQ ID No: 32; or (5) a heavy chain variable region comprising or consisting of an amino acid sequence represented by SEQ ID NO: 77, and a light chain variable region consisting of an amino acid sequence represented by SEQ ID No: 78.

In a further aspect, the anti-4-1BB antibody or the antigen-binding fragment thereof further comprises heavy chain constant region, and/or light chain constant region.

In one embodiment, the heavy chain constant region is or is derived from human IgG constant region, e.g., IgG1, IgG2, IgG3 or IgG4, preferable IgG1 constant region or IgG2 constant region or IgG4 constant region.

In another embodiment, the heavy chain constant region (i) comprises or consists of an amino acid sequence having at least 80%, 85%, 90%. 91%. 92%, 93%, 94%. 95%, 96%, 97%, 98% or 99% identity with the amino acid sequence represented by SEQ ID NO: 33 or 34 or 75; or (ii) comprises or consists of an amino acid sequence represented by SEQ ID NO: 33 or 34 or 75; or (iii) comprises or consists of an amino acid sequence having one or more (preferably no more than 10, more preferably no more than 5) amino acid modifications (preferably amino acid substitutions, more preferably conservative substitutions) compared to an amino acid sequence represented by SEQ ID NO:33 or 34 or 75.

In one embodiment, the light chain constant region is or is derived from kappa or lambda light chain constant region, e.g., human kappa or lambda light chain constant region, e.g., human lambda light chain constant region.

In another embodiment, the light chain constant region (i) comprises or consists of an amino acid sequence having at least 80%, 85%, 90%, 91%, 92%, 93%, 94%, 95%, 96%, 97%, 98% or 99% identity with the amino acid sequence represented by SEQ ID NO: 35 or 63; or (ii) comprises or consists of an amino acid sequence represented by SEQ ID NO: 35 or 63; or (iii) comprises or consists of an amino acid sequence having one or more (preferably no more than 10, more preferably no more than 5) amino acid modifications (preferably amino acid substitutions, more preferably conservative substitutions) compared to an amino acid sequence represented by SEQ ID NO:35 or 63.

In one embodiment, the constant region of the antibody can be mutated to improve the production and purification of the antibody. For example, IgG4 constant region can have a mutation of S228P(EU numbering). IgG1 constant region can have a mutation of L234A, L235A, D265A, P329A (Eu numbering).

In one embodiment, the antigen-binding fragment of the antibody of the disclosure is scFv fragment. Particularly, the scFv fragment comprises a light chain variable region and a heavy chain variable region, connected by a linker. In one embodiment, the linker is a flexible linker, such as a linker having glycine and/or serine residues alone or in combination.

In one embodiment, the linker comprises the amino acid sequence (Gly4Ser)n or (GlySer4)n, wherein n is a positive integer equal to or greater than 1, for example, n is a positive integer from 1 to 7, for example, n is 2, 3, 4, 5, 6. In one embodiment, n is 1, 2, 3, or 4. In a particular embodiment, the linker comprises or consists of the amino acid sequences represented by SEQ ID NO: 36 or SEQ ID NO: 51 or SEQ ID NO:52.

Preferred Antibodies of the Disclosure are Monoclonal Antibodies.

Monoclonal Anti-4-1BB Antibody

The antibody of the disclosure may be the monoclonal antibody structurally and chemically characterized as described below and in the following Examples. The amino acid sequence ID numbers of the CDR regions or the heavy/light chain variable regions of the antibodies are summarized in Table 1 below. The heavy chain constant region for the antibodies may be human IgG1 or IgG2 or IgG4 heavy chain constant region having an amino acid sequence set forth in, e.g., SEQ ID NOs: 33 or 34 or 75, and the light chain constant region for the antibodies may be human lambda constant region having an amino acid sequence set forth in. e.g., SEQ ID NO: 35 or 63. The antibody may comprise or consist of two heavy chain and two light chains connected by disulfide bonds, the C-terminus of the heavy chain variable region is linked to the N-terminus of the heavy chain constant region, and the C-terminus of the light chain variable region is linked to the N-terminus of the light chain constant region.

TABLE 1

Amino acid sequence ID numbers of heavy/light chain variable regions

| | Heavy chain | | | | Light chain | | | |
|---|---|---|---|---|---|---|---|---|
| Antibody | VH CDR1 | VH CDR2 | VH CDR3 | VH | VL CDR1 | VL CDR2 | VL CDR3 | VL |
| 41BB-2 | 1 | 2 | 3 | 25 | 4 | 5 | 6 | 26, X1 = S or G |
| 41BB-9 | 7 | 8 | 9 | 27 | 10 | 11 | 12 | 28 |
| 41BB-13 | 13 | 14 | 15 | 29 | 16 | 17 | 18 | 30 |
| 41BB-27 | 19 | 20 | 21 | 31 | 22 | 23 | 24 | 32 |
| 41BB-2' | 1 | 2 | 3 | 77 | 4 | 5 | 6 | 78 |

The heavy chain variable region CDRs and the light chain variable region CDRs in Table 1 have been defined by the Kabat numbering system. However, as is well known in the art, CDR regions can also be determined by other systems such as Chothia, and IMGT, AbM, or Contact numbering system/method, based on heavy chain/light chain variable region sequences. It should be noted that boundaries of CDRs of variable regions of an antibody obtained by different numbering systems may differ. That is, CDR sequences of variable regions of an antibody defined by different numbering systems differ. Therefore, when it comes to defining an antibody with specific CDR sequences defined in the invention, the scope of the antibody also encompasses such antibody whose variable region sequences comprise the specific CDR sequences, but having claimed CDR boundaries different from the specific CDR boundaries defined by the invention as a different protocol (e.g., different numbering system rules or their combinations) is applied.

The $V_H$ and $V_L$ sequences (or CDR sequences) of other anti-4-1BB antibodies which bind to human 4-1BB can be "mixed and matched" with the $V_H$ and $V_L$ sequences (or CDR sequences) of the anti-4-1BB antibody of the present disclosure. Preferably, when $V_H$ and $V_L$ chains (or the CDRs within such chains) are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence. Accordingly, in one embodiment, an antibody of the disclosure, or an antigen binding portion thereof, comprises:

(a) a heavy chain variable region comprising an amino acid sequence listed above in Table 1; and
(b) a light chain variable region comprising an amino acid sequence listed above in Table 1, or the $V_L$ of another anti-4-1BB antibody, wherein the antibody specifically binds human 4-1BB.

In another embodiment, an antibody of the disclosure, or an antigen binding portion thereof, comprises:

(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-4-1BB antibody, wherein the antibody specifically binds human 4-1BB.

In yet another embodiment, the antibody, or antigen binding portion thereof, includes the heavy chain variable CDR2 region of anti-4-1BB antibody combined with CDRs of other antibodies which bind human 4-1BB, e.g., CDR1 and/or CDR3 from the heavy chain variable region, and/or CDR1, CDR2, and/or CDR3 from the light chain variable region of a different anti-4-1BB antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al., *British J. of Cancer* 83(2):252-260 (2000); Beiboer et al., *J. Mol. Biol.* 296:833-849 (2000); Rader et al., *Proc. Natl. Acad. Sci. U.S.A.* 95:8910-8915 (1998); Barhas et al., *J. Am. Chem. Soc.* 116:2161-2162 (1994); Barbas et al., *Proc. Natl. Acad. Sci. U.S.A.* 92:2529-2533 (1995); Ditzel et al., *J. Immunol.* 157:739-749 (1996); Berezov et al., *BIAjournal* 8: *Scientific Review* 8 (2001); Igarashi et al., *J. Biochem* (Tokyo) 117:452-7 (1995): Bourgeois et al., *J. Virol* 72:807-10 (1998): Levi et al., *Proc. Natl. Acad. Sci. U.S.A.* 90:4374-8 (1993); Polymenis and Stoller, *J. Immunol.* 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, antibodies of the disclosure comprise the CDR2 of the heavy chain variable region of the anti-4-1BB antibody and at least the CDR3 of the heavy and/or light chain variable region of the anti-4-1BB antibody, or the CDR3 of the heavy and/or light chain variable region of another anti-4-1BB antibody, wherein the antibody is capable of specifically binding to human 4-1BB. These antibodies preferably (a) compete for binding with 4-1BB; (b) retain the functional characteristics; (c) bind to the same epitope; and/or (d) have a similar binding affinity as the anti-4-1BB antibody of the present disclosure. In yet another embodiment, the antibodies further may comprise the CDR2 of the light chain variable region of the anti-4-1BB antibody, or the CDR2 of the light chain variable region of another anti-4-188 antibody, wherein the antibody is capable of specifically binding to human 4-1BB. In another embodiment, the antibodies of the disclosure may include the CDR1 of the heavy and/or light chain variable region of the anti-4-1BB antibody, or the CDR1 of the heavy and/or light chain variable region of another anti-4-1BB antibody, wherein the antibody is capable of specifically binding to human 4-1BB.

Preferred antibodies of the disclosure are bispecific antibodies.

Bispecific Molecules

In another aspect, the present disclosure features bispecific molecules comprising one or more antibodies or antibody binding fragment of the disclosure linked to at least one other functional molecule, e.g., another peptide or protein (e.g., another antibody or ligand for a receptor) to generate a bispecific molecule that binds to at least two different binding sites or target molecules. Thus, as used herein, "bispecific molecule" includes molecules that have three or more specificities.

In an embodiment, a bispecific molecule has, in addition to an anti-4-1BB binding specificity, a second specificity. The second specificity can be PD-1, PD-L1 or CTLA-4.

In an embodiment, a bispecific molecule has, in addition to an anti-4-1BB binding specificity and an anti-PD-L1 binding specificity, a third specificity. The third specificity can be for PD-1, or CTLA-4 for cancer treatment.

Bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called $Bs(scFv)_2$ construct. Intermediate-sized bispecific molecules include two different Fab) fragments linked by a peptidyl linker. Bispecific molecules of these and other formats can be prepared by genetic engineering, somatic hybridization, or chemical methods. See. e.g., Kufer et al. cited supra; Cao and Suresh. *Bioconjugate Chemistry,* 9 (6), 635-644 (1998); and van Spriel et al., *Immunology Today,* 21 (8), 391-397 (2000), and the references cited therein.

In one embodiment, the bispecific molecule of the present invention is a bispecific antibody, comprising a first binding region which specifically binds to 4-1BB, and a second binding region which specifically binds to the second antigen relating to cancer, infection or autoimmune disease. The bispecific antibody can be in several structural format (c.f., Aran F. Labrijn et al., Bispecitic antibodies: a mechanistic review of the pipeline, Nature Reviews Drug Discovery, volume 18, pages 585-608(2019)). For example, bispecific antibodies can be IgG-like, i.e. full length bispecific antibodies, or non-IgG-like bispecific antibodies, which are not full-length antibody constructs.

Particularly, the second antigen is selected from PD-1, PD-L1, or CTLA-4. e.g., human PD-1, PD-L1 or CTLA-4. More preferably, the second antigen is PD-L1, e.g., human PD-L1. In one embodiment, the human PD-L1 comprises the amino acid sequence as set forth in SEQ ID NO:61 or amino acid sequences having at least 85%, 86%, 87%, 88%, 89%, 90%, 91%, 92%, 93%, 94%, 95%, 96%, 97%, 98%, 99% identity with SEQ ID NO:61. In another embodiment, the human PD-L1 is encoded by a nucleic acid molecule comprising a nucleic acid sequence as set forth in SEQ ID NO:62, or a nucleic acid sequence having at least 85%, 86%. 87%. 88%, 89%, 90%, 91%, 92%, 93%, 94%, 95%, 96%, 97%, 98%, 99% identity with SEQ ID NO:62.

In one embodiment, the first binding region comprises the $V_H$ and/or $V_L$ disclosed for the anti-4-1BB antibodies or antibody binding fragment above. In another embodiment, the first binding region comprises the heavy chain variable region CDR1. CDR2 and/or CDR3; and/or the light chain variable region CDR1, CDR2 and/or CDR3, which are disclosed for the anti-4-1BB antibodies or antibody binding fragment as described above. In a further embodiment, the first binding region further comprises constant region, e.g., heavy chain constant region or the light chain constant region, which are disclosed for the anti-4-1BB antibodies or antibody binding fragment as described above. In one embodiment, the first binding region comprises the scFv of anti-4-1BB antibodies as disclosed herein above.

In another embodiment, the second binding region comprises the $V_H$ and/or $V_L$ disclosed for the anti-PD-L1, or anti-PD-1 or anti-CTLA-4 antibodies or antibody binding fragment in the art. In another embodiment, the second binding region comprises the heavy chain variable region CDR1. CDR2 and/or CDR3; and/or the light chain variable region CDR1, CDR2 and/or CDR3, which are disclosed for the anti-PD-L1, or anti-PD1 or anti-CTLA-4 antibodies or antibody binding fragment in the art. In one embodiment, the second binding region further comprises constant region, e.g., heavy chain constant region and/or light chain constant region, e.g., these disclosed in the disclosure.

In a specific embodiment, the second binding region can bind to human PD-L1, and comprises the $V_H$ and/or $V_L$ disclosed for the anti-PD-L1 antibodies or antibody binding fragment in the art. In another embodiment, the second binding region comprises the heavy chain variable region CDR1, CDR2 and/or CDR3; and/or the light chain variable region CDR1, CDR2 and/or CDR3, which are disclosed for the anti-PD-L1 antibodies or antibody binding fragment in the art. In one embodiment, the second binding region further comprises a constant region, e.g., heavy chain constant region and/or light chain constant region.

It is known that the $V_H$ and/or $V_L$ of the bispecific antibody can be different in one or several amino acids from the $V_H$ and/or $V_L$ of the monoclonal antibody they derives, for the construction of the bispecific antibody. For example, the derived $V_H$ and $V_L$ can have one or more mutations to make the scFv more stable. In one embodiment, the $V_H$ and/or $V_L$ can have a mutation(s) to form disulfide bond with each other so as to make the antibody or its antigen binding portion more stable. For example, the $V_H$ can have a G44C (EU numbering) and the $V_L$ can have a T104C(EU numbering).

In a specific embodiment, the bispecific antibody comprises the following chains:

(1) Chain 1: the heavy chain of the antibody against the second antigen linked to the scFv fragment of anti-4-1BB antibody of the disclosure at N-terminal or C-terminal, via or via not a linker; and (2) Chain 2: the light chain of the antibody against the second antigen.

Figure 5A:
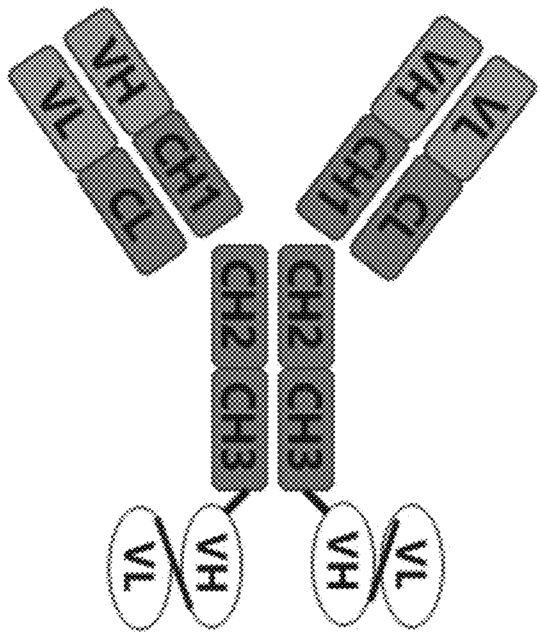
FIG. 5A-5B show the structure of the bispecific antibodies P4B-3 (A) and P4B-2(B).
Figure 5B:
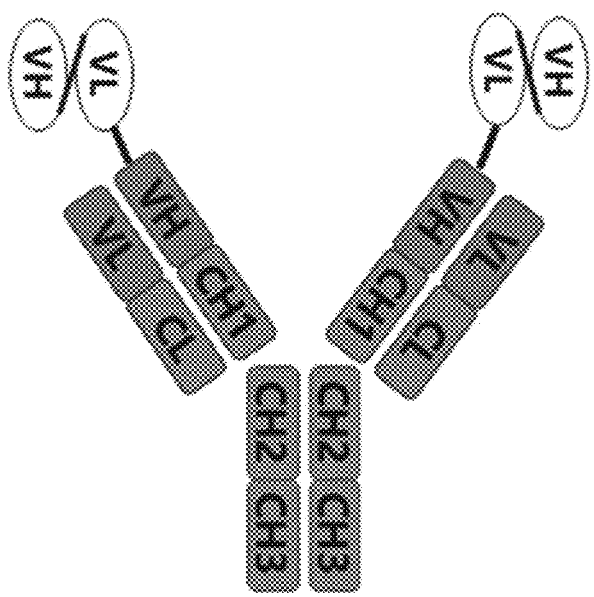

In a specific embodiment, the bispecific antibody comprises two chain 1 and two chain 2 connected by disulfide bond. In a further specific embodiment, the structure of the bispecific antibody is represented in FIG. 5A or FIG. 5B.

Particularly, the heavy chain of the antibody against the second antigen comprises the $V_H$ disclosed for the anti-PD-L1, or anti-PD-1 or anti-CTLA-4 antibodies or antibody binding fragment in the art. In another embodiment, the heavy chain of the antibody against the second antigen comprises the heavy chain variable region CDR1, CDR2 and/or CDR3, which are disclosed for the anti-PD-L1, or anti-PD-1 or anti-CTLA-4 in the art. Particularly, the light chain of the antibody against the second antigen comprises the $V_L$ disclosed for the anti-PD-L1, or anti-PD-1 or anti-CTLA-4 antibodies or antibody binding fragment in the art. In another embodiment, the light chain of the antibody against the second antigen comprises the light chain variable region CDR1, CDR2 and/or CDR3, which are disclosed for the anti-PD-L1, or anti-PD-1 or anti-CTLA-4 in the art.

In one embodiment, the second antigen is PD-L1 and the antibody against to the second antigen is anti-PD-L1 antibody.

In a particular embodiment, the heavy chain of the anti-PD-L1 antibody comprises the heavy chain variable region $V_H$ disclosed for anti-PD-L1 antibody. In a particular embodiment, the $V_H$ comprises heavy chain variable region CDR1, CDR2 and CDR3 disclosed for anti-PD-L1 antibody. In a particular embodiment, the heavy chain comprises heavy chain variable region CDR1, CDR2 and CDR3 disclosed for anti-PD-L1 antibody. In a particularly, the heavy chain further comprises a constant region.

In a particular embodiment, the light chain of the anti-PD-L1 antibody comprises the light chain variable region $V_L$ disclosed for anti-PD-L1 antibody. In a particular embodiment, the $V_L$ comprises light chain variable region CDR1, CDR2 and CDR3 disclosed for anti-PD-L1 antibody. In a particular embodiment, the light chain comprises light chain variable region CDR1, CDR2 and CDR3 disclosed for anti-PD-L1 antibody. In a particularly, the heavy chain further comprises a constant region.

In a specific embodiment, the scFv fragment of anti-4-1BB antibody of the disclosure comprises the $V_H$ and/or $V_L$ disclosed for the anti-4-1BB antibodies or antibody binding fragment herein above. In another embodiment, the scFv comprises the heavy chain variable region CDR1, CDR2 and/or CDR3; and/or the light chain variable region CDR1, CDR2 and/or CDR3, which are disclosed for the anti-4-1BB antibodies or antibody binding fragment herein above.

Particularly, the scFv fragment of anti-4-1BB antibody comprises a heavy chain variable region comprising or consisting of an amino acid sequence represented by SEQ ID NO: 25 or 77, and a light chain variable region consisting of an amino acid sequence represented by SEQ ID No: 26 or 78.

Particularly, the scFv fragment of anti-4-1BB antibody comprises a heavy chain variable region comprising or consisting of an amino acid sequence represented by SEQ ID NO: 77, and a light chain variable region consisting of an amino acid sequence represented by SEQ ID No: 78.

Particularly, the scFv fragment of anti-4-1BB antibody comprises the $V_H$ CDR1, CDR2 and CDR3 consisting of the sequence represented by SEQ ID NO: 1, 2 and 3 respectively, and the $V_L$ CDR1, CDR2 and CDR3 consisting of the sequence represented by SEQ ID NO: 4, 5 and 6 respectively.

Particularly, the linker that connected the $V_H$ and $V_L$ is a flexible linker, such as a linker having glycine and/or serine residues alone or in combination. In one embodiment, the linker comprises the amino acid sequence (Gly4Ser)n or (GlySer4)n, wherein n is a positive integer equal to or greater than 1, for example, n is a positive integer from 1 to 7, for example, n is 2, 3, 4, 5, 6. In one embodiment, n is 1, 2, 3, or 4. In a particular embodiment, the linker comprises or consists of the amino acid sequences represented by SEQ ID NO: 36 or SEQ ID NO: 51 or SEQ ID NO:52.

In a specific embodiment, the heavy chain variable region $V_H$ disclosed for anti-PD-L1 antibody (i) comprises or consists of an amino acid sequence having at least 90%, 91%, 92%, 93%, 94%, 95%, 96%, 97%, 98% or 99% identity with the amino acid sequence selected from the group consisting of SEQ ID NO: 46; or (ii) comprises or consists of an amino acid sequence selected from the group consisting of SEQ ID NO: 46; or (iii) comprises or consists of an amino acid sequence having one or more (preferably no more than 10, more preferably no more than 5) amino acid modifications (preferably amino acid substitutions, more preferably conservative substitutions) compared to an amino acid sequence selected from the group consisting of SEQ ID NO: 46, preferably, said amino acid modifications do not occur in the CDR regions, more preferably, said amino acid modifications occur in FR regions, e.g., FR1, FR2, FR3 or FR4 regions.

In a particular embodiment, the heavy chain variable region CDR1, CDR2 and CDR3 disclosed for anti-PD-L1 antibody are (i) the CDR1, CDR2 and CDR3 derived from the heavy chain variable region, wherein the heavy chain variable region comprises or consists of the sequence represented by SEQ ID NO:46, or (ii) the CDR1, CDR2 and CDR3 of (i), further comprising at least one and no more than 5 amino acid modifications (preferably amino acid substitutions, preferably conservative substitutions) in total compared to the three CDRs of (i).

In a particular embodiment, $V_H$ CDR1 disclosed for anti-PD-L1 antibody comprises or consists of an amino acid sequence selected from the group consisting of SEQ ID NO: 40, or $V_H$ CDR1 comprises or consists of an amino acid sequence having one, two or three modifications (preferably amino acid substitutions, preferably conservative substitutions) compared to the amino acid sequence selected from the group consisting of SEQ ID NO: 40.

In a particular embodiment, $V_H$ CDR2 disclosed for anti-PD-L1 antibody comprises or consists of an amino acid sequence selected from the group consisting of SEQ ID NO: 41, or $V_H$ CDR2 comprises or consists of an amino acid sequence having one, two or three modifications (preferably amino acid substitutions, preferably conservative substitutions) compared to the amino acid sequence selected from the group consisting of SEQ ID NO: 41.

In a particular embodiment, $V_H$ CDR3 disclosed for anti-PD-L1 antibody comprises or consists of an amino acid sequence selected from the group consisting of SEQ ID NO: 42, or $V_H$ CDR3 comprises or consists of an amino acid sequence having one, two or three modifications (preferably amino acid substitutions, preferably conservative substitutions) compared to the amino acid sequence selected from the group consisting of SEQ ID NO: 42.

In one embodiment, the three heavy chain variable regions CDR1, CDR2 and CDR3 disclosed for anti-PD-L1 antibody are (i) the CDR1, CDR2 and CDR3 consisting of the sequence represented by SEQ ID NO: 40, 41 and 42 respectively, or (ii) the CDR1, CDR2 and CDR3 of (i), further comprising at least one and no more than 5 amino acid modifications (preferably amino acid substitutions, preferably conservative substitutions) in total compared to the three CDRs of (i).

In one embodiment, the heavy chain constant region is or is derived from human IgG constant region, e.g., IgG1, IgG2, IgG3 or IgG4, preferable IgG1, IgG2 or IgG4 constant region.

In another embodiment, the heavy chain constant region (i) comprises or consists of an amino acid sequence having at least 80%, 85%, 90%, 91%, 92%, 93%, 94%, 95%, 96%, 97%, 98% or 99% identity with the amino acid sequence represented by SEQ ID NO: 33 or 34 or 75; or (ii) comprises or consists of an amino acid sequence represented by SEQ ID NO: 33 or 34 or 75; or (iii) comprises or consists of an amino acid sequence having one or more (preferably no more than 10, more preferably no more than 5 amino acid modifications (preferably amino acid substitutions, more preferably conservative substitutions) compared to an amino acid sequence represented by SEQ ID NO:33 or 34 or 75.

In a specific embodiment, the light chain variable region $V_L$ disclosed for anti-PD-L1 antibody (i) comprises or consists of an amino acid sequence having at least 90%, 91%, 92%, 93%, 94%, 95%, 96%, 97%, 98% or 99% identity with the amino acid sequence selected from the group consisting of SEQ ID NO: 47; or
(ii) comprises or consists of an amino acid sequence selected from the group consisting of SEQ ID NO: 47; or
(iii) comprises or consists of an amino acid sequence having one or more (preferably no more than 10, more preferably no more than 5) amino acid modifications (preferably amino acid substitutions, more preferably conservative substitutions) compared to an amino acid sequence selected from the group consisting of SEQ ID NO: 47, preferably, said amino acid modifications do not occur in the CDR regions, more preferably, said amino acid changes occur in FR regions. e.g., FR1, FR2, FR3 or FR4 regions.

In a particular embodiment, the light chain variable region CDR1, CDR2 and CDR3 disclosed for anti-PD-L1 antibody are
(i) the CDR1, CDR2 and CDR3 derived from the light chain variable region, wherein the light chain variable region comprises or consists of the sequence represented by SEQ ID NO:47, or
(ii) the CDR1, CDR2 and CDR3 of (i), further comprising at least one and no more than 5 amino acid modifications (preferably amino acid substitutions, preferably conservative substitutions) in total compared to the three CDRs of (i).

In a particular embodiment, $V_L$ CDR1 disclosed for anti-PD-L1 antibody comprises or consists of an amino acid sequence selected from the group consisting of SEQ ID NO: 43, or $V_L$ CDR1 comprises or consists of an amino acid sequence having one, two or three modifications (preferably amino acid substitutions, preferably conservative substitutions) compared to the amino acid sequence selected from the group consisting of SEQ ID NO: 43.

In a particular embodiment, $V_L$ CDR2 disclosed for anti-PD-L1 antibody comprises or consists of an amino acid sequence selected from the group consisting of SEQ ID NO: 44, or $V_L$ CDR2 comprises or consists of an amino acid sequence having one, two or three modifications (preferably amino acid substitutions, preferably conservative substitutions) compared to the amino acid sequence selected from the group consisting of SEQ ID NO: 44.

In a particular embodiment, $V_L$ CDR3 disclosed for anti-PD-L1 antibody comprises or consists of an amino acid sequence selected from the group consisting of SEQ ID NO: 45, or $V_L$ CDR3 comprises or consists of an amino acid sequence having one, two or three modifications (preferably amino acid substitutions, preferably conservative substitutions) compared to the amino acid sequence selected from the group consisting of SEQ ID NO: 45.

In one embodiment, the three light chain variable regions CDR1, CDR2 and CDR3 disclosed for anti-PD-L1 antibody are
(i) the CDR1, CDR2 and CDR3 consisting of the sequence represented by SEQ ID NO: 43, 44 and 45 respectively, or
(ii) the CDR1, CDR2 and CDR3 of (i), further comprising at least one and no more than 5 amino acid modifications (preferably amino acid substitutions, preferably conservative substitutions) in total compared to the three CDRs of (i).

In one embodiment, the light chain constant region is or is derived from kappa or lambda light chain constant region, e.g., human kappa or lambda light chain constant region, preferably human kappa light chain constant region.

In another embodiment, the light chain constant region
(i) comprises or consists of an amino acid sequence having at least 80%, 85%, 90%, 91%. 92%, 93%. 94%. 95%. 96%. 97%, 98% or 99%, identity with the amino acid sequence represented by SEQ ID NO: 35 or 63; or
(ii) comprises or consists of an amino acid sequence represented by SEQ ID NO: 35 or 63; or
(iii) comprises or consists of an amino acid sequence having one or more (preferably no more than 10, more preferably no more than 5) amino acid modifications (preferably amino acid substitutions, more preferably conservative substitutions) compared to an amino acid sequence represented by SEQ ID NO: 35 or 63.

In a particular embodiment, the anti-PD-L1 antibody is the antibody disclosed in CN 109021107 A.

In one embodiment, the linker in the bispecific antibody of the present invention is a flexible linker, such as a linker having glycine and/or serine residues alone or in combination. In one embodiment, the linker comprises the amino acid sequence (Gly4Ser)n or (GlySer4)n, where n is a positive integer equal to or greater than 1, for example, n is a positive integer from 1 to 7, for example, n is 2, 3, 4, 5, 6. In one embodiment, n is 1, 2, 3, or 4, preferably 1 or 3. In a particular embodiment, the linker of the bispecific antibody comprises or consists of the amino acid sequences represented by SEQ ID NO: 36, 51 or 52. In a preferable embodiment, the linker of the bispecific antibody comprises or consists of the amino acid sequences represented by SEQ ID NO: 52, wherein the n=1 or 3.

In one embodiment, chain 1 of the bispecific antibody
(i) comprises or consists of an amino acid sequence having at least 85%. 86%, 87%, 88%, 89% 90%, 91%. 92%, 93%, 94%. 95%, 96', 97%, 98% or 99% identity with the amino acid sequence represented by SEQ ID NO: 48 or 50; or
(ii) comprises or consists of an amino acid sequence represented by SEQ ID NO: 48 or 50; or
(iii) comprises or consists of an amino acid sequence having one or more (preferably no more than 20, more preferably no more than 10 or 5 amino acid modifications (preferably amino acid substitutions, more preferably conservative substitutions) compared to an amino acid sequence represented by SEQ ID NO: 48 or 50.

In one embodiment, chain 2 of the bispecific antibody
(i) comprises or consists of an amino acid sequence having at least 90%, 91%, 92%, 93%, 94%, 95%, 96%, 97%. 98% or 99% identity with the amino acid sequence represented by SEQ ID NO: 49; or
(ii) comprises or consists of an amino acid sequence represented by SEQ ID NO: 49; or
(iii) comprises or consists of an amino acid sequence having one or more (preferably no more than 20, more preferably no more than 10 or 5 amino acid modifications (preferably amino acid substitutions, more preferably conservative substitutions) compared to an amino acid sequence represented by SEQ ID NO: 49.

Conservative Modifications

In another embodiment, an antibody of the disclosure comprises a heavy and/or light chain variable region sequences of CDR1, CDR2 and CDR3 sequences which differ from those of the anti-4-1BB antibodies of the present disclosure by one or more conservative modifications. It is understood in the art that certain conservative sequence modification can be made which do not remove antigen binding. See, e.g., Brummell et al., (1993) *Biochem* 32:1180-8; de Wildt et al., (1997) *Prot. Eng.* 10:835-41; Komissarov et al., (1997) *J. Biol. Chem.* 272:26864-26870; Hall et al., (1992) *J. Immunol.* 149:1605-12; Kelley and O'Connell (1993) *Biochem.* 32:6862-35; Adib-Conquy et al., (1998) *Int. Immunol.* 10:341-6 and Beers et al., (2000) *Clin. Can. Res.* 6:2835-43.

Accordingly, in one embodiment, the antibody comprises a heavy chain variable region comprising CDR1, CDR2, and CDR3 sequences and/or a light chain variable region comprising CDR1, CDR2, and CDR3 sequences, wherein:

(a) the heavy chain variable region CDR1 sequence comprises a sequence listed in Table 1 above, and/or conservative modifications thereof; and/or (b) the heavy chain variable region CDR2 sequence comprises a sequence listed in Table 1 above, and/or conservative modifications thereof; and/or (c) the heavy chain variable region CDR3 sequence comprises a sequence listed in Table 1 above, and conservative modifications thereof; and/or (d) the light chain variable region CDR1, and/or CDR2, and/or CDR3 sequences comprise the sequence(s) listed in Table 1 above; and/or conservative modifications thereof; and (e) the antibody specifically binds human 4-1BB.

In another embodiment, an antibody of the disclosure comprises a heavy and/or light chain variable region sequences which differ from those of the anti-4-1BB antibodies of the present disclosure by one or more conservative modifications, preferably, the modification does not occur in CDR, preferably, the modification occurs in FR.

In another embodiment, an antibody of the disclosure comprises a heavy and/or light chain sequences which differ from those of the anti-4-1BB antibodies of the present disclosure by one or more conservative modifications, preferably, the modification does not occur in CDR, preferably, the modification occurs in FR, or occurs in constant region.

In some embodiment, the modification is incorporated into the FR of the heavy chain variable region and/or the light chain variable region for the construction of the multispecific antibodies. e.g., the bispecific antibodies. For example, the modification can be incorporated into the heavy chain variable region and/or the light chain variable region to form a disulfide bond with each other, so as to improve the stability of the scFv which can be constructed into the bispecific antibodies In some embodiments, the modification is substitution, addition and/or deletion.

In some embodiments, the substitution is a conservative substitution. A conservative substitution refers to a replacement of an amino acid by another amino acid of the same class. e.g., an acidic amino acid replacement by another acidic amino acid, a basic amino acid replacement by another basic amino acid, or a neutral amino acid replacement by another neutral amino acid. Exemplary substitutions are shown in Table below:

| Original residue | Conservative substitution | Preferable conservative substitution |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |

-continued

| Original residue | Conservative substitution | Preferable conservative substitution |
|---|---|---|
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Trp, Leu, Val, Ile, Ala, Tyr | Tyr |
| Pro (P) | Ala | Ala |
| Ser (S) | Thr | Thr |
| Thr (T) | Val, Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

The antibody of the present disclosure possesses one or more of the following functional properties described above, such as specifically binding to human 4-1BB.

In various embodiments, the antibody can be, for example, a mouse, human, humanized or chimeric antibody.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

Engineered and Modified Antibodies

Antibodies of the disclosure can be prepared using an antibody having one or more of the $V_H/V_L$ sequences of the anti-4-1BB antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) *Nature* 332:323-327; Jones et al., (1986) *Nature* 321:522-525; Queen et al., (1989) *Proc. Natl. Acad*. See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1. CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCol2 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637). 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or live residues within a CDR region are altered.

Accordingly, in another embodiment, the disclosure provides isolated anti-4-1BB monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or live amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcal protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704. Ms705, and Ms709 lack the fucosyltransferase gene, FUT8 (α(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 200401 10704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the α-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as *Lemna*. Methods for production of antibodies in a plant system are disclosed in the U.S. patent application corresponding to Alston & Bird LLP, filed on Aug. 11, 2006. PCT Publication WO 99/54342 describes cell lines engineered to express glycoprotein-modifying glycosyl transferases (e.g., β(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) *Nat. Biotech.* 17:176-180). Alternatively, the fucose residues of the antibody can be cleaved off using a fucosidase enzyme; e.g., the fucosidase α-L-fucosidase removes fucosyl residues from antibodies (Tarentino et al., (1975) *Biochem.* 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EPO 154 316 and EP 0 401 384.

Antibody's Physical Properties

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316:452-7; Mimura et al., (2000) *Mol Immunol* 37:697-706). Glycosylation has been known to occur at motifs containing an NX-Sir sequence. In some instances, it is preferred to have an anti-4-1BB antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a link into the polypeptide chain and decreases its stability (isoaspartic acid effect).

Each antibody will have a unique isoelectric point (pI) which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions.

Thus, it is preferred to have an anti-4-1BB antibody that contains a pI value that falls in the normal range. This can be achieved either by selecting antibodies with a pI in the normal range or by mutating charged surface residues.

Nucleic Acid Molecules Encoding Antibodies of the Disclosure

In another aspect, the disclosure provides nucleic acid molecules that encode heavy and/or light chain variable regions, or CDRs, or heavy chain and/or light chain or the whole chains of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the 4-1BB monoclonal antibody or the CDRs. Preferred nucleic acid molecules? of the disclosure further include those encoding the $V_H$, $V_L$, or each chain of the multiple-specific antibody, e.g., bispecific antibody. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene, or to multispecific (bispecitic) antibody chain genes. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

In one embodiment, an exemplary nucleic acid of the invention includes a nucleic acid encoding an amino acid sequence selected from any one of SEQ ID NOs: 25-32, 48, 50, 77 and 78, or a nucleic acid encoding an amino acid sequence having at least 85%, 90%, 91%, 92%, 93%, 94%, 95%, 96%, 97%, 98%, or 99% identity to an amino acid sequence selected from any one of SEQ ID NOs: 25-32, 48, 50, 77 and 78.

In another embodiment, the nucleic acid of the present invention comprises nucleotide sequences selected from any one of SEQ ID NO: 65, 66, 73, 74, 79 or 80, or a nucleotide sequences having at least 85%, 90%, 91%, 92%, 93%, 94%, 95%, 96%, 97%, 98%, or 99% identity to a nucleotide sequence selected from any one of SEQ ID NO: 65, 66, 73, 74, 79 or 80.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1, IgG2 or IgG4 constant region, or the constant region with a mutation. e.g., constant region comprising or consisting of a sequence represented by SEQ ID NO: 33, 34, or 75, or sequences having at least 80%, 85%, 90%, 95%, 96%, 97%, 98% or 99% identity thereof. For a Fab fragment heavy chain gene, the $V_H$-encoding DNA can be operatively linked to another DNA molecule encoding only the heavy chain $C_{H3}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region, e.g., the light chain constant region comprising or consisting of a sequence represented by SEQ ID NO: 35 or 63, or sequences having at least 80%, 85%. 90%, 95%. 96%, 97%, 98% or 99% identity thereof.

To create a scFv gene, the $V_H$- and $V_L$-encoding DNA fragments are operatively linked to another fragment encoding a flexible linker, e.g., encoding the amino acid sequence $(Gly4\text{-}Ser)_3$ or $(Gly\text{-}Ser4)_3$, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Production of Antibodies of the Disclosure

The present invention provides a process for the production of an antibody of the present invention, said process comprising culturing a host cell of the present invention under conditions allowing the expression of the antibody and recovering the produced antibody construct from the culture.

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Bispecitic antibodies of the present disclosure can be constructed using the well-known platform for the bispecific antibodies, according to the format of the bispecific antibodies. There are several methods known in the art to produce the bispecific methods, for example, as described in U.S. Pat. No. 4,816,567 and in U.S Publication No. 2013/0078249, which is incorporated herein by reference in its entirety.

Generation of Transfectomas Producing Antibodies of the Disclosure

Antibodies of the disclosure also can be produced in a host cell transfectoma using, for example, a combination of recombinant DNA techniques and gene transfection methods as is well known in the art (e.g., Morrison, S. (1985) Science 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described. e.g., in Goeddel (Gene Expression Technology. Methods in Enzymology 185, Academic Press. San Diego. Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell. e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include 293 cells, Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Pharmaceutical Composition

In another aspect, the present disclosure provides a pharmaceutical composition comprising one or more antibodies (or antigen-binding portion thereof, or the bispecific molecules) of the present disclosure formulated together with a pharmaceutically acceptable carrier. The antibodies (or antigen-binding portion thereof, or the bispecific molecules) can be dosed separately when the composition contains more than one antibody (or antigen-binding portion thereof, or the bispecific molecules). The composition may optionally contain one or more additional pharmaceutically active ingredients, such as therapeutic agent, such as another antibody or a drug, such as an anti-cancer drug, an anti-microbial drug, or an anti-asthma drug, e.g., a chemotherapeutic agent, cytotoxic agent, vaccines, other antibodies (e.g., antibodies against to immune checkpoint molecule, e.g., PD-1), anti-infection agents, small molecule drugs, or immunomodulators.

The term "therapeutic agent" as described herein encompasses any substance effective in preventing or treating tumors (such as cancer), including chemotherapeutic agents, cytotoxic agents, vaccines, other antibodies (e.g., antibodies against to the immune checkpoint molecule), anti-infection agents, immunomodulators, or small molecule drugs.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients are taught in Gennaro, ed., Remington: *The Science and Practice of Pharmacy.* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration. e.g., intranasally, orally, vaginally, rectally, sublingually or topically.

Pharmaceutical compositions can be in the form of sterile aqueous solutions or dispersions. They can also be formulated in a microemulsion, liposome, or other ordered structure suitable to high drug concentration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99.0% of active ingredient, preferably from about 0.1% to about 70%, most preferably from about 1.0% to about 30.0% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the composition, the dosage may range from about 0.0001 to 100.0 mg/kg, and more usually 0.01 to 5.0 mg/kg, of the host body weight. For example, dosages can be 0.3 mg/kg body weight, 1.0 mg/kg body weight, 3.0 mg/kg body weight, 5.0 mg/kg body weight or 10.0 mg/kg body weight or within the range of 1.0-10.0 mg/kg. An exemplary treatment regime entails administration once per week, once every two weeks, once every three weeks, once every four weeks, once every month, once every 3 months or once every three to 6 months. Preferred dosage regimens for an anti-4-1BB antibody of the disclosure include 1.0 mg/kg body weight or 3.0 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1.0-1000.0 μg/ml and in some methods about 25.0-300.0 μg/ml.

A "therapeutically effective dosage" of an anti-4-188 antibody, or the antigen-binding portion thereof, or the bispecific molecules of the disclosure preferably results in a decrease in severity of disease symptoms, an increase in frequency and duration of disease symptom-free periods, or a prevention of impairment or disability due to the diseased affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker. Inc., New York, 1978.

Pharmaceutical compositions can be administered via medical devices such as (0.1) needleless hypodermic injection devices (e.g., U.S. Pat. Nos. 5,399,163; 5,383,851; 5,312,335; 5,064,413; 4,941,880; 4,790,824; and 4,596,556): (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224): and (5) osmotic devices (U.S. Pat. Nos. 4,439,196 and 4,475,196): the disclosures of which are incorporated herein by reference.

In certain embodiments, the antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

Combination Product

In another aspect, the present disclosure provides a combination product comprising one or more antibodies (or antigen-binding portion thereof, or the bispecific molecules) of the present disclosure and one or more additional therapeutic agent, such as another antibody or a drug, such as an anti-cancer drug, an anti-microbial drug, or an anti-asthma drug, e.g., a chemotherapeutic agent, cytotoxic agent, vaccines, other antibodies (e.g., antibodies against to immune checkpoint molecule, e.g., PD-1), anti-infection agents, small molecule drugs, or immunomodulators.

The "combination product" refers to a fixed or non-fixed combination of dosage unit forms or a kit of parts for combined administration in which two or more therapeutic agents can be administered independently at the same time or administered separately within a time interval, especially when these time intervals allow the combined partner to demonstrate collaboration, for example, synergistic effects. The term "fixed combination" means that the antibody of the invention and the combination partner (e.g., other therapeutic agents, such as immunomodulators, such as immunosuppressive agents or anti-inflammatory agents) are administered to a patient simultaneously in the form of a single entity or dose. The term "non-fixed combination" means that the antibodies and combination partners of the present invention (e.g., other therapeutic agents, such as immunomodulators, such as immunosuppressive agents or anti-inflammatory agents) are administered to patients simultaneously, concurrently, or sequentially as separate entities, and there is no specific time limitation, where such administration provides therapeutically effective levels of the two compounds in the patient. The latter also applies to cocktail therapy, such as the administration of three or more therapeutic agents. In a preferred embodiment, the drug combination is a non-fixed combination.

Uses and Methods

The composition comprising the antibodies or the antigen-binding portion thereof, or the bispecific molecules of the present disclosure have numerous in vitro and in vivo utilities involving, for example, treatment of cancers, infections, and autoimmune diseases. The antibodies can be administered to human subjects, e.g., in vivo, to alleviate these diseases.

In one aspect, the present invention provides a method for modulating an immune response in a subject.

In another aspect, the present invention provides a method for activating T cells or inducing T cell mediated antitumor activity. In one embodiment, the T cells are the CD8+T cells. In another aspect, the present invention provides a method for decreasing the Treg cells, e.g., CD4+T cells.

In one embodiment, the activation of the T cells includes stimulating the cytokine secretion of the T cells, e.g., the IL-12 secretion of T cells.

In one embodiment, the present invention provides a method for activating the 4-1BB signaling pathway.

In some embodiments, the methods above comprise administering the antibody or antigen binding fragments, the pharmaceutical composition or formulation, the combination product or the nucleic acid of the present invention.

In one aspect, the antibody of the present invention is the bispecific antibody which binds to 4-1BB and PD-L1, as described above.

In one embodiment, the present invention provides a method for treating cancer in a subject, comprising administering the bispecific antibody that binds to 4-1BB and PD-L1 of the present disclosure, or the pharmaceutical composition or combination product comprising thereof.

In some embodiment, the cancer is a tumor immune escape.

In some embodiments, the cancer, includes solid cancers and non-solid cancers and metastatic lesions. In one embodiment, examples of solid cancers include malignant tumors. The cancer can be early, middle, or advanced or metastatic cancer. In some embodiments, the cancer is a cancer that requires T cell activation, such as cancer with T cell dysfunction.

In some embodiments, the cancer is a cancer having increased level of PD-L1 protein expression or increased level of nucleic acid encoding PD-L1, e.g., compared to the level in the normal subject or the normal cell.

Preferably, said cancer is cancer in gastrointestinal tract, e.g., colorectal cancer, rectal cancer or colon cancer.

In some embodiments, the treatment of the cancer will benefit from (i) inhibition of PD-L1 nucleic acid or protein levels;

(ii) blocking the binding of PD-L1 to its receptor, such as PD-1, (iii) the activation of 4-1BB signaling pathway;

(iv) the activation of T cells, e.g., increasing the proliferation of CD8+ T cells, or decreasing the Treg cells, e.g., CD4+ T cells;

(v) a combination of anyone or more of the above.

In another aspect, the disclosure provides methods of combination therapy in which the anti-4-1BB antibodies, or antigen-binding portion thereof, or the bispecific molecules of the present disclosure are co-administered with one or more therapeutic agents, e.g., additional antibodies that are effective in alleviate cancers, infections or autoimmune diseases in a subject. In one embodiment, the disclosure provides a method for treating a cancer disease in a subject comprising administering to the subject an anti-4-1BB antibody (or antigen-binding portion thereof, or the bispecific antibody) and one or more therapeutical agents, e.g., additional antibodies, such as an anti-PD-1 antibody, an anti-PD-L1 antibody, and/or an anti-CTLA-4 antibody. In certain embodiments, the subject is human.

The 4-1BB signaling activation can also be further combined with standard disease treatments. For example, 4-1BB signaling activation can be combined with administration of the antibodies mentioned above or chemical anti-cancer drugs.

Therefore, the combination therapy comprises the combination of the co-administration of the anti-4-1BB antibodies, or antigen-binding portion thereof, or the bispecific molecules of the present disclosure, and the pharmaceutical composition and combination product thereof, and other therapies. e.g., a therapeutic modality and/or other therapeutic agent, preferably the therapeutic modality includes surgery and/or radiation therapy, and/or the other therapeutic agent is selected from the group consisting of a chemotherapeutic agent, other antibody, cytotoxic agent, vaccine, anti-infection agents, small molecule drugs, or immunomodulators.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the sane order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1 Phage Panning, Screening and Affinity Maturation

Phage Library

An antibody single chain phage display library was created by cloning a repertoire of light chain variable regions (VL) and a repertoire of heavy chain variable regions (VH). The heavy and light chain repertoires were created by PCR amplification from human lymphocytes mainly collected from peripheral blood. The VL repertoire and VH repertoire were mixed and underwent PCR with overlapping primers. The final format of the antibody was a single chain Fv (scFv) with VH and VL fragments joined by a flexible linker peptide (GGGGSGGGGSGGGGS (SEQ ID NO.: 36)).

Phage Library Panning Against Human 4-1BB

Selection of phage particles displaying specific scFv fragments was performed on Immuno 96 MicroWell™ Plates (Nunc, Denmark). First, 50 μg/mL 4-1BB recombinant protein (Sinobiological. Cat #10041-108H) in phosphate-buffered saline (PBS) was coated on the plates overnight at 4° C. Following blocking the plates with 2% (w/v) milk powder in PBS (2% MPBS), a library containing about $10^{11}$ phage particles were added and the plate was incubated for 2 hours at room temperature (RT. 25-28° C.). Non-bound phages were removed by washing plates 10-20 times with PBS containing 0.1% Tween 20 (PBST), followed by 10-20 times washing with PBS. The bound phages were eluted by incubation with 50 μl of 1 μg/μl trypsin for 10 min, followed by 50 μl of 50 mM glycine-HCl pH 2.0 for 10 min, then immediately neutralized with 50 μL of 2(X) mM $Na_2HPO_4$, pH 7.5. Four rounds of panning were performed.

Phage Screening

From the third and fourth rounds of panning, phages were picked up and tested for human 4-1BB binding. In specific, human 4-1BB (Sinobiological, Cat #10041-H08H) were coated on 96-well plates at 0.1 μg/mL, and single clone phages were added into plates. Then, unbound phages were washed away and bound phages were detected by anti-M13 secondary antibody (Abcam, Cat #ab50370).

ELISA positive clones were sequenced, from which 28 unique sequences were identified, including clone 41BB-2, 41BB-9, 41BB-13 and 41BB-27. The amino acid sequence ID numbers of the heavy/light chain variable regions and its CDRs (defined according to Kabat numbering) of exemplary anti-4-1BB antibodies were shown in Table 2. With these heavy/light chain variable region sequences, full antibodies 41BB-2, 41BB-9, 41BB-13 and 41BB-27 were prepared having the human IgG2(SEQ ID NO:33) or IgG1 (SEQ ID NO:34) or IgG4 heavy chain constant region (SEQ ID NO: 75) and the human light chain lambda constant region (SEQ ID NO: 35), wherein the C-terminus of the heavy chain variable region was linked to the N-terminus of the heavy chain constant region, and the C-terminus of the light chain variable region was linked to the N-terminus of the light chain constant region, wherein the light chain variable region of the antibody 41BB-2 contained an amino acid sequence of SEQ ID NO.: 26, X1=S.

In addition, the light chain variable region of 41BB-2 antibody has a mutation from S to G at the last site and connected to an IgG1 heavy chain constant region (SEQ ID NO:34). The obtained 41BB-2 with modifications can be prepared in a higher purity than 41BB-2 with IgG1 heavy chain constant region (SEQ ID NO:34) (data not shown).

TABLE 2

Sequences ID of the full antibodies

| | 41BB-2-IgG2 | 41BB-2-IgG1 | 41BB-9-IgG2 | 41BB-9-IgG1 | 41BB-13-IgG2 | 41BB-13-IgG1 | 41BB-27-IgG2 | 41BB-27-IgG4 |
|---|---|---|---|---|---|---|---|---|
| HCDR1 | 1 | 1 | 7 | 7 | 13 | 13 | 19 | 19 |
| HCDR2 | 2 | 2 | 8 | 8 | 14 | 14 | 20 | 20 |
| HCDR3 | 3 | 3 | 9 | 9 | 15 | 15 | 21 | 21 |
| VH | 25 | 25 | 27 | 27 | 29 | 29 | 31 | 31 |
| Heavy chain constant region | 33 | 34 | 33 | 34 | 33 | 34 | 33 | 75 |
| LCDR1 | 4 | 4 | 10 | 10 | 16 | 16 | 22 | 22 |
| LCDR2 | 5 | 5 | 11 | 11 | 17 | 17 | 23 | 23 |
| LCDR3 | 6 | 6 | 12 | 12 | 18 | 18 | 24 | 24 |
| VL | 26(X1 = S) | 26(X1 = G) | 28 | 28 | 30 | 30 | 32 | 32 |
| Light chain constant region | 35 | 35 | 35 | 35 | 35 | 35 | 35 | 35 |

The antibodies with the above sequences are prepared and purified with common method known in the art. To be specific, nucleotide sequences encoding the heavy chain and light chain of antibodies were inserted into the expression vector pcDNA3.1 (Invitrogen). Vectors were co-transfected into CHO-S cells using ExpiCHO™ Expression System (ThermoFisher) according to manufacturer's instructions. The transfected cells were cultured in ExpiCHO™ Expression Medium for 12 days, and then culture supernatants were harvested and sent for purification with Protein A affinity chromatography (GE healthcare) according to manufacturer's instruction.

Example 2 Binding of Exemplary Anti-4-1BB Antibodies to Human 4-1BB

An ELISA assay was performed for determination of the relative binding capacities of the antibodies to human 4-1BB.

Human 4-1BB (Sinobiological, Cat #10041-H08H) in carbonate buffer solution pH 9.6 was immobilized onto 96-well plates by incubation overnight at 4° C., 25 ng/well. The plates were then blocked by incubation with 1% BSA in PBS for one hour at 37° C. After blocking, the plates were washed three times with PBST (PBS containing 0.05% Tween20). Serially diluted anti-4-1BB antibodies and Urelumab control (prepared according to WO2005035584, using the heavy and light chain amino acid sequences set forth in SEQ ID Nos.: 37 and 38) were respectively prepared in binding buffer (PBS containing 0.05% Tween20 and 0.5% BSA) and incubated in the plates with the immobilized proteins for one hour at 37° C. After binding, the plates were washed three times with PBST, incubated for one hour at 37° C. with peroxidase-labeled Goat Anti-Human IgG F(ab')$_2$ antibody (Jackson Immuno Research, Cat #109-035-097) diluted 1/20,000) in binding buffer, washed again, developed with TMB (ThermoFisher Cat #34028) for 15 minutes, and then stopped with 1 M $H_2SO_4$. Each plate well contained 50 μL of solution at each step.

The absorbance at 450 nm-620 nm was determined. The $EC_{50}$ values and binding curves for the antibodies binding to human 4-1BB were shown in FIG. 1A to 1D, suggesting the anti-4-1BB antibodies 41BB-2-IgG2, 41BB-9-IgG2, 41BB-13-IgG2 and 41BB-27-IgG2 specifically bound to human 4-1BB with higher binding capacities than the Urelumab control.

Example 3 Cross Reactivity of Exemplary Anti-4-1BB Antibodies with Rhesus 4-1BB but not with Human CD40, Human HVEM, Human OX40, Human CD27 or Human GITR ELISA assays were done to determine the binding activities of the exemplary anti-4-1BB antibodies to recombinant human CD40, human HVEM, human OX40, human CD27, human GITR or Rhesus 4-1BB.

Human CD40 (Sinobiological, Cat #10774-H08H), human HVEM (Sinobiological, Cat #10334-H03H), human OX40 (Sinobiological, Cat #10481-H08H), human CD27 (Sinobiological, Cat #10039-H31H), human GITR (Sinobiological, Cat #13643-H08H) and Rhesus 4-1BB (Sinobiological, Cat #90847-K08H) in carbonate buffer solution pH 9.6 were immobilized onto 96-well plates, respectively, by incubation overnight at 4° C., 25 ng/well.

The plates were then blocked by incubation with 1% BSA in PBS for one hour at 37° C. Afterwards, the plates were washed three times with PBST (PBS containing 0.05% Tween20). Anti-4-1BB antibodies and the Urelumab were respectively prepared in binding buffer (PBS containing 0.05% Tween20 and 0.5% BSA), 500 ng/mL, and incubated with the immobilized proteins for one hour at 37° C. After binding, the plates were washed three times with PBST, incubated for one hour at 37° C. with peroxidase-labeled Anti-Human IgG F(ab')$_2$ antibody (Jackson Immuno Research, Cat #109-035-097) diluted 1/20,000 in binding buffer, washed again, developed with TMB (ThermoFisher Cat #34028) for 15 minutes, and then stopped with 1M $H_2SO_4$. Each plate well contained 50 μL of solution at each step.

Figure 2A:
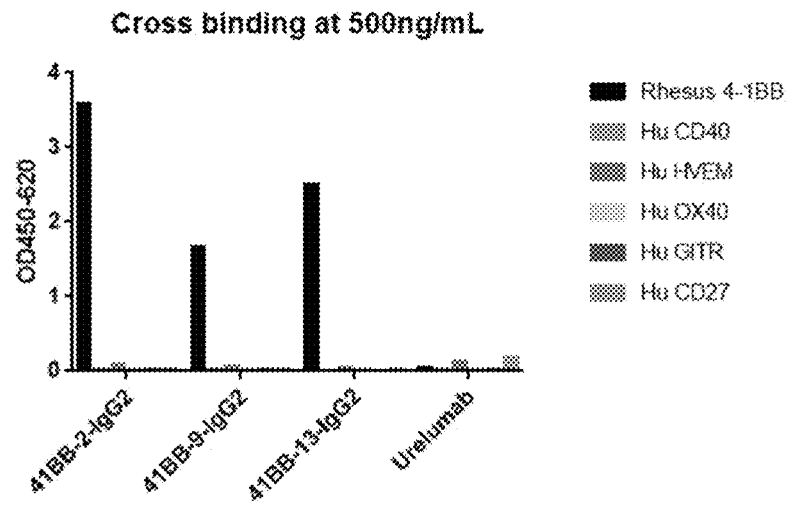
FIGS. 2A and 2B show the binding capacities of anti-4-1BB antibodies 41BB-2-IgG2, 41BB-9-IgG2, 41BB-13-IgG2 (A) and 41BB-27-IgG2 (B) to human CD40, human HVEM, human OX40, human CD27, human GITR and Rhesus 4-11313 in ELISA assay.
Figure 2B:
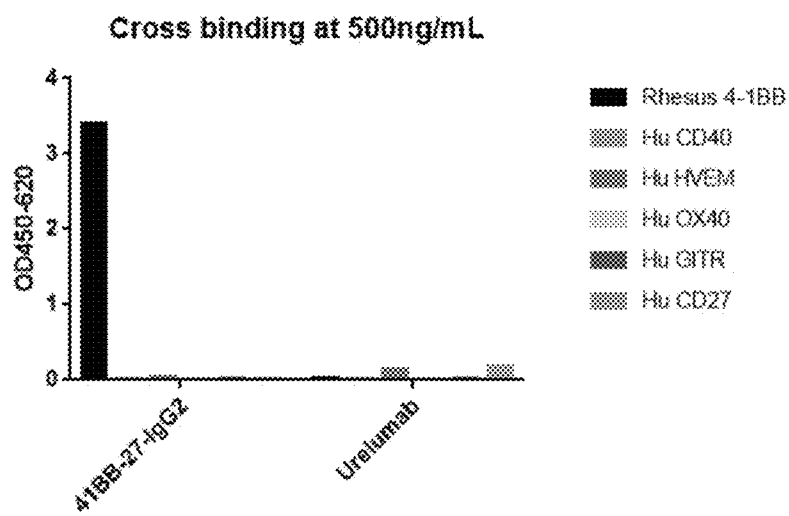
Figure 3A:
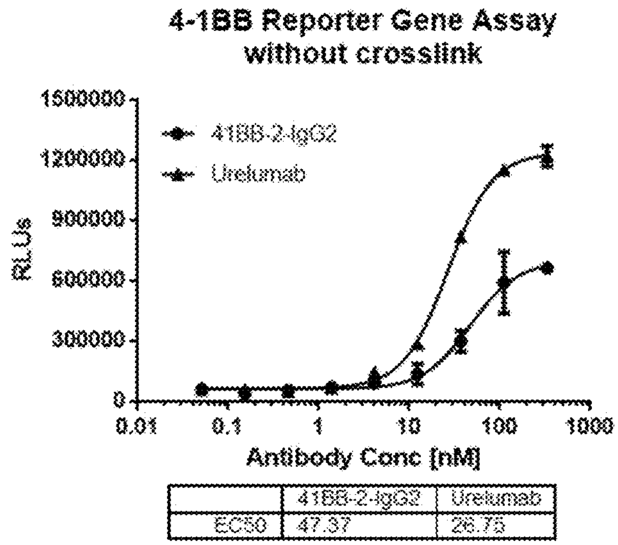
FIG. 3A-3G show the agonistic activities of anti-4-1BB antibodies 41BB-2-IgG2, 41BB-9-IgG2, 41BB-13-IgG2 and 41BB-27-IgG2 on 4-1BB signaling with or without crosslink.
Figure 3B:
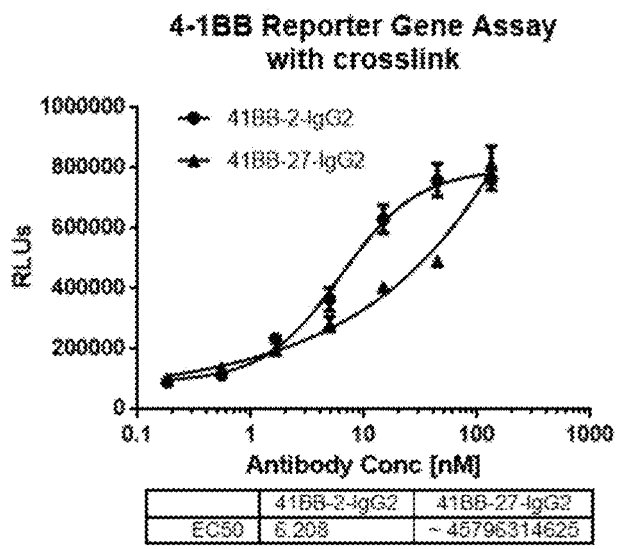
Figure 3C:
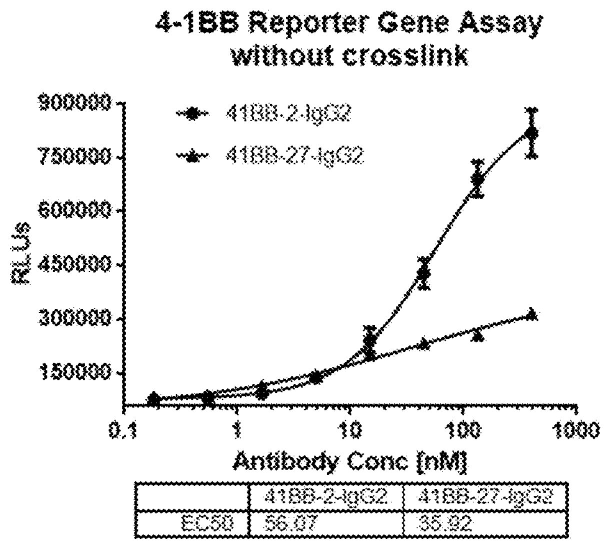
Figure 3D:
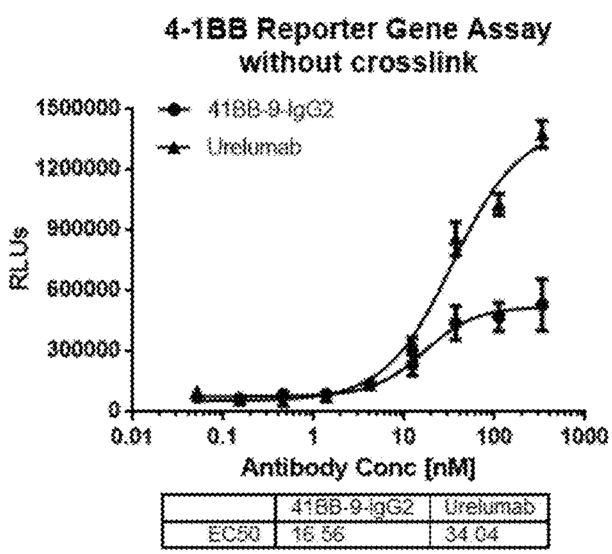
Figure 3E:
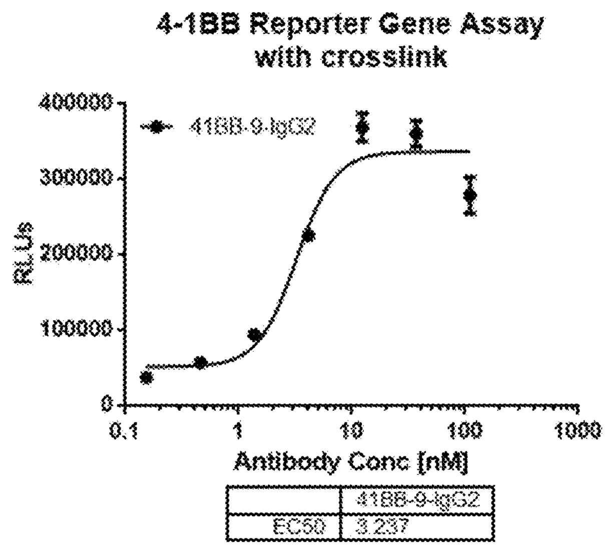
Figure 3F:
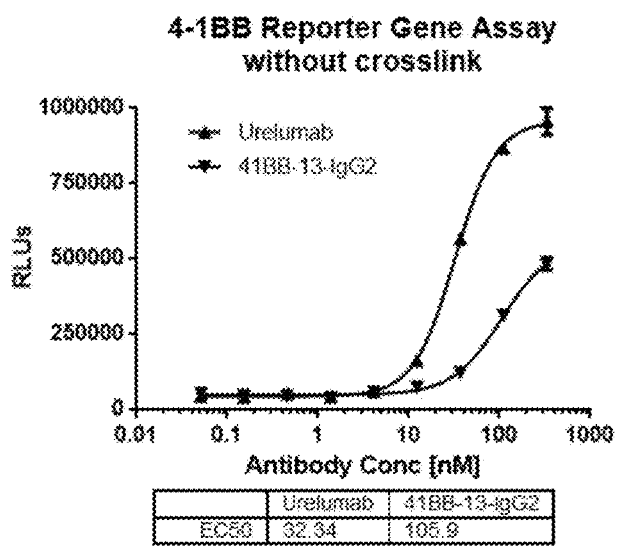
Figure 3G:
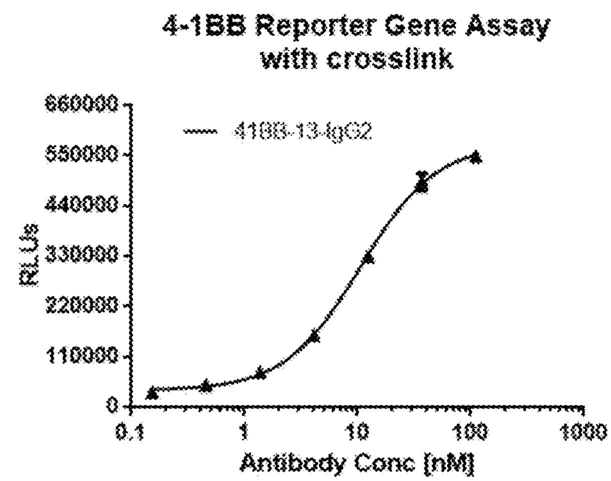

The absorbance at 450 nm-620 nm was determined and shown in FIG. 2A to 2B. It can be seen that the anti-4-1BB antibodies 41BB-2-IgG2, 41BB-9-IgG2, 41BB-13-IgG2 and 41BB-27-IgG2 did not bind to human CD40, human HVEM, human OX40, human CD27 or human GITR, but cross-reacted with Rhesus 4-1BB. The Urelumnab did not bind to any of these proteins.

Example 4 Binding of Exemplary Anti-4-1BB Antibodies to Cell Surface 4-1BB and Induction of NFκB Report Gene Luminescence Signal The agonistic effects of the exemplary anti-4-1BB antibodies on human 4-1BB signaling were assessed in a HEK293-NFκB-Luc-human 4-1BB report gene assay.

The Full antibodies 41BB-2-IgG2, 41BB-9-IgG2, 41BB-13-gG2, 41BB-27-IgG2, 41BB-9-IgG1, 41BB-13-IgG1, 41BB-27-IgG4, 41BB-2-IgG1 were prepared and purified in Example 1.

The full antibodies of 41BB-2-IgG2, 41BB-9-IgG2, 41BB-13-IgG2, 41BB-27-IgG2 were assessed as follows:

Briefly, a HEK293 cell line (ATCC, Cat #CRL-1573) was maintained in DMEM medium containing 10% FBS in a humidified incubator with 5% $CO_2$ at 37° C. Nucleic acid sequences encoding human 4-1BB (amino acid of NP_001552.2 as set forth in SEQ ID NO.: 39) and pGL4.32 [luc2P/NF-κB-RE/Hygro] (Promega, Cat #E849A) were co-transfected to HEK293 cells using Lipofectamine™ 2000 Transfection Reagent (Invitrogen, Cat #11668019), and a clone stably expressing human 4-1BB and NF-κB-Luc was obtained by limited dilution. The obtained HEK293-NFκB-Luc-4-1BB cells in DMEM containing 10% FBS were plated into the 96-well plates (50000 cells/well) on Day 1 and cultured in $CO_2$ incubator overnight. On Day 2, the medium on the 96-well plates was discarded, and then serially diluted anti-4-1BB antibodies or the Urelumab in DMEM containing 1% FBS, pretreated with 2-fold concentration of Goat Anti-Human IgG (Jackson Immuno Research, Cat #109-005-098) or not, were added to the plates and co-cultured with the HEK293-NFκB-Luc-4-1BB cells. The plates were incubated in a 37° C., 5% $CO_2$ incubator for six hours. Then 60 μL of One-Glo™ Reagent (Promega, Cat #E6130) was added to the wells of the assay plates and luminescence was measured using a luminescence plate reader (Tecan F200 Pro). The $EC_{50}$ values were determined, and the representative curves for the anti-4-1BB antibodies were shown in FIG. 3A to 3G.

The Goat Anti-Human IgG reacted with the Fc portion of the anti-4-1BB antibodies to make two or more anti-4-1BB antibodies cross-linked together. The formation of antibody dimers or polymers might contribute to better agonistic effects on 4-1BB signaling.

The results indicated that 41BB-2-IgG2, 41BB-9-IgG2, 41BB-13-IgG2 and 41BB-27-IgG2 can all bound to 4-1BB expressed on the cell surface and accordingly activated the 4-1BB signaling and induce NFκB report gene luminescence expression, whether they were cross-linked or not. However, without cross-link, the 4-1BB antibodies of the present invention has much lower agonistic effects on human 4-1BB signaling while they have higher agonistic effects with the presence of cross-link. The agonistic effect of the four 4-1BB clones is depended on Fc cross-linking.

Figure 4A:
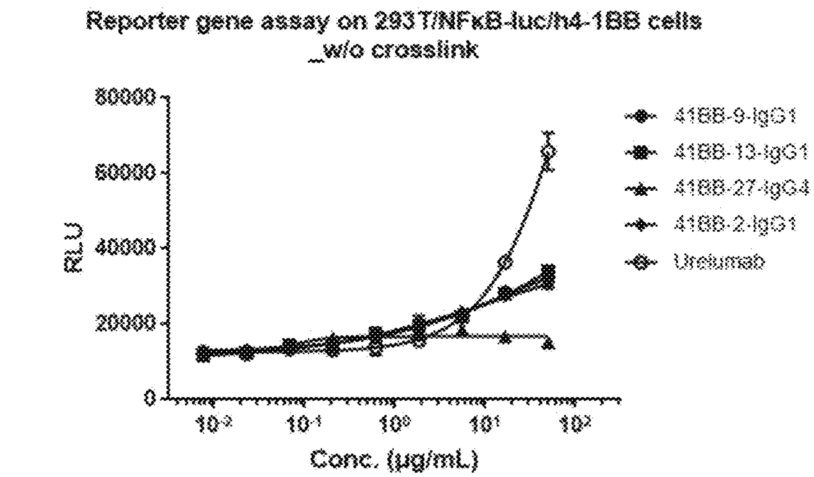
FIG. 4A-4B show the agonistic activities of anti-4-1BB antibodies 41BB-2-IgG1, 41BB-9-IgG1, 41BB-13-IgG1 and 41BB-27-IgG4 on 4-1BB signaling with or without crosslinker.
Figure 4B:
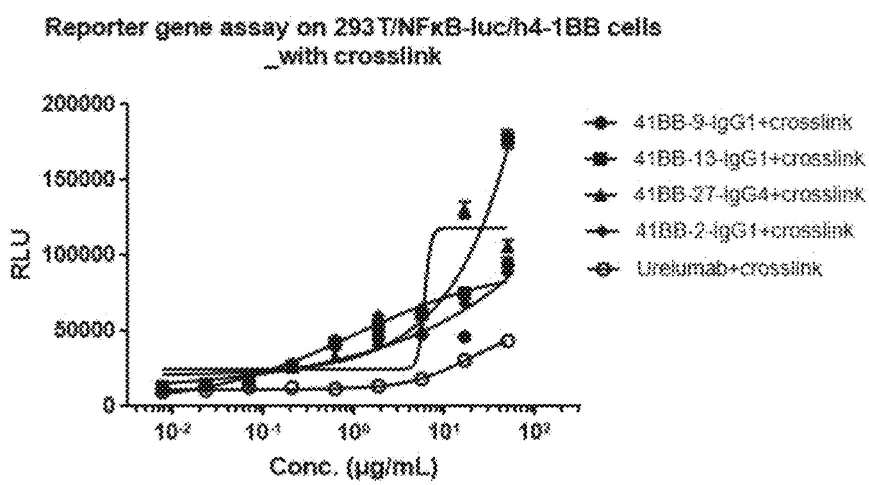

The full antibodies 41BB-9-IgG1, 41BB-13-IgG1, 41BB-27-IgG4, 41BB-2-IgG1 were verified as follows:

Briefly, a HEK293 cell line (ATCC. Cat #CRL-1573) was maintained in DMEM medium containing 10% FBS in a humidified incubator with 5% $CO_2$ at 37° C. Nucleic acid sequences encoding human 4-1BB (amino acid of NP_0.001552.2 as set forth in SEQ ID NO.: 39) in pIRE-Spuro3 plasmid and pGL4.32[luc2P/NF-κB-RF/Hygro] (Promega, Cat #E849A) were co-transfected to HEK293 cells using Lipofectamine™ 2000 Transfection Reagent (Invitrogen, Cat #11668019), and a clone stably expressing human 4-1BB and NF-κB-Luc was obtained by limited dilution after screening with puromycin (Gibco, Cat #A1113802) and hygromycin. The obtained HEK293-NFκB-Luc-human 4-1BB cells in DMEM containing 10% FBS were plated into the 384-well plates (20000 cells/well in 40 μL). Then 10 μL/well serially diluted anti-4-1BB antibodies 41BB-9-IgG1, 41BB-13-IgG1, 41BB-27-IgG4, 41BB-2-IgG1 or the Urelumab (starting from 50 μg/mL, in a 3-fold dilution series) in DMEM containing 10% FBS, pretreated with Goat Anti-Human IgG diluted in a two-fold dilution series (Jackson Immuno Research, Cat #109-005-098) or not, were added to the plates. The plates were incubated in a 37° C. 5% $CO_2$ incubator for six hours. After the incubation, 30 μL of One-Glo™ Reagent (Promega, Cat #E6130) was added to the wells of the assay plates and luminescence was measured using a luminescence plate reader (Tecan P200 Pro). The results can be seen in FIG. 4A-4B.

The Goat Anti-Human IgG reacted with the Fc portion of the anti-4-1BB antibodies to make two or more anti-4-1BB antibodies cross-linked together.

The results indicated that in the presence of the cross-linker, 41BB-2-IgG1, 41BB-9-IgG1, 41BB-13-IgG1 except 41BB-27-IgG4 would activate the human 4-1BB signaling and induce much higher NFκB report gene signal than that of the Urelumab. While without crosslinker, the four 4-1BB antibodies induced much lower NFκB report gene signal than that of Urelumab. The agonistic effect of the four 4-1BB clones is depended on Fc cross-linking.

Example 5 Expression and Purification of Bi-Specific Antibodies

Two bispecific antibodies, P4B-2 and P4B-3 were constructed. Their structures were shown in FIG. 5B (P4B-2) and FIG. 5A (P4B-3).

To be specific, the bispecific P4B-2 is constructed as follows, the two scFvs of 4-1BB antibody is linked to the N-terminals of the two heavy chains of the whole PD-L1 antibodies respectively, to construct a bispecific antibodies comprising

- a heavy chain consisting of from N terminal to C terminal:
- VH from 4-1BB antibody (VH of anti-4-1BB)-linker-VL from 4-1BB antibody (VL of anti-4-1BB)-linker-VH from PD-L1 antibody (VH of anti-PD-L1)-heavy chain constant region; and
- a light chain from PD-L1 antibody (Light chain of anti-PDL1. i.e., VL of anti-PD-L1-light chain constant region).

The bispecific P4B-3 is constructed as follows, the two scFvs of 4-1BB antibody is linked to the C-terminals of the two heavy chains of the whole PD-L1 antibodies respectively, to construct a bispecific antibodies comprising a heavy chain consisting of from N-terminal to C-terminal:

- VH from PD-L1 antibody (VH of anti-PD-L1)-heavy chain constant region-linker-VH from 4-1BB antibody (VH of anti-4-1BB VH)-linker-VL from 4-1BB antibody (VL of anti-4-1BB); and
- a light chain from PD-L1 antibody (light chain of anti-PDL1, i.e., VL of anti-PD-L1-light chain constant region).

Nucleotides encoding bispecific antibodies and controls were generated by gene synthesis (Genscript) and cloned into the expression vector pcDNA3.1 (Invitrogen). The nucleic acid encoding the light chain variable region is inserted into the expression vector pcDNA3.1 (Invitrogen) containing a nucleic acid encoding a light chain constant region to construct the vectors expressing the light chain of the antibody, and the nucleic acid encoding heavy chain variable region is inserted into the expression vector pcDNA3.1 (Invitrogen) containing a nucleic acid encoding a heavy chain constant region to construct the vectors expressing the heavy chain of the antibody, respectively. The obtained vectors were co-transfected in a molar ratio of 1:1 into CHO-S cells using ExpiCHO™ Expression System (ThermoFisher, Cat #A29133) according to manufacturer's instructions. The transfected cells were cultured in ExpiCHO™ Expression Medium for 12 days, and then culture supernatants were harvested and sent for purification with Protein A affinity chromatography (GE healthcare) according to manufacturer's instructions.

The amino acid sequences and nucleic acid sequences of the different regions can be seen in Table 3.

TABLE 3

SEQ ID NO of the regions/domains of the bispecific antibodies.

| | P4B-2 (amino acid sequence ID/ nucleic acid sequence ID) | P4B-3 (amino acid sequence ID/ nucleic acid sequence ID) |
|---|---|---|
| VH-CDR1 of PDL1 antibody | 40/53 | 40/53 |
| VH-CDR2 of PDL1 antibody | 41/54 | 41/54 |
| VH-CDR3 of PDL1 antibody | 42/55 | 42/55 |
| VL-CDR1 of PDL1 antibody | 43/56 | 43/56 |
| VL-CDR2 of PDL1 antibody | 44/57 | 44/57 |
| VL-CDR3 of PDL1 antibody | 45/58 | 45/58 |
| VH of anti-PD-L1 | 46/59 | 46/59 |
| VL of anti-PD-L1 | 47/60 | 47/60 |
| VH-CDR1 of anti-4-1BB | 1/67 | 1/67 |
| VH-CDR2 of anti-4-1BB | 2/68 | 2/68 |
| VH-CDR3 of anti-4-1BB | 3/69 | 3/69 |
| VL-CDR1 of anti-4-1BB | 4/70 | 4/70 |
| VL-CDR2 of anti-4-1BB | 5/71 | 5/71 |
| VL-CDR3 of anti-4-1BB antibody | 6/72 | 6/72 |
| VH of anti-4-1BB [1] | 77/79 | 77/79 |
| VH of anti-4-1BB[2] | 78/80 | 78/80 |
| linker between scFv of anti-4-1BB and anti-PD-L1 | 52, n = 1 | 52, n = 3 |
| linker between VH of anti-41BB and VL of anti-4-1BB | 51 | 51 |
| Heavy chain | 48/65 | 50/66 |
| Light chain | 49/76 | 49/76 |
| Heavy chain constant region of anti-PD-L1 | 34/85 | 34/85 |
| Light chain constant region of anti-PD-L1 (Kappa) | 63/64 | 63/64 |

[1] the 4-1BB VH is derived from the VH of mononclonal antibody 41BB-2 by the G44C (EU numbering) to form disulfide bond with the VL so as to improve the scFv stability.
[2] the 4-1BB VL is derived from the VL of mononclonal antibody 41BB-2 by the T104C (EU numbering) to form disulfide bond with VH so as to improve the scFv stability.

Example 6 Antibodies Bound to Human PD-L1 and 4-1BB Protein

Figure 6:
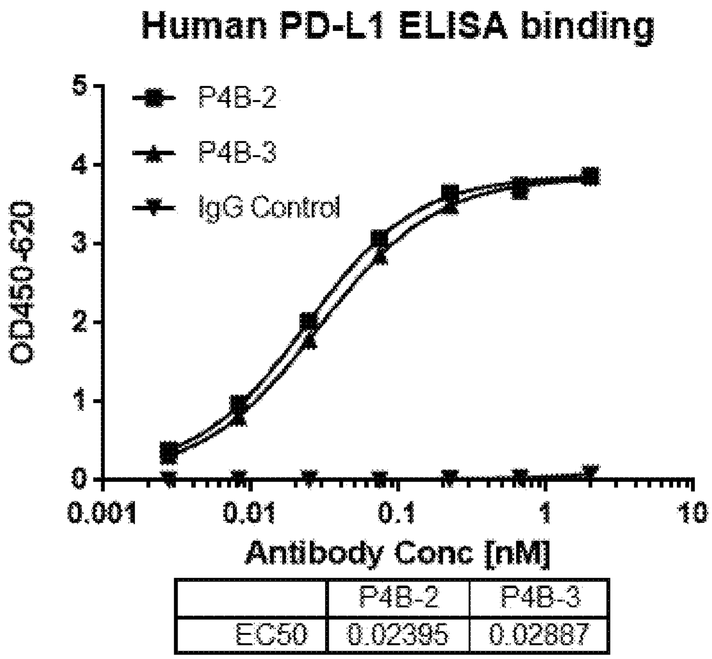
FIG. 6 shows the bispecific antibodies' binding to human PD-L1 in ELISA assay.

Human PD-L1, His tag protein (ACRO, Cat #PD1-1H15229) was immobilized onto 96-well plates (Hangzhou Xinyou. Cat #100096H) by incubation with Carbonate buffer (pH 9.6) overnight at 4° C. The plates were then blocked by incubation with 1% BSA in PBS for one hour at 37° C. After blocking, the plates were washed three times with PBST (PBS containing 0.05% Tween20). Serially diluted from 2 nM to 0.003 nM P4B-2, P4B-3 and negative control IgG (heavy chain: SEQ ID NO:82; light chain: SEQ ID NO:83) were prepared in dilution buffer (PBS containing 0.05% Tween20 and 0.5% BSA) and incubated with the immobilized protein above for one hour at 37° C. Then, the plates were washed three times with PBST, incubated for one hour at 37° C. with Peroxidase AffiniPure Goat Anti-Human IgG, Fcγ fragment specific (Jackson ImmunoResearch, Cat #109-035-098) diluted at 1/20,000 in the dilution buffer, and then washed with PBST again. TMB (Thermo, Cat #34028) was added into the plates to initiate the reaction. After 15 minutes, the reaction was stopped with 1M $H_2SO_4$. The absorbance at 450 nm-620 nm was determined. The EC50 and representative binding curves for the antibodies' binding to human PD-L1 were shown in FIG. 6.

The results indicated that the two antibodies P4B-2 and P4B-3 could both bind to human PD-L1 proteins, with the EC50 of 0.02395 nM and 0.02887 nM, respectively.

Figure 7:
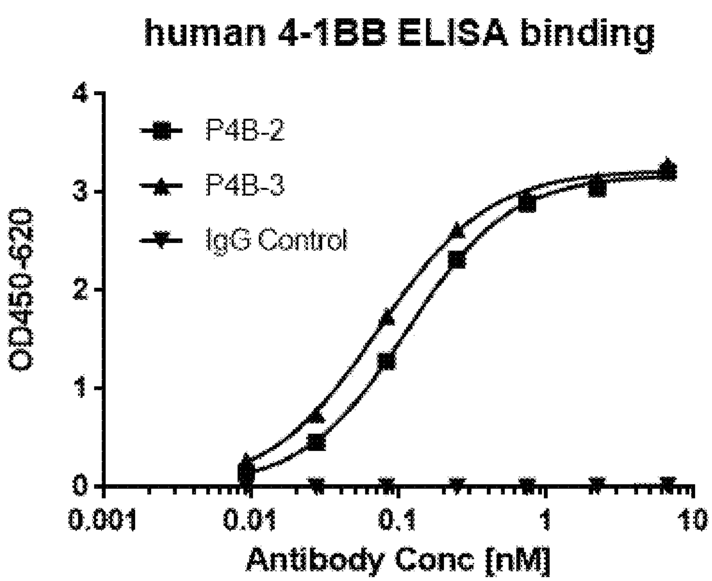
FIG. 7 shows bispecific antibodies' binding to human 4-1BB in ELISA assay.

Human 4-1BB, human Fc tag protein (SEQ ID NO:81, Hu4-1BB-hFc) was immobilized onto 96-well plates (Hangzhou Xinyou, Cat #100096H) by incubation with Carbonate buffer (pH 9.6) overnight at 4° C. The plates were then blocked by incubation with 1% BSA in PBS for one hour at 37° C. After blocking, the plates were washed three times with PBST (PBS containing 0.05% Tween20). Serially diluted from 6.65 nM to 0.009 nM P4B-2, P4B-3 and negative control IgG (heavy chain: SEQ ID NO:82; light chain: SEQ ID NO:83) were prepared in dilution buffer (PBS containing 0.05% Tween20 and 0.5% BSA) and incubated with the immobilized protein Hu4-1BB-hFc for one hour at 37° C. Then, the plates were washed three times with PBST, incubated for one hour at 37° C. with Peroxidase AffiniPure Goat Anti-Human IgG, $F(ab')_2$ fragment specific (Jackson ImmunoResearch, Cat #109-035-097) diluted at 1/10,000 in dilution buffer, and then washed with PBST again. TMB (Thermo, Cat #34028) was added into plates to initiate the reaction. After 10 minutes, the reaction was stopped with 1M $H_2SO_4$. The absorbance at 450 nm-620 nm was determined. The EC50 and representative binding curves for the clones binding to human 4-1BB were shown in FIG. 7.

The results indicated that two antibodies P4B-2 and P4B-3 could both bind to human 4-1BB proteins, with the EC50 of 0.1126 nM and 0.07234 nM respectively.

Therefore, the two bi-specific antibodies P4B2 and P4B3 can bind to both human PD-L1 and human 4-1BB protein, with low EC50.

Example 7 Binding Affinities

The Binding Affinity to PD-L1 Proteins

The kinetic binding activity of P4B-3 antibody to human PD-L1 protein (ACRO, Cat #PD1-H5229) and cynomolgus monkey PD-L1 protein (Sino Biological, Cat #90251-C08H) was measured by ForteBio Octet RED 96 (Fortebio).

The P4B-3 antibody was coated to pre-equilibrated Anti-Human IgG Fc Capture (AHC) bio-sensors (Fortebio, Cat #18-5060). Human PD-L1 (ACRO, Cat #PD1-H5229) and cynomolgus monkey PD-L1 (Sino Biological, Cat #90251-C08H) proteins were used as analyte and captured by the antibody. The data sets were fitted with a 1:1 Binding Model using Octet software.

Table 4 summarized the affinities of the bispecific antibody of the present invention P4B-3 to human and cynomolgus monkey PD-L1 protein.

TABLE 4

Affinities of P4B-3 to recombinant human and cynomolgus monkey PD-L1

| Sample | Antigen | $K_D$(M) | $K_{on}$($M^{-1}S^{-1}$) | $K_{off}$($S^{-1}$) | Full R^2 |
|---|---|---|---|---|---|
| P4B-3 | human PD-L1 | 2.89E−10 | 5.40E+05 | 1.56E−04 | 0.9924 |
| | cynomolgus PD-L1 | 6.08E−11 | 9.70E+05 | 5.89E−05 | 0.9958 |

The results suggested that the antibody P4B-3 can specifically bind to both human PD-L1 and cynomolgus monkey PD-L1, with $K_D$ of 0.29 nM and 0.061 nM respectively.

The Binding Affinity to 4-1BB Proteins

The kinetic binding activity of P4B-3 antibody to human 4-1BB protein (Sino Biological, Cat #10041-H08H) was measured by ForteBio Octet RED 96 (Fortebio).

The anti-4-1BB antibody was coated to pre-equilibrated Anti-Human IgG Fc Capture (AHC) bio-sensors (Fortebio, Cat #18-5060). Human 4-188 (Sino Biological, Cat #10041-H08H) was used as analyte and captured by the antibody. The data sets were fitted with a 1:1 Binding Model using Octet software.

Table 5 summarized the affinities of the anti-human 4-1BB antibody to human 4-1BB proteins.

TABLE 5

Affinities of P4B-3 to recombinant human 4-1BB

| Sample | Antigen | $K_D$(M) | $K_{on}$($M^{-1}S^{-1}$) | $K_{off}$($S^{-1}$) | Full R^2 |
|---|---|---|---|---|---|
| P4B-3 | human 4-1BB | 1.46E−7 | 2.80E+4 | 4.09E−3 | 0.8444 |

The result, suggested that the antibody P4B-3 could bind to human 4-1BB proteins, with the EC50 of 1.46E-7M.

Example 8, 4-1BB Reporter Gene Assay of P4B-3 on HEK293-4-1BB/NFκB System

The activation of P4B-3 bispecific antibody was evaluated in PD-L1-dependent 4-1BB reporter gene system. HEK293-NFκB-Luc-human 4-1BB cell line and A375-PD-L1 target cell line and CHO-K1-PDL-1 cell line were developed by Leadsbiolabs in house.

HEK293-NFκB-Luc-human 4-1BB cell line is obtained according to the procedure specified in Paragraph [00222]. Example 4.

A375 (Cell Bank, Type Culture Collection. Chinese Academy of Sciences, Cat #SCSP-533) parent cell line was transfected with human PD-L1 gene (SEQ ID NO:62, encoding amino acid sequence of SEQ ID NO:61) using Lipofectamine™ 2000 Transfection Reagent (Invitrogen, Cat #11668019). Stable single cell clone highly expressed human PD-L1 was selected after screening with puromycin (Gibco, Cat #A1113802) to obtain A375-PD-L1 cells.

CHO-K1(ATCC Cat #CCL-61) parent cell line was transfected with human PD-L1 gene (SEQ ID NO:62, encoding amino acid sequence of SEQ ID NO:61) using Lipofectamine™ 2000 Transfection Reagent (Invitrogen, Cat #11668019). Stable single cell clone highly expressed human PD-L1 was selected after screening with puromycin (Gibco, Cat #A1113802) to obtain CHO-K1-PDL1 cells.

The expression of luciferase directly correlates with the activity of 4-1BB.

HEK293-NFκB-Luc-human 4-1BB cells and A375-PD-L1 cells were collected and diluted to suitable cell density with assay buffer (DMEM+1% FBS starting from 10 nM, 4 dilutions) respectively, the two cells are mixed such that the cell density of HEK293-4-1BB/NFκB cells is 40000 cells/60 μL, the density of A375-PD-L1 cells is 20000 cells/60 μL. The mixtures were added 60 μL/well to a 96-well plate (Corning, Cat #3917). In the parallel assay to test the target cells independent stimulation, only HEK293-NFκB-Luc-human 4-1BB cells were added to another 96-well plate (Corning, Cat #3917).

Then 60 μL/well serially diluted test samples P4B-3 and INBRX-105-1 (PD-L1×4-1BB bispecific antibody. SEQ ID NO:84, US20170198050A1) (start from 200 nM, in a 5 fold dilution series, having 9 concentrations) were added to the obtained plates. After incubation in 37° C. incubator for 6 hours. 60 μL/well of One-Glo (Promega, Cat #E6130) reagents were added to the plates. Relative luminescence units were measured with a luminometer (Tecan, Cat #F200).

Figure 9A:
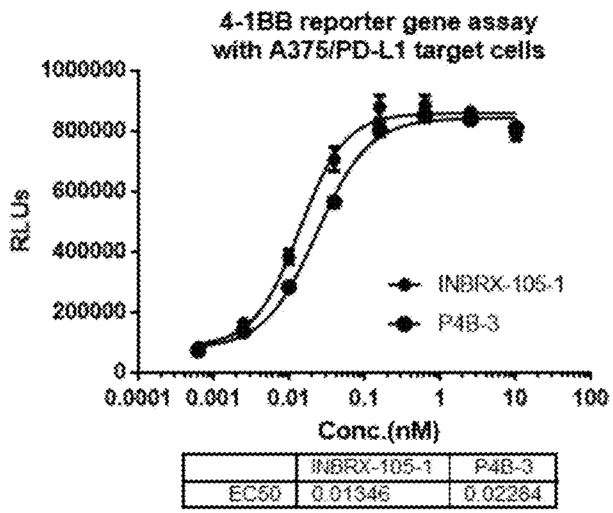
FIGS. 9A and B show the ability of bispecific antibodies (P4B-3 and INBRX-105-1) to induce 4-1BB stimulation in the 4-1BB reporter gene assay with and without target cells A375/PD-L1.
Figure 9B:
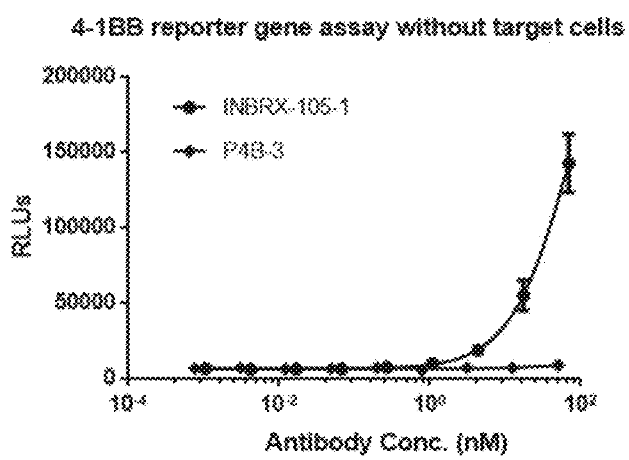

FIG. 9A-9B demonstrates the ability of PD-L1×4-1BB bispecific antibodies (P4B-3 and INBRX-105-1) to induce 4-1BB stimulation without PD-L1. P4B-3 could not stimulate 4-1BB signal pathway without PD-L1 while the INBRX-105-1 control can stimulate the signal pathway at high assay concentrations (FIG. 9B).

HEK293-NFκB-Luc-human 4-1BB cells and CHO-K1-PD-L1 cells were also collected and diluted to suitable cell density with assay buffer (DMEM+1% FBS) respectively, the two cells are mixed and the cell density of HEK293-NFκB-Luc-human 4-1BB cells is 40000 cells/60 μL, the density of CHO-K1-PD-L1 cells is 20000 cells/60 μL. The mixtures were added 60 μL/well to a 96-well plate (Corning, Cat #3917).

Then 60 μL/well serially diluted test samples P4B-3 and NM21-PRO1186 (PD-L1×4-1BB bispecific antibody, WO2019072868A1) (start from 200 nM, in a 5 fold dilution series, having 9 concentrations) were added to the obtained plates. After incubation in 37° C. incubator for 6 hours. 60 μL/well of One-Glo (Promega, Cat #E6130) reagents were added to the plant s. Relative luminescence units were measured with a luminometer (Tecan, Cat #F200).

Figure 8:
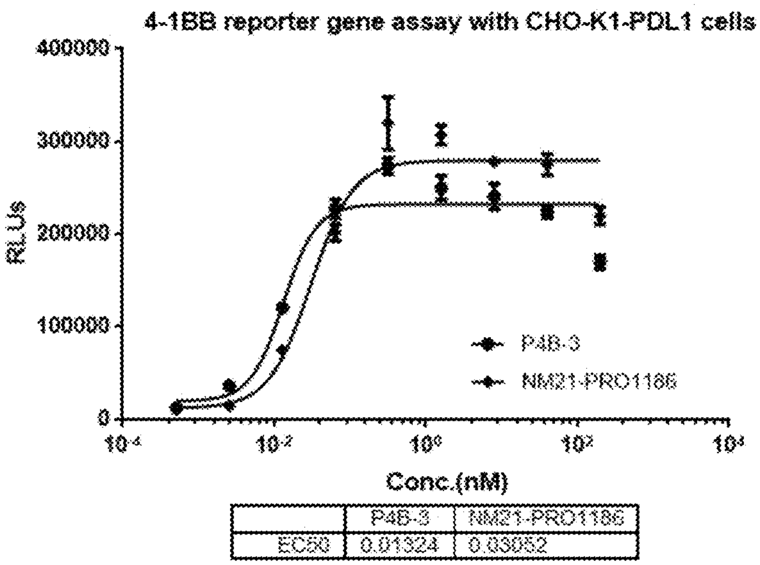
FIG. 8 shows the ability of bispecific antibodies (P4B-3 and NM21-PRO1186) to induce PD-L1-binding-dependent 4-11313 stimulation in the 4-1BB reporter gene assay with target cells CHO-K1-PDL1 cells.

FIG. 8 demonstrates the ability of PD-L1×4-1BB bispecitic antibodies (P4B-3 and NM21-PRO1186) to induce PD-L1-binding-dependent 4-1BB stimulation. Results showed that both P4B-3 and NM21-PRO1186 can stimulate 4-1BB signal pathway in the presence of PD-L1, i.e., dependent to their binding to PD-L1. Their agonistic activities are comparable. These results indicated that the activating ability of P4B-3 on HEK293-NFκB-Luc-human 4-1BB reporter gene was strictly depended on its binding to PD-L1.

Example 9 In Vitro Human PBMC Cells Activation

Human peripheral blood mononuclear cells (PBMC) were obtained from healthy donors. Mononuclear cells were isolated in SepMate-50 tubes (StemCell Technologies) containing Lymphoprep density gradient reagent (StemCell Technologies). Both cells are frozen in liquid nitrogen for later use.

96-well plates (Corning, Cat #3799) were coated with 0.2 μg/mL functional-grade anti-CD3 (eBioscience, Cat #16-0037-85) at 4° C. for overnight. Next day, the coated plates were washed twice with DPBS buffer (Hyclone. SH30256.01).

PBMC cells (Donor 712023) were quickly thawed in a 37° C. water bath and the cell suspension was transferred to a tube containing warm complete medium (90% RPMI 1640 (Gibco, Cat #22400)+10% FBS (Gibco, Cat #10099-141)). Then the cells were centrifuged at 300 g for 5 min. The supernatant was discarded and PBMC cells were re-suspended in complete medium (90% RPMI 1640+10% FBS) and adjusted to $1\times10^6$ cells/mL.

Target cells Raji/PD-L1 is prepared as follows: Raji parent cell line (Cell Bank, Type Culture Collection, Chinese Academy of Sciences, Cat #TCHu 44) was infected with human PD-L1 gene (SEQ ID NO: 62, encoding amino acid sequence of SEQ ID NO:61) packaged in Lentivirus system (GeneCopoeia™, Cat #LT001). Stable single cell clone highly expressing human PD-L1 was selected after screening with puromycin (Gibco, Cat #A1113802) to obtain Raji/PD-L1 cells.

After incubation, target cells Raji/PD-L1 were harvested by centrifugation at 300 g for 5 min. Discard the supernatant and gently suspend the target cells in complete medium (90% RPMI 1640+10% FBS) to $1\times10^6$ cells/mL. The antibodies P4B-3. Anti-PD-L1 (HUL02 from CN109021107A), 41BB-2-IgG1 prepared in Example 1, Anti-PD-L1+41BB-2(ratio 1:1), and human IgG negative control (heavy chain SEQ ID NO:82, light chain: SEQ ID NO:83) were serially diluted to prepare test sample solutions (final concentrations of 0.05 nM, 0.5 nM, 5 nM and 50 nM).

Figure 10:
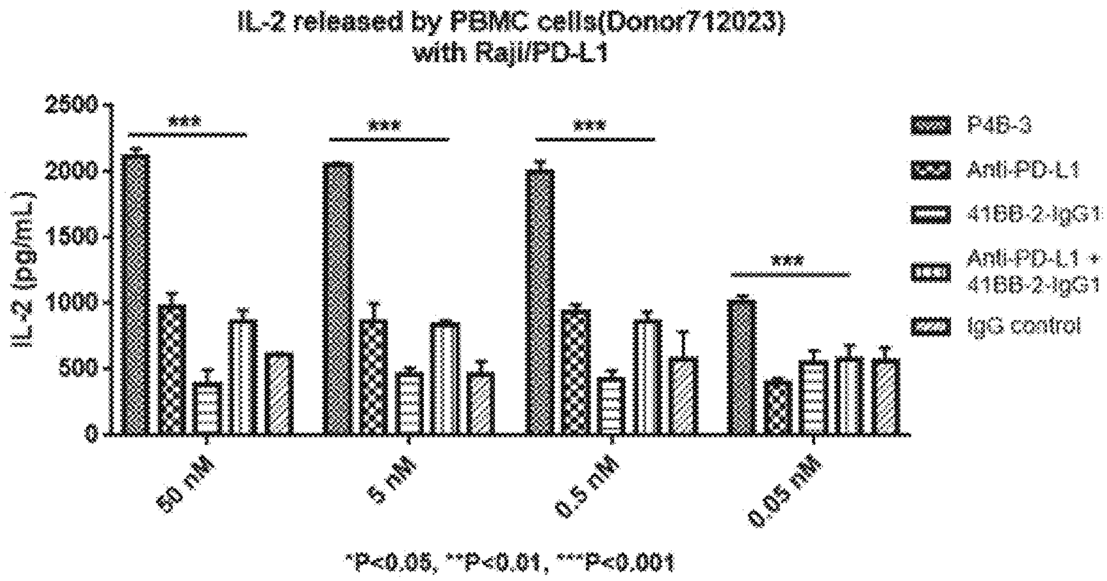
FIG. 10 shows that P413-3 activated human PBMC to release IL-2.

Next, 50.000 cells/well of Raji/PD-L1 were added to the coated 96-well assay plate, and 50 L/well of each of the test sample solutions were added, followed by addition of 100.000 cells/well of PBMC in complete medium. After 72 hours of incubation at $37^1$C and 5% $CO_2$, cell supernatants were harvested and human Interleukin-2 (IL-2) levels in the culture supernatants were quantified with ELISA kit (R&D, Cat #DY202) according to the manufacture's instructions. Results were shown in FIG. 10.

The results showed that P4B-3 stimulated PBMC cells in a dose dependent manner to release higher level of IL-2 than using Anti-PD-L1 alone, Anti-4-1BB(41BB-2-IgG1mut) alone, or the combination of Anti-PD-L1 and Anti-4-1BB.

Example 10 Anti-Tumor Efficacy of P4B-3 in huPD-L1/Hu4-1BB KI Mice Model Bearing MC38-hPD-L1

BALB/c-huPD-L1/hu4-1BB double knock-in mice (Biocytogen) of 6-7 weeks were subcutaneously implanted with $5\times10^5$ MC38-huPD-L1 cells (Biocytogen), and were randomized into 4 groups on Day 0 when the mean tumor volumes reached approximately 87 nm (Length×Width$^2$/2).

On Day 0, 3, 6, 9, 12, 15, mice were intraperitoneally administered with P4B-3, anti-PD-L1 antibody (HUL02 from CN109021107A), 41BB-2-IgG1 and vehicle (PBS) respectively. Tumor volumes were monitored by caliper measurement twice per week during the study.

Compared to the vehicle group, P4B-3 showed very significant tumor inhibitory effect ($P<0.001$), with TGI (Tumor Growth Inhibition) of tumor volume=81.8%, higher than anti-PD-L1 group (TGItv=70.5%) and anti-4-1BB group (TGItv=46.1%). The average tumor weight of P4B-3 is also significantly lower than the vehicle group ($P<0.05$).

At the end of the study, TILs (Tumor infiltrating lymphocytes) were isolated from the tumors and stained with different cell marker antibody (Brilliant Violet 510™ anti-mouse CD45 (Biolegend, Cat #103138), PerCP/Cy5.5 anti-mouse TCR β chain (Biolegend, Cat #109228), Brilliant Violet 421™ anti-mouse CD4 (Biolegend, Cat #100438), Brilliant Violet 711™ anti-mouse CD8a (Biolegend, Cat #100748). PE anti-mouse/rat Foxp3, eBioscience (Thermo, Cat #12-5773-82)), then detected by FACS.

Compared to vehicle group and anti-PD-L1 group, the ratio of CD8+ T cells in CD3+ T cells in P4B-3 group was significantly higher ($P<0.05$), while the ratio of Treg cells in CD3+ cells was significantly lower ($P<0.05$).

Figure 11:
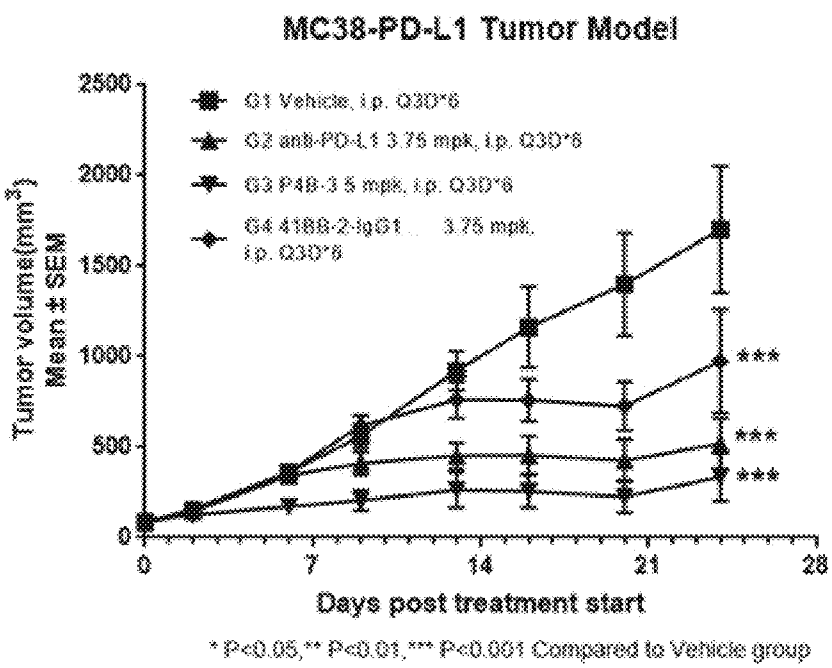
FIG. 11 shows the tumor growth curve after treatment.
Figure 12:
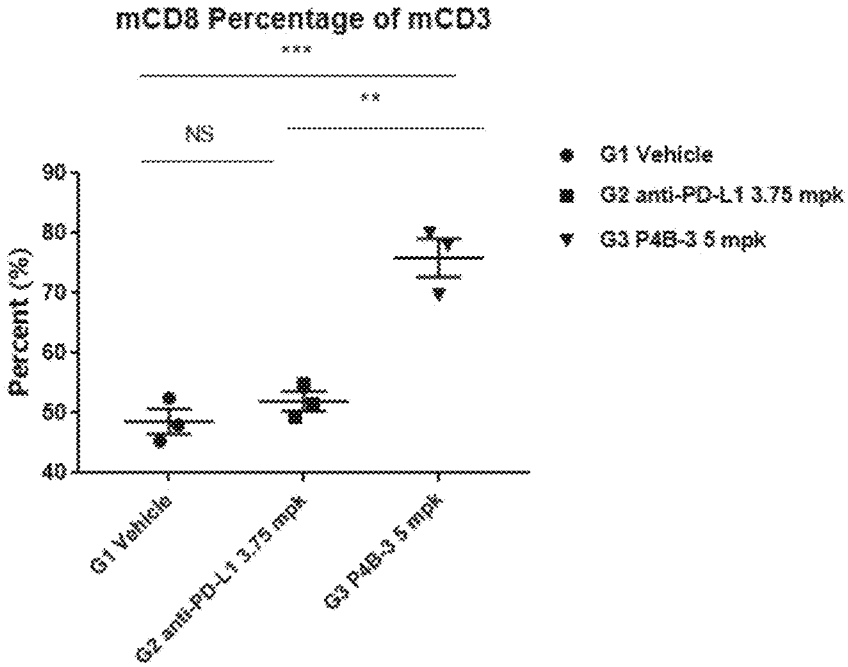
FIG. 12 shows the mCD8+ T cells percentage of mCD3 in TME(Tumor MicroEnvironment).
Figure 13:
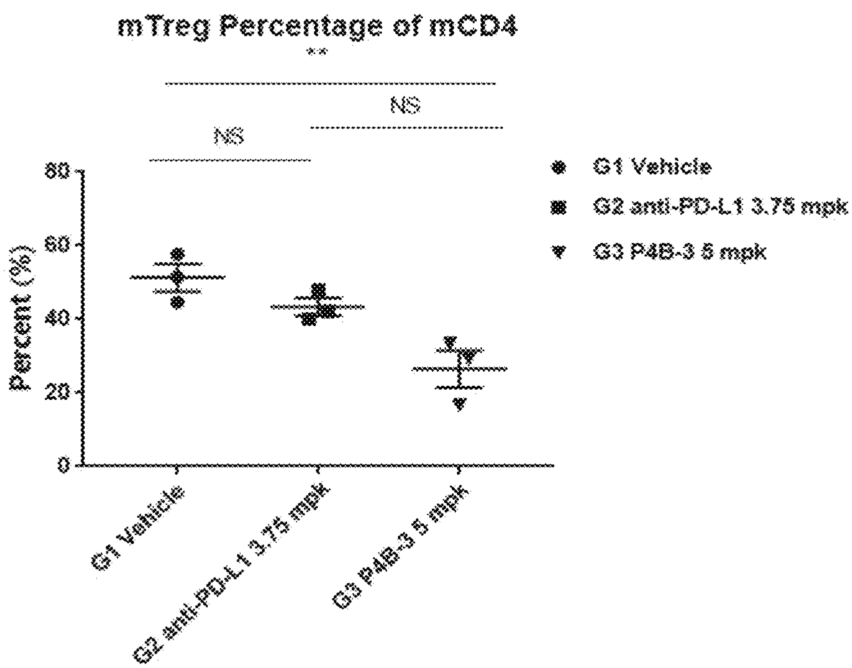
FIG. 13 shows the mTregs percentage of mCD4 in TME.

Results can be seed in FIGS. 11, 12 and 13. These results indicated that in BALB/c-huPD-L1/hu4-1BB KI mice model bearing MC38-huPD-L1 cells, P4B-3 showed strong anti-tumor efficacy. In addition, the P4B-3 can also elevate the CD8+ ratio and reduce the Treg ratio in tumor microenvironment.

TABLE 6

| tumor growth inhibition (tumor volume) | | | | | |
|---|---|---|---|---|---|
| Group | Dose | Animal number | Tumor volume(mm3)[a] (on Day 24) | TGI (%) [b] | P [c] |
| Vehicle (PBS) | / | 6 | 1699 ± 349 | / | / |
| Anti PD-L1 | 3.75 mg/kg | 7 | 519 ± 141 | 70.5% | <0.001 |
| P4B-3 | 5 mg/kg | 7 | 335 ± 133 | 81.8% | <0.001 |
| Anti 4-1BB | 3.75 mg/kg | 7 | 973 ± 287 | 46.1% | <0.001 |

Note:
[a]Tumor volume data were expressed as Mean ± SEM;
[b] TGI = (1-relative tumor volume in treated group/relative tumor volume in Vehicle group)*100%
[c] To assess the effect as compared to Vehicle group, a two-way ANOVA was performed, followed by Tukey's multiple comparison test.

Example 11 Pharmacokinetic Study of P4B-3 in Rats

Pharmacokinetic profile of P4B-3 in rats was evaluated. Procedures involving the care and use of animals in the study were reviewed and approved by PhamaLagancy. Three male SD rats (Shanghai Sippr-BK laboratory animal Co. Ltd.) were used.

In the study, P4B-3 was injected intravenously into the rats at a single dose of 10 mg/kg. Blood samples were obtained at various time-points between 0 and 336 hours (0-14 days), in particular, on day 0 at 0 minute, 10 minute, 30 minute, 1 hour, 4 hour, 8 hour, on day 1, and day 2, day 4, day 7, day 10 and day 14. All samples were processed to obtain plasma, and the plasma was cryopreserved at −70~−86° C. until being analyzed. The concentration of P4B-3 present in the plasma was determined by PD-L1 and 4-1BB antigen capture assay. The pharmacokinetic parameters were listed in Table 7.

4-1BB antigen capture assay: Human 4-1BB, human Fc tag protein (Hu4-1BB-huFc, SEQ ID NO:81) was immobilized onto 96-well plates (Costar, Cat #42592) at 0.5 µg/mL by incubation in Carbonate buffer (pH 9.6) overnight at 4° C. The plates were then blocked by incubation with 1% BSA (Sangon Biotech, Cat #A500023-0025) in PBS (Hyclone, Cat #SH30256.01) for one hour at 37° C. After blocking, the plates were washed three times with PBST (PBS containing 0.05% Tween20). P4B-3 was diluted at 0.1 µg/mL in the serum dilution buffer (PBS containing 0.05% Tween 20 and 0.5% BSA including 2% v/v rat serum) and 3-fold serial diluted 6 times, total 7 concentration antibody solution as standard curve. At the same time, 80 ng/mL, 8 ng/mL and 0.8 ng/mL of P4B3 as the high, middle and low quality control respectively were diluted by serum dilution buffer. All rat serum samples were diluted by pre-dose mixed rat serum and dilution buffer (PBS containing 0.05% Tween 20 and 0.5% BSA), to keep the final concentration in the range of 80-0.8 ng/mL, and containing 2% v/v rat serum in sample dilution. The standard curve, quality control and samples were added into plate and incubated for one hour at 37° C. Then, the plates were washed three times with PBST, incubated for one hour at 37° C. with Peroxidase AffiniPure Goat Anti-Human IgG, $F(ab')_2$ fragment specific (Jackson ImmunoResearch. Cat #109-035-097) diluted 1/10,000 in the dilution buffer, and then washed with PBST again. 50 µL/well TMB (Thermo, Cat #34028) was added into plates, after 15 minutes, reaction was stopped with IM $H_2SO_4$. The absorbance at 450 nm-620 nm was determined.

PD-L1 antigen capture assay: Human PD-L1, his tag protein (huPD-L1-his, ACRO, Cat #10084-H08H) was immobilized onto 96-well plates (Costar, Cat #42592) at 0.5 µg/mL by incubation in carbonate buffer solution (pH 9.6) overnight at 4° C. The plates were then blocked by incubation with 1% BSA in PBS for one hour at 3TC. After blocking, the plates were washed three times with PBST (PBS containing 0.05% Tween20). P4B-3 were diluted at 0.1 µg/mL in the serum dilution buffer (PBS containing 0.05% Tween 20 and 0.5% BSA including 2% v/v rat serum) and 3-fold serial diluted 6 times, total 7 concentration antibody solution as standard curve. At the same time, 80 ng/mL, 8 ng/mL and 0.8 ng/mL of P4B3 as the high, middle and low quality control respectively were diluted by serum dilution buffer. All rat serum samples were diluted by pre-dose mixed rat serum and dilution buffer (PBS containing 0.05% Tween 20 and 0.5% BSA), to keep the final concentration in the range of 80-0.8 ng/mL, and containing 2% v/v rat serum in sample dilution. The standard curve, quality control and samples were added into plate and incubated for one hour at 37° C. Then, the plates were washed three times with PBST, incubated for one hour at 37° C. with Peroxidase AffiniPure Goat Anti-Human IgG, Fc fragment specific (Jackson ImmunoResearch, Cat #109-035-098) diluted 1/20,000 in the dilution buffer, and then washed with PBST again. 50 µL/well TMB (Thermo, Cat #34028) was added into plates, after 15 minutes, reaction was stopped with IM $H_2SO4$. The absorbance at 450 nm-620 nm was determined.

TABLE 7

| PK parameters of P4B-3 in rats | | | |
|---|---|---|---|
| Parameter | Units | antigen PD-L1 capture | antigen 4-1BB capture |
| HL_Lambda_z | day | 6.71 | 6.99 |
| Cmax | ug/ml | 194.73 | 136.25 |
| AUClast | day*ug/ml | 609.82 | 455.78 |
| AUCINF_obs | day*ug/ml | 801.80 | 586.16 |
| Cl_obs | ml/day/kg | 12.54 | 17.19 |
| MRTINF_obs | day | 9.46 | 9.09 |
| Vss_obs | ml/kg | 118.27 | 156.29 |

The pharmacokinetics of the P4B-3 performed well in rats, indicating it can be used in pharmaceutical area.

While the disclosure has been described above in connection with one or more embodiments, it should be understood that the disclosure is not limited to those embodiments, and the description is intended to cover all alternatives, modifications, and equivalents, as may be included within the spirit and scope of the appended claims. All referenced cited herein are further incorporated by reference in their entirety.

Sequence description:

| SEQ ID NO: | Sequence description | Type | Specific sequences |
|---|---|---|---|
| 1 | VH-CDR1 of 41BB-2 | Amino acid sequence (AA) | SYAMH |
| 2 | VH-CDR2 of 41BB-2 | AA | VISYDGSKKWYADSVKG |
| 3 | VH-CDR3 of 41BB-2 | AA | NQGSGSYLYYYYMDV |
| 4 | VL-CDR1 of 41BB-2 | AA | TGTSSDVGGYNYVS |
| 5 | VL-CDR2 of 41BB-2 | AA | EVSNRPS |
| 6 | VL-CDR3 of 41BB-2 | AA | SSYTSSSTFYV |
| 7 | VH-CDR1 of 41BB-9 | AA | SYAIS |
| 8 | VH-CDR2 of 41BB-9 | AA | GIIPISGAVNYAQKFQG |
| 9 | VH-CDR3 of 41BB-9 | AA | DQFIKYYDFSSGYFPNGFDI |
| 10 | VL-CDR1 of 41BB-9 | AA | SGDKLGDKYAA |
| 11 | VL-CDR2 of 41BB-9 | AA | QDTVRPS |
| 12 | VL-CDR3 of 41BB-9 | AA | QTWVSSTGV |
| 13 | VH-CDR1 of 41BB-13 | AA | SYYMH |
| 14 | VH-CDR2 of 41BB-13 | AA | IINPSGGSTSYAQKFQG |
| 15 | VH-CDR3 of 41BB-13 | AA | DLGEGYDFWSGYYTPSGAFDI |
| 16 | VL-CDR1 of 41BB-13 | AA | TGTSSDVGGYNYVS |
| 17 | VL-CDR2 of 41BB-13 | AA | DVTTRPS |
| 18 | VL-CDR3 of 41BB-13 | AA | SSYTSYSTWV |
| 19 | VH-CDR1 of 41BB-27 | AA | SSHWWS |
| 20 | VH-CDR2 of 41BB-27 | AA | EIYHSGRTYYNPSLKS |
| 21 | VH-CDR3 of 41BB-27 | AA | EDGGIMDV |
| 22 | VL-CDR1 of 41BB-27 | AA | QGDSLRRFYAS |
| 23 | VL-CDR2 of 41BB-27 | AA | GKNNRPS |
| 24 | VL-CDR3 of 41BB-27 | AA | SSRDRSGYRWV |

-continued

Sequence description:

| SEQ ID NO: | Sequence description | Type | Specific sequences |
|---|---|---|---|
| 25 | VH of 41BB-2 | AA | QVQLQESGGGLVQPGGSLRLSCAVSGFTFSSYAMHWVRQAPGKGLEWVAVISYDGSKKWYADSVKGRFTISRDNSKNTLYLQMNSLRAEDTAVYYCARNQGSGSYLYYYYMDVWGKGTTVTVSS |
| 26 | VL of 41BB-2 | AA | QSALTQPRSVSGSPGQSVTISCTGTSSDVGGYNYVSWYQQLPGKAPKVIIYEVSNRPSGVSNRFSGSKSGNTASLTISGVQSEDEADYYCSSYTSSSTFYVFGTGTQLTVLX1 (X1 = S or G) |
| 27 | VH of 41BB-9 | AA | QVQLVQSGAEVKKPGSSVKVSCKASGGTFSSYAISWVRQAPGQGLEWMGGIIPISGAVNYAQKFQGRVTITADESTSTAYMELSSLRSEDTAVYYCARDQFIKYYDFSSGYFPNGFDIWGKGTLVTVSS |
| 28 | VL of 41BB-9 | AA | QTVVTQPPSVSVSPGQTASITCSGDKLGDKTAAWYQQKPGQSPVLVIYQDTVRPSGIPERFSGSNSGNTATLTISGTQAMDEADYYCQTWVSSTGVFGTGTKVTVLG |
| 29 | VH of 41BB-13 | AA | EVQLVETGVEVKKPGASVKVSCKASGYTFTSYYMHWVRQAPGQGLEWMGIINPSGGSTSYAQKFQGRVTMTRDTSTSTAYMELSSLRSEDTAVYYCARDLGEGYDFWSGYYTPSGAFDIWGKGTMVTVSS |
| 30 | VL of 41BB-13 | AA | QSALTQPASVSGSPGQSITISCTGTSSDVGGYNYVSWYQQRPGKAPKLIIYDVTTRPSGVSNRFSGSKSGTTASLTISGLQAEDEADYYCSSYTSYSTWVFGGGTKLTVLG |
| 31 | VH of 41BB-27 | AA | QVQLQESGPGPVKPSETLSLTCAVSGGSISSSHWWSWVRQPPGKGLEWIGEIYHSGRTYYNPSLKSRVTISVDTSRNQFSLKLSSVTAADTAVYYCAREDGGIMDVWGQGTLVTVSS |
| 32 | VL of 41BB-27 | AA | LSSELTQDPAVSVALGQTVRITCQGDSLRRFYASWYQQKPGQAPVLVIYGKNNRPSGIPDRFSASDSGNTASLTITGAQAEDEADYYCSSRDRSGYRWVFGGGTKVTVLG |
| 33 | Heavy chain constant region from IgG2 | AA | c.f., sequence listing |
| 34 | Heavy chain constant region from IgG2 (mutant) | AA | c.f., sequence listing |
| 35 | Light chain constant region (Lambda) | AA | c.f., sequence listing |
| 36 | Linker | AA | GGGGSGGGGSGGGGS |

-continued

Sequence description:

| SEQ ID NO: | Sequence description | Type | Specific sequences |
|---|---|---|---|
| 37 | Heavy chain of Urelumab | AA | c.f., sequence listing |
| 38 | Light chain of Urelumab | AA | c.f., sequence listing |
| 39 | Human 4-1BB | AA | c.f., sequence listing |
| 40 | VH-CDR1 of anti-PDL1 | AA | SGYWN |
| 41 | VH-CDR2 of anti-PDL1 | AA | YVSYTGSTYYIPSLKS |
| 42 | VH-CDR3 of anti-PDL1 | AA | YRDWLHGYFDY |
| 43 | VL-CDR1 of anti-PDL1 | AA | KASQNVMDNVA |
| 44 | VL-CDR2 of anti-PDL1 | AA | SASYRFS |
| 45 | VL-CDR3 of anti-PDL1 | AA | QQYNGYPLT |
| 46 | VH of anti-PDL1 | AA | EVQLQESGPGLVKPSQTLSLTC<br>TVSGDSFSSGYWNWIRQHPGKG<br>LEYIGYVSYTGSTYYIPSLKSR<br>VTISRDTSKNQFSLKLSSVTAA<br>DTAVYYCAGYRDWLHGYFDYWG<br>QGTTVTVSS |
| 47 | VL of anti-PDL1 | AA | DIQMTQSPSSLSASVGDRVTIT<br>CKASQNVMDNVAWYQQKPGKAP<br>KRLIYSASYRFSGVPSRFSGSG<br>SGTEFTLTISSLQPEDFATYYC<br>QQYNGYPLTFGQGTKLEIK |
| 48 | Heavy chain of P4B-2 (Chain 1) | AA | QVQLQESGGGLVQPGGSLRLSC<br>AVSGFTFSSYAMHWVRQAPGKC<br>LEWVAVISYDGSKKWYADSVKG<br>RFTISRDNSKNTLYLQMNSLRA<br>EDTAVYYCARNQGSGSYLYYYY<br>MDVWGKGTTVTVSSGSSSSGSS<br>SSGSSSSQSALTQPRSVSGSPG<br>QSVTISCTGTSSDVGGYNYVSW<br>YQQLPGKAPKVIIYEVSNRPSG<br>VSNRFSGSKSGNTASLTISGVQ<br>SEDEADYYCSSYTSSSTFYVFG<br>CGTQLTVLGGGGSEVQLQESGP<br>GLVKPSQTLSLTCTVSGDSFSS<br>GYWNWIRQHPGKGLEYIGYVSY<br>TGSTYYIPSLKSRVTISRDTSK<br>NQFSLKLSSVTAADTAVYYCAG<br>YRDWLHGYFDYWGQGTTVTVSS<br>ASTKGPSVFPLAPSSKSTSGGT<br>AALGCLVKDYFPEPVTVSWNSG<br>ALTSGVHTFPAVLQSSGLYSLS<br>SVVTVPSSSLGTQTYICNVNHK<br>PSNTKVDKKVEPKSCDKTHTCP<br>PCPAPEAAGGPSVFLFPPKPKD<br>TLMISRTPEVTCVVVAVSHEDP<br>EVKFNWYVDGVEVHNAKTKPRE<br>EQYNSTYRVVSVLTVLHQDWLN<br>GKEYKCKVSNKALAAPIEKTIS<br>KAKGQPREPQVYTLPPSRDELT<br>KNQVSLTCLVKGFYPSDIAVEW<br>ESNGQPENNYKTTPPVLDSDGS<br>FFLYSKLTVDKSRWQQGNVFSC<br>SVMHEALHNHYTQKSLSLSPGK |

-continued

Sequence description:

| SEQ ID NO: | Sequence description | Type | Specific sequences |
|---|---|---|---|
| 49 | Light chain of P4B-2/ P4B-3 (Chain 2, light chain of anti-PD-L1) | AA | DIQMTQSPSSLSASVGDRVTIT<br>CKASQNVMDNVAWYQQKPGKAP<br>KRLIYSASYRFSGVPSRFGSGS<br>GTEFTLTISSLQPEDFATYYCQ<br>QYNGYPLTFGQGTKLEIKRTVA<br>APSVFIFPPSDEQLKSGTASVV<br>CLLNNFYPREAKVQWKVDNALQ<br>SGNSQESVTEQDSKDSTYSLSS<br>TLTLSKADYEKHKVYACEVTHQ<br>GLSSPVTKSFNRGEC |
| 50 | Heavy chain of P4B-3 (Chain 1) | AA | EVQLQESGPGLVKPSQTLSLTC<br>TVSGDSFSSGYWNWIRQHPGKG<br>LEYIGYVSYTGSTYYIPSLKSR<br>VTISRDTSKNQFSLKLSSVTAA<br>DTAVYYCAGYRDWLHGYFDYWG<br>QGTTVTVSSASTKGPSVFPLAP<br>SSKSTSGGTAALGCLVKDYFPE<br>PVTVSWNSGALTSGVHTFPAVL<br>QSSGLYSLSSVVTVPSSSLGTQ<br>TYICNVNHKPSNTKVDKKVEPK<br>SCDKTHTCPPCPAPEAAGGPSV<br>FLFPPKPKDTLMISRTPEVTCV<br>VVAVSHEDPEVKFNWYVDGVEV<br>HNAKTKPREEQYNSTYRVVSVL<br>TVLHQDWLNGKEYKCKVSNKAL<br>AAPIEKTISKAKGQPREPQVYT<br>LPPSRDELTKNQVSLTCLVKGF<br>YPSDIAVEWESNGQPENNYKTT<br>PPVLDSDGSFFLYSKLTVDKSR<br>WQQGNVFSCSVMHEALHNHYTQ<br>KSLSLSPGKGGGGSGGGGSGGG<br>GSQVQLQESGGGLVQPGGSLRL<br>SCAVSGFTFSSYAMHWVRQAPG<br>KCLEWVAVISYDGSKKWYADSV<br>KGRFTISRDNSKNTLYLQMNSL<br>RAEDTAVYYCARNQGSGSYLYY<br>YYMDVWGKGTTVTVSSGSSSSG<br>SSSSGSSSSQSALTQPRSVSGS<br>PGQSVTISCTGTSSDVGGYNYV<br>SWYQQLPGKAPKVIIYEVSNRP<br>SGVSNRFSGSKSGNTASLTISG<br>VQSEDEADYYCSSYTSSSTFYV<br>FGCGTQLTVL |
| 51 | Linker | AA | GSSSSGSSSSGSSSS |
| 52 | Linker | AA | $(GGGGS)_n$ n = 1, 2, 3, 4, 5, or 6 |
| 53 | VH-CDR1 of anti-PDL1 | NA (nucleic acid) | TCCGGCTACTGGAAC |
| 54 | VH-CDR2 of anti-PDL1 | NA | TACGTGTCCTACACCGGCTCTA<br>CCTACTACATCCCCAGCCTGAA<br>GTCC |
| 55 | VH-CDR3 of anti-PDL1 | NA | TACAGAGATTGGCTGCACGGCT<br>ACTTCGACTAC |
| 56 | VL-CDR1 of anti-PDL1 | NA | AAGGCCAGCCAGAACGTGATGG<br>ACAACGTGGCC |
| 57 | VL-CDR2 of anti-PDL1 | NA | TCCGCCTCCTACAGATTCTCT |
| 58 | VL-CDR3 of anti-PDL1 | NA | CAGCAGTACAACGGCTACCCTC<br>TGACC |
| 59 | VH of anti-PDL1 | NA | c.f., sequence listing |

-continued

Sequence description:

| SEQ ID NO: | Sequence description | Type | Specific sequences |
|---|---|---|---|
| 60 | VL of anti-PDL1 | NA | c.f., sequence listing |
| 61 | Human PD-L1 | AA | c.f., sequence listing |
| 62 | Human PD-L1 | NA | c.f., sequence listing |
| 63 | Light chain constant region (Kappa) | AA | c.f., sequence listing |
| 64 | Light chain constant region (Kappa) | NA | c.f., sequence listing |
| 65 | P4B-2 heavy chain (Chain 1) | NA | c.f., sequence listing |
| 66 | P4B-3 heavy chain (Chain 1) | NA | c.f., sequence listing |
| 67 | VH-CDR1 of 41BB-2 | NA | AGCTACGCCATGCAC |
| 68 | VH-CDR2 of 41BB-2 | NA | TACGACGGCAGCAAGAAGTGGT ATGCTGATAGCGTGAAGGGC |
| 69 | VH-CDR3 of 41BB-2 | NA | AATCAGGGCAGCGGCTCTTATC TGTACTATTACTATATGGACGT G |
| 70 | VL-CDR1 of 41BB-2 | NA | ACAGGCACCTCCTCCGACGTGG GCGGCTACAACTACGTGAGC |
| 71 | VL-CDR2 of 41BB-2 | NA | GAGGTGTCCAACAGGCCCTCC |
| 72 | VL-CDR3 of 41BB-2 | NA | TCCTCCTACACCTCCAGCTCCA CCTTCTACGTG |
| 73 | VH of 41BB-2 | NA | c.f., sequence listing |
| 74 | VL of 41BB-2 | NA | c.f., sequence listing |

-continued

Sequence description:

| SEQ ID NO: | Sequence description | Type | Specific sequences |
|---|---|---|---|
| 75 | Heavy chain constant region from IgG4 with S228P mutation | AA | c.f., sequence listing |
| 76 | the light chain of P4B2 or P4B3 (Chain 2) | NA | c.f., sequence listing |
| 77 | VH of anti-4-1BB of P4B2 of P4B3 | AA | c.f., sequence listing |
| 78 | VL of anti-4-1BB of P4B2 of P4B3 | AA | c.f., sequence listing |
| 79 | VH of anti-4-1BB of P4B2 of P4B3 | NA | c.f., sequence listing |
| 80 | VL of anti-4-1BB of P4B2 of P4B3 | NA | c.f., sequence listing |
| 81 | Hu4-1BB-hFc | AA | c.f., sequence listing |
| 82 | Heavy chain of IgG (negative control) | AA | c.f., sequence listing |
| 83 | Light chain of IgG (negative control) | AA | c.f., sequence listing |
| 84 | INBRX-105-1 | AA | c.f., sequence listing |
| 85 | Heavy chain constant region from IgG1 (mutant) | NA | c.f., sequence listing |

We claim:

1. An antibody or an antigen-binding portion thereof that binds to 4-1BB, comprising heavy chain variable region CDR1, CDR2 and CDR3 and light chain variable region CDR1, CDR2 and CDR3, wherein (i) the heavy chain variable region CDR1, CDR2 and CDR3 comprise the sequences of SEQ ID NOs: 1, 2 and 3 respectively, and the light chain variable region CDR1, CDR2 and CDR3regions comprise the sequences of SEQ ID NOs: 4, 5 and 6 respectively;

(ii) the heavy chain variable region CDR1, CDR2 and CDR3 comprise the sequences of SEQ ID NOs: 7, 8 and 9 respectively, and the light chain variable region CDR1, CDR2 and CDR3regions comprise the sequences of SEQ ID NOs: 10, 11 and 12 respectively;

(iii) the heavy chain variable region CDR1, CDR2 and CDR3 comprise the sequences of SEQ ID NOs: 13, 14 and 15 respectively, and the light chain variable region CDR1, CDR2 and CDR3comprise the sequences of SEQ ID NOs: 16, 17 and 18 respectively; or (iv) the heavy chain variable region CDR1, CDR2 and CDR3 comprise the sequences of SEQ ID NOs: 19, 20 and 21 respectively, and the light chain variable region CDR1, CDR2 and CDR3comprise the sequences of SEQ ID NOs: 22, 23 and 24 respectively.

2. The antibody or the antigen-binding portion thereof of claim 1, wherein (a) the heavy chain variable region and the light chain variable region of (i) comprise amino acid sequences having at least 80%, 81%, 82%, 83%, 84%, 85%, 86%, 87%, 88%, 89%, 90%, 91%, 92%, 93%, 94% 95%, 96%, 97%, 98%, 99% or 100% identity to SEQ ID NOs: 25 and 26 (X1=S), respectively, SEQ ID NOs: 25 and 26 (X1=G), respectively, or SEQ ID NOs: 77 and 78,respectively;

(b) the heavy chain variable region and the light chain variable region of (ii) comprise amino acid sequences having at least 80%, 81%, 82%, 83%, 84%, 85%, 86%, 87%, 88%, 89%, 90%, 91%, 92%, 93%, 94% 95%, 96%, 97%, 98%, 99% or 100% identity to SEQ ID NOs: 27 and 28,respectively;

(c) the heavy chain variable region and the light chain variable region of (iii) comprise amino acid sequences having at least 80%, 81%, 82%, 83%, 84%, 85%, 86%, 87%, 88%, 89%, 90%, 91%, 92%, 93%, 94% 95%, 96%, 97%, 98%, 99% or 100% identity to SEQ ID NOs: 29 and 30,respectively; or (d) the heavy chain variable region and the light chain variable region of (iv) comprise amino acid sequences having at least 80%, 81%, 82%, 83%, 84%, 85%, 86%, 87%, 88%, 89%, 90%, 91%, 92%, 93%, 94% 95%, 96%, 97%, 98%, 99% or 100% identity to SEQ ID NOs: 31 and 32,respectively.

3. The antibody or the antigen-binding portion thereof of claim 1, comprising a heavy chain constant region having the amino acid sequence of SEQ ID NO: 33, SEQ ID NO: 34, or SEQ ID NO: 75, linked to the heavy chain variable region, and/or a light chain constant region having the amino acid sequence of SEQ ID NO: 35 or SEQ ID NO: 63, linked to the light chain variable region.

4. The antibody or the antigen-binding portion thereof of claim 1, which activates 4-1BB signaling, and which is a monoclonal antibody.

5. The antibody or the antigen-binding portion thereof of claim 1, wherein the antibody is a human antibody.

6. The antibody or the antigen-binding portion thereof of claim 1, wherein the antibody is an IgG1, IgG2 or IgG4 isotype.

7. The antibody or the antigen-binding portion thereof of claim 1, wherein the antigen-binding portion thereof is selected from (i) a Fab fragment; (ii) a $F(ab')_2$ fragment; (iii) a Fd fragment; (iv) a Fv fragment, (v) a dAb fragment; and (vi) a single chain Fv (scFv).

8. A pharmaceutical composition comprising the antibody or antigen-binding portion thereof of claim 1, and a pharmaceutically acceptable carrier.

9. A composition comprising the antibody or antigen-binding portion thereof of claim 1, and further comprising one or more therapeutic agents selected from: a chemotherapeutic agent, a cytotoxic agent, a vaccine, an anti-infection agent, a small molecule drug, an immunomodulator, and an antibody to an immune checkpoint molecule.

10. A bispecific antibody comprising:

a first binding region which specifically binds to 4-1BB which comprises the antibody or the antigen-binding portion thereof of claim 1, and a second binding region which specifically binds to a second antigen.

11. The bispecific antibody of claim 10, wherein the second antigen is selected from PD-L1, PD1 or CTLA-4.

12. A bispecific antibody comprising:

(1) Chain 1: a heavy chain of an antibody against a second antigen linked at its N-terminus or C- terminus to the antigen-binding portion of claim 1 wherein the antigen-binding portion of claim 1 is an scFv; and (2) Chain 2: a light chain of the antibody against the second antigen.

13. The bispecific antibody of claim 12, wherein the scFv comprises a heavy chain variable region and a light chain variable region, and wherein the heavy chain variable region comprises CDR1, CDR2 and CDR3 consisting of the sequence of SEQ ID NO: 1, 2 and 3,respectively, and the light chain variable region comprises CDR1, CDR2 and CDR3 consisting of the sequences of SEQ ID NO: 4, 5 and 6, respectively.

14. The bispecific antibody of claim 12, wherein the second antigen is selected from PD-L1, PD1, or CTLA-4.

15. The bispecific antibody of claim 14, wherein the second antigen is PD-L1 and the antibody against PD-L1 comprises a heavy chain variable region and a light chain variable region, wherein the heavy chain variable region comprises CDR1, CDR2 and CDR3consisting of the sequences of SEQ ID NO: 40, 41, and 42, respectively, and wherein the light chain variable region comprises CDR1, CDR2 and CDR3 consisting of the sequences of SEQ ID NO: 43,44, and 45, respectively.

16. The bispecific antibody of claim 15, wherein

Chain 1 of the bispecific antibody comprises an amino acid sequence having at least 90%, 91%, 92%, 93%, 94%, 95%, 96%, 97%, 98%, 99% or 100% identity to the amino acid sequence of: (a) SEQ ID NO: 48 when the heavy chain of the antibody against the second antigen is linked at its N-terminus to the scFv, or (b) SEQ ID NO: 50 when the heavy chain of the antibody against the second antigen is linked at its C-terminus to the scFv, and wherein Chain 2 of the bispecific antibody comprises an amino acid sequence having at least 90%, 91%, 92%, 93%, 94%, 95%, 96%, 97%, 98%, 99% or 100% identity to the amino acid sequence of SEQ ID NO: 49.

17. A pharmaceutical composition comprising the bispecific antibody of claim 14, and a pharmaceutically acceptable carrier.

18. A polynucleotide encoding the bispecific antibody of claim 15.

19. A method for treating a cancer in a subject, comprising administering to the subject a therapeutically effective amount of the bispecific antibody of claim 16.

* * * * *